US011833150B2

(12) United States Patent
Bates et al.

(10) Patent No.: US 11,833,150 B2
(45) Date of Patent: Dec. 5, 2023

(54) METHODS OF TREATING LIVER DISEASE

(71) Applicant: Gilead Sciences, Inc., Foster City, CA (US)

(72) Inventors: Jamie Geier Bates, Burlingame, CA (US); David Gordon Clarkson Breckenridge, San Mateo, CA (US); John T. Liles, San Jose, CA (US)

(73) Assignee: Gilead Sciences, Inc., Foster City, CA (US)

( * ) Notice: Subject to any disclaimer, the term of this patent is extended or adjusted under 35 U.S.C. 154(b) by 484 days.

(21) Appl. No.: 16/803,824

(22) Filed: Feb. 27, 2020

(65) Prior Publication Data
US 2021/0015818 A1  Jan. 21, 2021

Related U.S. Application Data

(63) Continuation of application No. 15/935,759, filed on Mar. 26, 2018, now abandoned.

(60) Provisional application No. 62/586,354, filed on Nov. 15, 2017, provisional application No. 62/482,105, filed on Apr. 5, 2017, provisional application No. 62/477,697, filed on Mar. 28, 2017.

(51) Int. Cl.
*A61K 31/519* (2006.01)
*A61K 31/4439* (2006.01)
*A61P 1/16* (2006.01)

(52) U.S. Cl.
CPC ........ *A61K 31/519* (2013.01); *A61K 31/4439* (2013.01); *A61P 1/16* (2018.01)

(58) Field of Classification Search
CPC .................... A61K 31/4439; A61K 31/519
See application file for complete search history.

(56) References Cited

U.S. PATENT DOCUMENTS

| | | | |
|---|---|---|---|
| 4,670,560 A | 6/1987 | Press et al. |
| 4,943,584 A | 7/1990 | Theobald et al. |
| 5,256,666 A | 10/1993 | Mueller et al. |
| 5,258,551 A | 11/1993 | Murabayashi et al. |
| 5,502,252 A | 3/1996 | Takase et al. |
| 5,633,272 A | 5/1997 | Talley et al. |
| 5,849,746 A | 12/1998 | Chambers et al. |
| 5,854,268 A | 12/1998 | Baker et al. |
| 5,912,243 A | 6/1999 | Dowling et al. |
| 6,180,635 B1 | 1/2001 | Cheshire et al. |
| 6,197,780 B1 | 3/2001 | Munter et al. |
| 6,407,140 B1 | 6/2002 | Gregory et al. |
| 6,974,830 B2 | 12/2005 | Bauer et al. |
| 7,034,046 B2 | 4/2006 | Bauer et al. |
| 7,098,336 B2 | 8/2006 | Bauer et al. |
| 7,560,551 B2 | 7/2009 | Cee et al. |
| 8,188,080 B2 | 5/2012 | Mustelin et al. |
| 8,193,192 B2 | 6/2012 | Kremoser et al. |
| 8,222,256 B2 | 7/2012 | Zhang |
| 8,952,042 B2 | 2/2015 | Kremoser et al. |
| 8,969,557 B2 | 3/2015 | Harriman et al. |
| 9,139,539 B2 | 9/2015 | Kinzel et al. |
| 9,346,822 B2 | 5/2016 | Cho et al. |
| 9,453,026 B2 | 9/2016 | Harriman et al. |
| 9,539,244 B2 | 1/2017 | Kinzel et al. |
| 9,751,874 B2 | 9/2017 | Gege et al. |
| 9,820,979 B2 | 11/2017 | Kinzel et al. |
| 9,855,249 B2 | 1/2018 | Cole et al. |
| 9,938,278 B2 | 4/2018 | Gege et al. |
| 9,944,655 B2 | 4/2018 | Harriman et al. |
| 9,988,399 B2 | 6/2018 | Greenwood et al. |
| 10,183,951 B2 | 1/2019 | Amedio, Jr. et al. |
| 10,220,027 B2 | 3/2019 | Kinzel et al. |
| 10,472,374 B2 | 11/2019 | Bhat et al. |
| 10,485,795 B2 | 11/2019 | Kinzel et al. |
| 10,487,090 B2 | 11/2019 | Calimsiz et al. |
| 10,981,881 B2 | 4/2021 | Blomgren et al. |
| 2003/0130296 A1 | 7/2003 | Bauer et al. |
| 2003/0149087 A1 | 8/2003 | Bauer et al. |
| 2003/0187042 A1 | 10/2003 | Bauer et al. |
| 2003/0187254 A1 | 10/2003 | Perry et al. |
| 2003/0191142 A1 | 10/2003 | Cheshire et al. |
| 2004/0048908 A1 | 3/2004 | Momose et al. |
| 2004/0105883 A1 | 6/2004 | Gao et al. |
| 2004/0105884 A1 | 6/2004 | Gao et al. |
| 2004/0105885 A1 | 6/2004 | Gao |
| 2004/0106607 A1 | 6/2004 | Arora et al. |
| 2004/0131670 A1 | 7/2004 | Gao |
| 2004/0152699 A1 | 8/2004 | Arora et al. |
| 2004/0157881 A1 | 8/2004 | Maekawa et al. |
| 2005/0124636 A1 | 6/2005 | Sharma et al. |
| 2005/0272779 A1 | 12/2005 | Edwards et al. |

(Continued)

FOREIGN PATENT DOCUMENTS

| | | |
|---|---|---|
| CA | 1145344 A | 4/1983 |
| CN | 1106663 A | 8/1995 |

(Continued)

OTHER PUBLICATIONS

Abel et al., (2010) "Synthesis and pharmacological validation of a novel series of non-steroidal FXR agonists", Bioorganic & Medicinal Chemistry Letters 20: 4911-4917.
Abu-Hayyeh et al., (2010) "Sulphated progesterone metabolites attenuate FXR function", 61st Annual Meeting of the American Association for the Study of Liver Diseases (Abstract).
Adams et al., (2012) "In vitro and in vivo regulation of FGF21 by FXR", 2012 Genetic and Molecular Basis of Obesity and Body Weight Regulation (J7) held jointly with 2012 Pathogenesis of Diabetes: Emerging Insights into Molecular Mechanisms (J8), (Abstract).
Adorini, (2008) "Clinical Translation of FXR agonists for the Treatment of Liver and Metabolic Disorders", 2008 Nuclear Receptors: Orphan Brothers (Z1), (Abstract).

(Continued)

*Primary Examiner* — Jeffrey S Lundgren
*Assistant Examiner* — Chris E Simmons
(74) *Attorney, Agent, or Firm* — SHEPPARD MULLIN RICHTER & HAMPTON LLP

(57) ABSTRACT

The present disclosure relates to a method of preventing and/or treating liver disease comprising administering an ACC inhibitor in combination with an FXR agonist to a patient in need thereof.

4 Claims, 9 Drawing Sheets

Specification includes a Sequence Listing.

(56) References Cited

U.S. PATENT DOCUMENTS

| | | |
|---|---|---|
| 2006/0039943 A1 | 2/2006 | Applebaum et al. |
| 2006/0063772 A1 | 3/2006 | Arora et al. |
| 2007/0010562 A1 | 1/2007 | Bauer et al. |
| 2007/0208040 A1 | 9/2007 | Elzein et al. |
| 2008/0032990 A1 | 2/2008 | Khalifah et al. |
| 2008/0114044 A1 | 5/2008 | Epple et al. |
| 2008/0182837 A1 | 7/2008 | Steurer et al. |
| 2008/0194634 A1 | 8/2008 | Arndt et al. |
| 2008/0207910 A1 | 8/2008 | Podhorez et al. |
| 2008/0287465 A1 | 11/2008 | Tumey et al. |
| 2009/0074717 A1 | 3/2009 | Leivers et al. |
| 2009/0076103 A1 | 3/2009 | Olson et al. |
| 2009/0105251 A1 | 4/2009 | Jones et al. |
| 2009/0143451 A1 | 6/2009 | Andrews et al. |
| 2009/0197880 A1 | 8/2009 | Leivers et al. |
| 2009/0286782 A1 | 11/2009 | Ibrahim et al. |
| 2009/0286806 A1 | 11/2009 | Pajouhesh et al. |
| 2009/0306086 A1 | 12/2009 | Ibrahim et al. |
| 2010/0016313 A1 | 1/2010 | Millan et al. |
| 2010/0029655 A1 | 2/2010 | Leivers et al. |
| 2010/0048910 A1 | 2/2010 | Godschalx et al. |
| 2010/0093751 A1 | 4/2010 | Hynd et al. |
| 2010/0113473 A1 | 5/2010 | Player et al. |
| 2010/0184809 A1 | 7/2010 | Kremoser et al. |
| 2010/0197662 A1 | 8/2010 | Ogawa et al. |
| 2010/0210660 A1 | 8/2010 | Kremoser et al. |
| 2010/0216827 A1 | 8/2010 | Ma et al. |
| 2010/0234347 A1 | 9/2010 | Dollinger et al. |
| 2010/0240657 A1 | 9/2010 | Sapountzis et al. |
| 2010/0256145 A1 | 10/2010 | Bak-Jensen et al. |
| 2011/0044943 A1 | 2/2011 | Leivers et al. |
| 2011/0212975 A1 | 9/2011 | Kao et al. |
| 2011/0220880 A1 | 9/2011 | Cheng et al. |
| 2011/0257196 A1 | 10/2011 | Lu et al. |
| 2011/0288114 A1 | 11/2011 | Turner |
| 2011/0306493 A1 | 12/2011 | Paulini et al. |
| 2011/0312950 A1 | 12/2011 | Eckhardt et al. |
| 2012/0015988 A1 | 1/2012 | Hickey et al. |
| 2012/0021519 A1 | 1/2012 | Ichida et al. |
| 2012/0022067 A1 | 1/2012 | Chen et al. |
| 2012/0029027 A1 | 2/2012 | Estenne-Bouhtou et al. |
| 2012/0071524 A1 | 3/2012 | Lu et al. |
| 2012/0110705 A1 | 5/2012 | Le Vezouet et al. |
| 2012/0122681 A1 | 5/2012 | Le Vezouet et al. |
| 2012/0220603 A1 | 8/2012 | Pajouhesh et al. |
| 2012/0232116 A1 | 9/2012 | Kremoser et al. |
| 2012/0245166 A1 | 9/2012 | Grimaldi et al. |
| 2013/0123231 A1 | 5/2013 | Harriman et al. |
| 2013/0231348 A1 | 9/2013 | Campbell et al. |
| 2013/0261108 A1 | 10/2013 | Tully et al. |
| 2013/0281503 A1 | 10/2013 | Melander et al. |
| 2014/0039007 A1 | 2/2014 | Tully et al. |
| 2014/0221659 A1 | 8/2014 | Kinzel et al. |
| 2014/0249100 A1 | 9/2014 | Shalwitz et al. |
| 2015/0082981 A1 | 3/2015 | Shiflett |
| 2015/0291572 A1 | 10/2015 | Schunk et al. |
| 2016/0136138 A1 | 5/2016 | Shibata et al. |
| 2016/0297834 A1 | 10/2016 | Harriman et al. |
| 2016/0376279 A1 | 12/2016 | Evans et al. |
| 2017/0073635 A1 | 3/2017 | Zhang |
| 2017/0145028 A1 | 5/2017 | Ghosh et al. |
| 2017/0166582 A1 | 6/2017 | Ghosh et al. |
| 2017/0166583 A1 | 6/2017 | Ghosh et al. |
| 2017/0166584 A1 | 6/2017 | Ghosh et al. |
| 2017/0166585 A1 | 6/2017 | Bennett et al. |
| 2017/0204073 A1 | 7/2017 | Almstead et al. |
| 2017/0204096 A1 | 7/2017 | Gelin et al. |
| 2017/0267690 A1 | 9/2017 | Alexander et al. |
| 2017/0279055 A1 | 9/2017 | Jang et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0009754 A1 | 1/2018 | Long et al. |
| 2018/0021341 A1 | 1/2018 | Harriman et al. |
| 2018/0030003 A1 | 2/2018 | Wang et al. |
| 2018/0051258 A1 | 2/2018 | Zhang et al. |
| 2018/0099957 A1 | 4/2018 | Ma et al. |
| 2018/0123052 A1 | 5/2018 | Zysman-Colman et al. |
| 2018/0280394 A1 | 10/2018 | Bates et al. |
| 2018/0298025 A1 | 10/2018 | Geier et al. |
| 2019/0016732 A1 | 1/2019 | Bhat et al. |
| 2019/0134041 A1 | 5/2019 | Bates et al. |
| 2019/0241582 A1 | 8/2019 | Ghosh et al. |
| 2019/0247343 A1 | 8/2019 | Laruelle et al. |
| 2019/0308962 A1 | 10/2019 | Blomgren et al. |
| 2019/0315729 A1 | 10/2019 | Blomgren et al. |
| 2019/0330224 A1 | 10/2019 | Ghosh et al. |
| 2019/0375759 A1 | 12/2019 | Ghosh et al. |
| 2019/0381045 A1 | 12/2019 | Harriman et al. |
| 2020/0010478 A1 | 1/2020 | Ghosh et al. |
| 2020/0017519 A1 | 1/2020 | Ghosh et al. |
| 2020/0071282 A1 | 3/2020 | Blomgren et al. |
| 2020/0102323 A1 | 4/2020 | Bhat et al. |
| 2020/0148699 A1 | 5/2020 | Alexander et al. |
| 2020/0165248 A1 | 5/2020 | Blomgren et al. |
| 2020/0255418 A1 | 8/2020 | Blomgren et al. |
| 2020/0281911 A1 | 9/2020 | Dalton et al. |
| 2020/0315972 A1 | 10/2020 | Kirby et al. |
| 2021/0308136 A1 | 10/2021 | Bates et al. |
| 2022/0064181 A1 | 3/2022 | Alexander et al. |
| 2022/0204491 A1 | 6/2022 | Blomgren et al. |
| 2022/0370366 A1 | 11/2022 | Kirby et al. |

FOREIGN PATENT DOCUMENTS

| | | |
|---|---|---|
| CN | 1301162 A | 6/2001 |
| CN | 104045635 A | 9/2014 |
| CN | 104513213 A | 4/2015 |
| CN | 106146483 A | 11/2016 |
| CN | 106588804 A | 4/2017 |
| CN | 106632294 A | 5/2017 |
| CN | 106748922 A | 5/2017 |
| CN | 106955288 | 7/2017 |
| CN | 107021957 A | 8/2017 |
| CN | 107021958 A | 8/2017 |
| EP | 0640606 A1 | 3/1995 |
| EP | 1894924 A1 | 3/2008 |
| EP | 2128158 | 12/2009 |
| EP | 2189458 | 5/2010 |
| EP | 2289883 | 3/2011 |
| EP | 02351743 A1 | 8/2011 |
| EP | 3257847 | 12/2017 |
| FR | 3050112 | 10/2017 |
| JP | 62-289583 A | 12/1987 |
| JP | 02-225485 A | 9/1990 |
| JP | 08-073467 A | 3/1996 |
| JP | 09-110873 A | 4/1997 |
| JP | 2002-500666 A | 1/2002 |
| JP | 2002-541258 A | 12/2002 |
| JP | 2004-518732 A | 6/2004 |
| JP | 2007-302703 A | 11/2007 |
| JP | 2008308448 A | 12/2008 |
| JP | 2009-528389 A | 8/2009 |
| WO | WO-199417059 A1 | 8/1994 |
| WO | WO-199424095 A1 | 10/1994 |
| WO | WO 97/007119 A1 | 2/1997 |
| WO | WO-199712883 A1 | 4/1997 |
| WO | WO 97/040846 A1 | 11/1997 |
| WO | WO 98/54190 A1 | 12/1998 |
| WO | WO-200037077 A1 | 6/2000 |
| WO | WO 00/61583 A1 | 10/2000 |
| WO | WO-200077011 A1 | 12/2000 |
| WO | WO 02/064598 A1 | 8/2002 |
| WO | WO-2003015771 A1 | 2/2003 |
| WO | WO-2003015777 A1 | 2/2003 |
| WO | WO-2003016280 A1 | 2/2003 |
| WO | WO-2003016288 A1 | 2/2003 |

(56) References Cited

FOREIGN PATENT DOCUMENTS

| | | |
|---|---|---|
| WO | WO-2003080803 A2 | 10/2003 |
| WO | WO 2004/014916 A1 | 2/2004 |
| WO | WO-2004024162 A1 | 3/2004 |
| WO | WO-2004045511 A2 | 6/2004 |
| WO | WO-2004046068 A2 | 6/2004 |
| WO | WO-2004046162 A2 | 6/2004 |
| WO | WO-2004048349 A1 | 6/2004 |
| WO | WO-2004087076 A2 | 10/2004 |
| WO | WO-2005056554 A2 | 6/2005 |
| WO | WO-2005077345 A1 | 8/2005 |
| WO | WO-2005077373 A2 | 8/2005 |
| WO | WO-2005123731 A2 | 12/2005 |
| WO | WO 2006/014647 A2 | 2/2006 |
| WO | WO-2006101052 A1 | 9/2006 |
| WO | WO-2007070796 A1 | 6/2007 |
| WO | WO-2007076260 A2 | 7/2007 |
| WO | WO-2007092751 A2 | 8/2007 |
| WO | WO-2007095174 A2 | 8/2007 |
| WO | WO 2007/103776 A2 | 9/2007 |
| WO | WO-2007110237 | 10/2007 |
| WO | WO-2007140174 A2 | 12/2007 |
| WO | WO-2007140183 A1 | 12/2007 |
| WO | WO-2007140200 | 12/2007 |
| WO | WO-2008002573 A2 | 1/2008 |
| WO | WO-2008025539 A1 | 3/2008 |
| WO | WO-2008025540 A1 | 3/2008 |
| WO | WO-2008051942 A2 | 5/2008 |
| WO | WO-2008073825 A1 | 6/2008 |
| WO | WO-2008097235 A1 | 8/2008 |
| WO | WO 2008/143262 A1 | 11/2008 |
| WO | WO-2008155054 A1 | 12/2008 |
| WO | WO-2008157270 A1 | 12/2008 |
| WO | WO-2009005998 A1 | 1/2009 |
| WO | WO-2009012125 A1 | 1/2009 |
| WO | WO 2009/081197 | 7/2009 |
| WO | WO-2009127321 A1 | 10/2009 |
| WO | WO-2009149795 A2 | 12/2009 |
| WO | WO-2010034649 A1 | 4/2010 |
| WO | WO-2010034657 A1 | 4/2010 |
| WO | WO-2010036362 A1 | 4/2010 |
| WO | WO-2010052253 | 5/2010 |
| WO | WO-2010093191 A2 | 8/2010 |
| WO | WO 2011/020615 A1 | 2/2011 |
| WO | WO 2011/080277 A1 | 7/2011 |
| WO | WO-2011109059 A1 | 9/2011 |
| WO | WO-2012076063 | 6/2012 |
| WO | WO-2012087519 A1 | 6/2012 |
| WO | WO-2012087521 A1 | 6/2012 |
| WO | WO 2012/090219 | 7/2012 |
| WO | WO-2013001030 | 1/2013 |
| WO | WO-2013007387 | 1/2013 |
| WO | WO-2013037482 A1 | 3/2013 |
| WO | WO 2013/071169 | 5/2013 |
| WO | WO-2013192097 A1 | 12/2013 |
| WO | WO 2014/174524 | 10/2014 |
| WO | WO 2014/182943 | 11/2014 |
| WO | WO 2014/182950 | 11/2014 |
| WO | WO-2014181287 A1 | 11/2014 |
| WO | WO-2014184271 A1 | 11/2014 |
| WO | WO 2015/007451 | 1/2015 |
| WO | WO-2015017813 A2 | 2/2015 |
| WO | WO-2015036442 A1 | 3/2015 |
| WO | WO-2015065983 A1 | 5/2015 |
| WO | WO-2015069666 A1 | 5/2015 |
| WO | WO-2015116856 A2 | 8/2015 |
| WO | WO-2015138969 A1 | 9/2015 |
| WO | WO-2015138986 A1 | 9/2015 |
| WO | WO-2015162244 A1 | 10/2015 |
| WO | WO-2015162538 A1 | 10/2015 |
| WO | WO-2015165960 A1 | 11/2015 |
| WO | WO-2015181275 A1 | 12/2015 |
| WO | WO 2016/046311 | 3/2016 |
| WO | WO-2016055441 A1 | 4/2016 |
| WO | WO-2016073767 A1 | 5/2016 |
| WO | WO-2016081918 A1 | 5/2016 |
| WO | WO 2016/096115 A1 | 6/2016 |
| WO | WO 2016/096116 A1 | 6/2016 |
| WO | WO-2016086115 A1 | 6/2016 |
| WO | WO-2016086134 A1 | 6/2016 |
| WO | WO-2016086169 A1 | 6/2016 |
| WO | WO-2016086218 A1 | 6/2016 |
| WO | WO-2016112305 A1 | 7/2016 |
| WO | WO-2017011466 A1 | 1/2017 |
| WO | WO 2017/075056 | 5/2017 |
| WO | WO 2017/091600 | 6/2017 |
| WO | WO 2017/091602 | 6/2017 |
| WO | WO-2017096130 A1 | 6/2017 |
| WO | WO-2017097870 A1 | 6/2017 |
| WO | WO-2017117687 A1 | 7/2017 |
| WO | WO-2017118294 A1 | 7/2017 |
| WO | WO-2017118762 A1 | 7/2017 |
| WO | WO-2017122209 A2 | 7/2017 |
| WO | WO 2017/128896 A1 | 8/2017 |
| WO | WO-2017133521 A1 | 8/2017 |
| WO | WO-2017147047 A1 | 8/2017 |
| WO | WO-2017151816 | 9/2017 |
| WO | WO-2017162211 A1 | 9/2017 |
| WO | WO-2017/218330 | 12/2017 |
| WO | WO-2017210526 A1 | 12/2017 |
| WO | WO-2017216727 | 12/2017 |
| WO | WO-2017218337 | 12/2017 |
| WO | WO-2018024224 A1 | 2/2018 |
| WO | WO-2018039384 A1 | 3/2018 |
| WO | WO-2018039386 A1 | 3/2018 |
| WO | WO-2018059314 A1 | 4/2018 |
| WO | WO-2018060075 A1 | 4/2018 |
| WO | WO-2018075207 A1 | 4/2018 |
| WO | WO-2018075650 | 4/2018 |
| WO | WO-2018087599 A1 | 5/2018 |
| WO | WO-2018089212 A1 | 5/2018 |
| WO | WO 2018/133858 | 7/2018 |
| WO | WO 2018/191393 A1 | 10/2018 |
| WO | WO-2018190643 | 10/2018 |
| WO | WO-2019023245 | 1/2019 |
| WO | WO 2019/066467 | 4/2019 |
| WO | WO-2019071216 | 4/2019 |
| WO | WO-2020150136 | 7/2020 |
| WO | WO-2020172075 | 8/2020 |
| WO | WO-2020185686 | 9/2020 |

OTHER PUBLICATIONS

Akwabi-Ameyaw et al., (2009) "FXR agonist activity of conformationally constrained analogs of GW 4064", Bioorganic & Medicinal Chemistry Letters 19: 4733-4739.

Ali et al. ("Recent advances in the development of farnesoid X receptor agonists." Annals of Translational Medicine (2015); 3 (1): May 1-May 16) (Year: 2015).

Alasmael et al., (2014) "The regulatory role of Farsenoid X Receptor on Matrix Metalloproteinases-2 and -9 in advanced Breast Cancer", The European Association for Cancer Research Conference Series on Goodbye Flat Biology: 3D Models and the Tumour Microenvironment (Abstract).

Alrashid et al,. (2007) "FXR plays a key role in the anti-proliferative and apoptotic responses of bile acids in coloncarcinoma cell lines", 98th Annual Meeting of the American Association for Cancer Research, (Abstract).

Alvarez et al., "Reduced hepatic expression of Farsenoid X Receptor in hereditary cholestasis associated to mutation in ATP8B1", Human Molecular Genetics, 13(20): 2451-2460, 2004.

Amiri-Kordestani et al. JNCI J Natl Cancer Inst. vol. 104, Issue 8. (2012): 2 pages (Year: 2012).

Ananthanarayanan et al., "Human Bile Salt Export Pump Promoter is Transactivated by the Farsenoid X Receptor-Bile Acid Receptor", The Journal of Biological Chemistry, 276(31): 28857-28865, Aug. 3, 2001.

Andreone et al., (2014) "The FXR Agonist Obeticholic Acid (OCA) Improves Liver Biochemistry Parameters Correlated With Clinical Benefit Across a Range of Patient Characteristics", 65th Annual Meeting and Postgraduate Course of the American Association for the Study of Liver Diseases (AASLD), (Abstract).

(56) References Cited

OTHER PUBLICATIONS

Aparecida et al., (2012) "Alcoholic liver steatosis in mice is aggravated by low-protein diet and reversed by FXR agonist", 1st Conference on Metabolism, Diet and Disease (Abstract).
Aranda et al., "Nuclear Hormone Receptors and Gene Expression", Physiological Reviews 81(3): 1269-1304, Jul. 2001.
Auwerx, (2006) "Turning Up the Heat with Bile Acids", Nuclear Receptors: Steroid Sisters (X4), (Abstract).
Baghdasaryan et al., (2010) "Therapeutic Effects of FXR and TGR5 Activation in the MDR2 (ABCB4)Mouse Model of Sclerosing Cholangitis", 45th Annual Meeting of the European Association for the Study of the Liver (EASL), (Abstract).
Baghdasaryan et al., (2010) "Therapeutic Targeting of Nuclear and Membrane Bile Acid Receptors in a Mouse Model of Chronic Cholestasis", 61st Annual Meeting of the American Association for the Study of Liver Diseases (AASLD), (Abstract).
Baghdasaryan et al., (2011) "FXR but not Tgr5 activation stimulates HCO3—rich bile secretion and ameliorates liver damage in Mdr2−/− (Abcb4−/−) mouse model of chronic liver injury", 62nd Annual Meeting of the American Association for the Study of Liver Diseases (AASLD), (Abstract).
Balasubramaniyan et al., (2005) "Human Organic Solute Transporter Alpha (OST-ALPHA) is Transactivated by FXR, HNF-4 Alpha and FTF-LRH-1: Implications for Basolateral Bile Acid Transport in Human Liver", 56th Annual Meeting of the American Association for the Study of Liver Diseases (AASLD), (Abstract).
Ballatori et al., (2010) "Ost alpha-Ost beta: A key membrane transporter of bile acids and conjugated steroids", Front Biosci 14: 2829-2844.
Staels et al. (2004) "Perspective targets in the treatment of the metabolic syndrome", 13th European Congress on Obesity (European Association for the Study of Obesity, (Abstract).
Bass et al., (2011) "Conformationally constrained Farsenoid X Receptor (FXR) agonists: Heteroaryl replacements of the naphthalene", Bioorganic & Medicinal Chemistry Letters 21: 1206-1213.
Bechmann et al., (2011) "Free fatty acids repress SHP activation and adiponectin counteracts bile acid induced liver injury: New target options for NASH treatment?", 62nd Annual Meeting of the American Association for the Study of Liver Diseases (AASLD), (Abstract).
Beth et al., "Soy Lipid-Derived Phytosterols are FXR Antagonists-Potential Role in Total Parenteral Nutrition-Associated Cholestasis (TPNAC)", Digestive Disease Week 2004: American Association for the Study of Liver Diseases, American Gastroenterological Association, American Society for Gastrointestinal Endoscopy, Society for Surgery of the Alimentary Tract, (Abstract).
Beuers et al., (2014) "FXR Agonist Obeticholic Acid: Pruritus, A Common Side Effect Ameliorated by Dose Titration", 65th Annual Meeting and Postgraduate Course of the American Association for the Study of Liver Diseases (AASLD), (Abstract).
Bianchi et al., (2011) "Farnesoid-X-receptor (FXR) agonist INT-747 restores hepatic DDAH activity after ischemia-reperfusion injury", 35° Congresso Nazionale della Società Italiana di Farmacologia (SIF)-35th National Congress of the Italian Society of Pharmacology, (Abstract).
Bilz et al., "Activation of the Farsenoid X Receptor improves lipid metabolism in combined hyperlipidemic hamsters", Am. J. Physiol. Endocrinol. Metab., 290(4) E716-722, 2006, doi: 10.1152-aipendo. 00355.2005.
Boesjes et al., (2014) "Hepatic Farnesoid X-Receptor Isoforms a2 and a4 Differentially Modulate Bile Salt and Lipoprotein Metabolism in Mice", Plos One 9: 1-19.
Bowlus et al., (2014) "Obeticholic Acid in PBC Patients: The Utility of Titration Based on Therapeutic Response and Tolerability", 65th Annual Meeting and Postgraduate Course of the American Association for the Study of Liver Diseases (AASLD), (Abstract).
Brzozowski et al., "Molecular basis of agonism and antagonism in the oestrogen receptor", Nature, 389:753-758, Oct. 16, 1997.
Buttar et al., (2007) "Role of Farnesoid-X-receptor in Esophageal Carcinogenesis" Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Cai et al., "FXR: a target for cholestatic syndromes?", Expert Opin. Ther. Targets, 10(3): 409-421, 2006.
Cariou et al., "The Farsenoid X Receptor Modulates Adiposity and Peripheral Insulin Sensitivity in Mice", The Journal of Biological Chemistry, 28, 11039-11049, Apr. 21, 2006.
Cariou et al., (2005) "Farsenoid X Receptor (FXR) regulates peripheral insulin sensitivity", 41st Annual Meeting of the European Association for the Study of Diabetes (EASD), (Abstract).
Cha et al., (2009) "Farsenoid X Receptor (FXR) Agonist Improves Insulin Resistance and Ameliorates Diabetic Nephropathy in db-db Mice", 42nd Annual Meeting and Exposition of the American Society of Nephrology (ASN), (Abstract).
Changming et al., (2009) "Ileal bile acid binding protein mediates the chemopreventative effect of ursodeoxycholic acid by activating nuclear receptor FXR in colorectal cancer cells", 100th Annual Meeting of the American Association for Cancer Research (AACR), (Abstract).
Chen et al., "Progressive Familial Intrahepatic Cholestasis: Type I, Is Associated With Decreased Farsenoid X Receptor Activity", Gastroenterology, 126, 756-764, Mar. 2004.
Cheng et al., (2011) "Farsenoid X Receptor (FXR) controls expression of Fibroblast Growth Factor 21 (FGF21) in liver cells", 4th International Congress on Prediabetes and the Metabolic Syndrome, (Abstract).
Chennamsetty et al., (2010) "Role of Farsenoid X Receptor Agonists in the In Vivo and In Vitro Expression of Apolipoprotein(a)", 78th European Atherosclerosis Society Congress (EAS), (Abstract).
Chiang et al., (2004) "Mechanisms of bile acid inhibition of genes in bile acid synthesis", Falk Symposium No. 141, Bile Acids and Cholesterol Metabolism and its Therapeutical Implications, (Abstract).
Chignard et al., (2003) "The VILP receptor VPAC-1 in highly expressed and regulated by FXR and RXR alpha nuclear receptors in the human gallbladder epithelium", 54th Annual Meeting of the American Association for the Study of Liver Diseases (AASLD), (Abstract).
Cho et al., (2011) "Guggulsterone Inhibits LXRa Mediated SREBP-1C-Dependent Hepatic Steatosis through PKC Dependent Pathway", 46th Annual Meeting of the European Association for the Study of the Liver (EASL), (Abstract).
Chouinard et al., (2007) "Bile Acid 7a-Hydroxylase and 12B-Hydroxylase Indices Convey Target Pharmacology, Predict Preclinical Endpoint Efficacy and Offer Utility as Clinical Translational Markers of FXR Agonist Activity", Nuclear Receptors and Metabolism (Z1) held jointly with Metabolic Syndrome and Cardiovascular Risk (Z2), (Abstract).
Chu et al., (2013) "Bile Acids Induce COX-2 Expression in Human Esophagus via Activation of Farsenoid X Receptor (FXR) and Nf?B", 54th Annual Meeting at Digestive Disease Week (DDW 2013): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Claudel et al., (2005) "Constitutive Androstane Receptor Negatively Regulates Human Apolipoprotein A-1 Expression", 78th Annual Scientific Sessions of the American Heart Association (AHA), (Abstract).
Claudel et al., "The Farsenoid X Receptor: A Molecular Link Between Bile Acid and Lipid and Glucose Metabolism", Arteriosclerosis, Thrombosis, and Vascular Biology, 25, 2020-2031, 2005, obtained from URL=http:--atvb.ahaioumals.org, download date Jan. 19, 2012.
Cilofexor. Probechem. Retrieved Jun. 5, 2018. http://www.probechem.com/products_Cilofexor.aspx.
Cortés et al., (2005) "Recombinant Adenovirus-Mediated Functional Expression and Heterodimeric Nuclear Receptor-Dependent Regulation Of Syndecan-1 in the Murine Liver: Implications in Cholesterol Metabolism", Digestive Disease Week 2005 (DDW): American Association for the Study of Liver Diseases, American

(56) References Cited

OTHER PUBLICATIONS

Gastroenterological Association, American Society for Gastrointestinal Endoscopy, Society for Surgery of the Alimentary Tract, (Abstract).
D'Amore et al., (2014) "Design, Synthesis, and Biological Evaluation of Potent Dual Agonists of Nuclear and Membrane Bile Acid Receptors", Journal of Medicinal Chemistry 57: 937-954.
Das et al., (2007) "Farsenoid X Receptor Dependent Regulation of MMP9 in Blood Outgrowth Endothelial Cells Contributes to Cell Migration and Homing Through A Pathway involving SHP and KLF repressor proteins", Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Das et al., (2007) "FXR bile acid receptor activates focal adhesion kinase and stress fiber-mediated motility in endothelial cells", 58th Annual Meeting of the American Association for the Study of Liver Diseases (AASLD), (Abstract).
Das et al., (2009) "FXR Promotes Endothelial Cell Motility through Reciprocal Regulation of FAK and MMP-9", 2009 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), and the American Society for Pharmacology and Experimental Therapeutics (ASPET), (Abstract).
De Oliveira et al., (2012) "Bile acid receptor agonists INT-747 and INT-777 decrease estrogen deficiency-related postmenopausal obesity and hepatic steatosis", 63rd Annual Meeting and Postgraduate Course of the American Association for the Study of Liver Diseases (AASLD), (Abstract).
Demars et al., (2005) "Farnesoid-X-receptor and carcinogenesis in Barrett's esophagus", 96th American Association for Cancer Research Annual Meeting, (Abstract).
Deuschle et al., (2012) "FXR directly controls the tumor suppressor NDRG2 and FXR agonists reduce tumor growth and metastasis in an orthotopic xenograft mouse model", 47th Annual Meeting of the European Association for the Study of the Liver (EASL), (Abstract).
Deuschle et al., (2014) "The nuclear bile acid receptor FXR controls the liver derived tumor suppressor histidine-rich glycoprotein", International Journal of Cancer, 00: 00-00.
Dodson et al., (2005) "Concerted Control of Lipids and Insulin Sensitization by FXR", 87th Annual Meeting of the Endocrine Society (ENDO), (Abstract).
Dodson et al., (2007) "Concerted control of insulin sensitization through lipid and carbohydrate metabolism by FXR", Nuclear Receptors and Metabolism (Z1) held jointly with Metabolic Syndrome and Cardiovascular Risk (Z2), (Abstract).
Doggrell, "New targets in and potential treatments for cholesterol gallstone disease", Current Opinion in Investigational Drugs 7(4): 344-348, 2006.
Dossa et al., (2014) "Bile Acids Differentially Control Intestinal Cell Proliferation via Src Kinase", 2014 Clinical Congress of the American College of Surgeons (ACS), (Abstract).
Dossa et al., (2014) "Intestinal bile acids differentially control intestinal cell proliferation", 34th Annual Meeting of the Surgical Infection Society (SIS), (Abstract).
Duran-Sandoval et al., "Potential regulatory role of the Farsenoid X Receptor in the metabolic syndrome", Biochimie 87:93-98, 2005.
Edwards et al., (2007) "FXR Modulates Lipid and Glucose Metabolism", Nuclear Receptors and Metabolism (Z1) held jointly with Metabolic Syndrome and Cardiovascular Risk (Z2), (Abstract).
Eloranta et al., (2004) "Coordinate transcriptional regulation of bile acid homeostasis and drug metabolism", Archives of Biochemistry and Biophysics 433: 397-412.
Eloranta et al., (2005) "Human organic solute transporter-alpha (OSTalpha) and -beta (OSTbeta) genes are transactivated by the nuclear bile acid receptor-Farsenoid X Receptor (FXR)", 56th Annual Meeting of the American Association for the Study of Liver Diseases (AASLD), (Abstract).
European Search Report for EP11005722, completed Sep. 13, 2011, 2 pages.
European Search Report for EP15002478.4, completed Nov. 17, 2015, 8 pages.
Evans, "The Nuclear Receptor Superfamily: A Rosetta Stone for Physiology", Molecular Endocrinology 19(6): 1429-1438, Jun. 2005.
Evans et al., (2007) "Activation of Farsenoid X Receptor (FXR) in the treatment of dyslipidemia", Nuclear Receptors and Metabolism (Z1) held jointly with Metabolic Syndrome and Cardiovascular Risk (Z2), (Abstract).
Evans et al., (2007) "Activation of Farsenoid X Receptor (FXR) protects against diet-induced dyslipidemia", 76th European Atherosclerosis Society Congress (EAS), (Abstract).
Falk et al., (2006) "Primary biliary cirrhosis: From ursodeoxycholic acid towards targeting strategies for therapy", Falk Symposium No. 155: XIX International Bile Acid Meeting—Bile Acids: Biological Actions and Clinical Relevance (Abstract).
Fang et al., (2008) "The acetylase p300 and deacetylase SIRT1 are critical in vivo FXR cofactors in regulation of liver metabolism", 2008 Nuclear Receptors: Orphan Brothers (Z1), (Abstract).
Feng et al., (2009) "Identification of an N-oxide pyridine GW4064 analog as a potent FXR agonist", Bioorganic & Medicinal Chemistry Letters 19: 2595-2598.
Figge et al., "Hepatic Overexpression of Murine Abcb11 Increases Hepatobiliary Lipid Secretion and Reduces Hepatic Steatosis", The Journal of Biological Chemistry 279(4): 2790-2799, Jan. 23, 2004.
Fiorucci et al., "Protective Effects of 6-Ethyl Chenodeoxycholic Acid, a Farsenoid X Receptor Ligand, in Estrogen-Induced Cholestasis", The Journal of Pharmacology and Experimental Therapeutics 313(2): 604-612,2005.
Fiorucci et al., "The Nuclear Receptor SHP Mediates Inhibition of Hepatic Stellate Cells by FXR and Protects Against Liver Fibrosis", Gastroenterology 127(5): 1497-1512, Nov. 2004.
Fiorucci et al., (2003) "The FXR-agonist, 6-Ethyl-Chenodeoxycholic Acid (6-ECDCA), protects against estrogen-induced cholestasis in rats", Pellicciari R Digestive Disease Week 2003 (DDW): American Association for the Study of Liver Diseases, American astroenterological Association, American Society for Gastrointestinal Endoscopy, Society for Surgery of the Alimentary Tract (Abstract).
Fiorucci et al., (2010) "The Bile Acid Sensor FXR Modulates Hydrogen Sulfide Generation in the Gastric Mucosa and Protects Against Injury Caused by Aspirin", Digestive Disease Week 2010 (DDW), (Abstract).
Fiorucci et al., (2014) "Targeting FXR in cholestasis: hype or hope", Expert Opinion 18 (12).
Fiorucci et al., (2005), "A Farsenoid X Receptor-Small Heterodimer Partner Regulatory Cascade Modulates Tissue Metalloproteinase Inhibitor-1 and Matrix Metalloprotease Expression in Hepatic Stellate Cells and Promotes Resolution of Liver Fibrosis", TheJournal of Pharmacology and Experimental Therapeutics, 314: 584-595.
Flatt et al., (2005) "SAR of highly potent full-range modulators of the Farsenoid X Receptor", 229th National Meeting of the American Chemical Society (Abstract).
Flesch et al., (2014) "Screening, synthesis and characterization of novel ligands for Farsenoid X Receptor (FXR)", 2014 Annual Meeting on Trends and Perspectives in Pharmaceutical Sciences (DPhG ) Annual Meeting of the German Pharmaceutical Society (DPhG), (Abstract).
Flesch et al., (2014) "Screening, Synthesis and Characterization of Novel Ligands for Farsenoid X Receptor (FXR)", 23rd International Symposium on Medicinal Chemistry (ISMC) held Jointly with the European Federation for Medicinal Chemistry (EFMC), (Abstract).
Flesch et al., (2015) "Fragmentation of GW4064 led to a highly potent partial Farsenoid X Receptor agonist with improved drug-like properties", Bioorganic & Medicinal Chemistry 13: 3490-8.
Forman et al., "Identification of a Nuclear Receptor That is Activated by Farnesol Metabolites", Cell 81:687-693, Jun. 2, 1995.
Fuchs et al., (2012) "Changes in hepatic bile acid composition protect BSEP (ABCB11) KO mice from hepatic inflammation in methionine choline deficient (MCD)-diet induced NASH", 63rd

(56) References Cited

OTHER PUBLICATIONS

Annual Meeting and Postgraduate Course of the American Association for the Study of Liver Diseases (AASLD), (Abstract).
Fuchs et al., (2012) "FXR is a key player in NAFLD development by controlling chop expression", 47th Annual Meeting of the European Association for the Study of the Liver (EASL), (Abstract).
Fuchs et al., (2013) "FXR controlled CHOP as novel key player in NAFLD progression", 64th Annual Meeting and Postgraduate Course of the American Association for the Study of Liver Diseases (AASLD), (Abstract).
Fuchs et al., (2014) "Intrahepatic Changes in Bile Acid Composition Protects Bsep (ABCB11) KO Mice From Hepatic Injury in Methionine Choline-Deficient Diet Induced NASH", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).
Gadaleta et al., (2009) "FXR activation represses TNFa-induced NF-?B signalling", 2009 Spring Meeting of the Dutch Society for Gastroenterology—2009 Voorjaarsvergadering Nederlandse Vereniging voor Gastroenterologie (Abstract).
Gadaleta et al., (2010) "Intestinal Bile Salt Nuclear Receptor FXR Protects From Inflammatory Bowel Disease: Potential Therapeutic Implications", Digestive Disease Week 2010 (DDW), (Abstract).
Gadaleta et al., (2011) "Farsenoid X Receptor activation inhibits inflammation and preserves the intestinal barrier in inflammatory bowel disease", Inflammatory bowel disease 60: 463-472.
Gautier et al., (2011) "Farsenoid X Receptor Activation Induces Cholesteryl Ester Transfer Protein Expression in Humans and Transgenic Mice", 12th Annual Conference on Arteriosclerosis, Thrombosis and Vascular Biology (ATVB) in collaboration with the Council on Peripheral Vascular Disease (Abstract).
Gautier et al., (2011) "Farsenoid X Receptor Activation Induces Cholesteryl Ester Transfer Protein Expression in Humans and Transgenic Mice", 79th European Atherosclerosis Society Congress (EAS), (Abstract).
Gege et al., (2014) "Knocking on FXR's Door: The "Hammerhead"-Structure Series of FXR Agonists—Amphiphilic Isoxazoles with Potent In Vitro and In Vivo Activities", Current Topics in Medicinal Chemistry 14: 1-16.
Gioiello et al., (2014) "Bile Acid Derivatives as Ligands of the Farsenoid X Receptor: Molecular Determinants for Bile Acid Binding and Receptor Modulation", Current Topics in Medicinal Chemistry 14: 2159-2174.
Giordano et al., (2010) "Activated Farsenoid X Receptor Inhibits Growth of Tamoxifen-Resistant MCF-7 Breast Cancer Cells, through Down-Regulation of HER2 Expression", 92nd Annual Meeting of the Endocrine Society (ENDO), (Abstract).
Giordano et al., (2010) "Activated Farsenoid X Receptor inhibits growth of tamoxifen-resistant breast cancer cells", 2010 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN) and the American Society for Pharmacology and Experimental Therapeutics (ASPET), (Abstract).
Giordano et al., (2014) "FXR Ligands, by Interfering with Tumor-Microenvironment Crosstalk, Inhibit Breast Tumor Growth and Progression", 2nd Joint Meeting of Pathology and Laboratory Diagnostics, 32.Congress of the Società Italiana di Patologia e Medicina Traslazionale, 64.National Congress of the Associazione Italiana di Patologia Clinica e Medicina Molecolare—32nd Congress of the Italian Society of Pathology and Translational Medicine and 64th National Congress of the Italian Association of Clinical Pathology and Molecular Medicine (Abstract).
Glastras et al., (2013) "The role of FXR in maternal obesity related renal injury in mother and offspring", 2013 Annual Scientific Meeting of the Australian Diabetes Educators Association (ADEA) and the Australian Diabetes Society (ADS), (Abstract).
Gnerre et al., (2004) "CYP3A4 and CYP3A11 are regulated by the nuclear receptor FXR and primary bile acids in cell cultures and in mice", 15th International Symposium on Microsomes and Drug Oxidations: Chemical Biology in the Postgenomic Era—New Approaches and Applications (Abstract).
Goodwin et al., "A Regulatory Cascade of the Nuclear Receptors FXR, SHP-1, and LRH-I Represses Bile Acid Biosynthesis", Molecular Cell 6: 517-526, Sep. 2000.
Grefhorst et al., (2004) "The role of nuclear hormone receptors in hepatic insulin resistance", 3rd Dutch Endo-Neuro-Psycho Meeting 2004 (Abstract).
Guan et al., (2008) "Nuclear receptors and metabolic syndrome", 2008 Beijing Conference of Physiological Sciences jointly supported by the American Physiological Society, Australian Physiological Society, Canadian Physiological Society, Chinese Association for Physiological Sciences, and the Physiological Society (UK), (Abstract).
Guo-Ning et al., (2014) "Synthesis and Bioactivity of Chalcones and Related Compounds as Farsenoid X Receptor (FXR) Antagonists", 34th National Medicinal Chemistry Symposium (NMCS), (Abstract).
Habegger et al., (2012) "Fibroblast Growth Factor 21 and Farsenoid X Receptor Mediate Chronic Glucagon Action", 72nd Annual Meeting and Scientific Sessions of the American Diabetes Association (ADA), (Abstract).
Hambruch, et al., (2013) "FXR agonist Px-102 improves hepatic steatosis in NAFLD mouse models", Phenex (Poster).
Hambruch et al., (2012) "Synthetic Farsenoid X Receptor agonist PX20606 demonstrates anti-atherosclerotic effects and lowers cholesterol in HDL2 but not in HDL3 subfractions", Poster.
Hambruch et al., (2013) "FXR Agonist Px-102 Improves Hepatic Steatosis in NAFLD Rodent Models", 23rd Conference of the Asia Pacific Associaton for the Study of the Liver (APASL 2013): Transforming Science to Clinical Practice (Abstract).
Hanniman et al., "Loss of functional Farsenoid X Receptor increases atherosclerotic lesions in apolipoprotein E-deficient mice", Journal of Lipid Research, 46:2595-2604, 2005.
Hansen et al., (2014) "The FXR agonist obeticholic acid improves alkaline phosphatase-bilirubin response criterion associated with transplant-free survival in primary biliary cirrhosis", 2014 European Association for the Study of the Liver (EASL) Monothematic Conference: Primary Biliary Cirrhosis (PBC), (Abstract).
Harnish, (2007) "A Synthetic Farsenoid X Receptor Agonist Protects Against Diet-Induced Dyslipidemia", 80th Annual Scientific Sessions of the American Heart Association (AHA), (Abstract).
Harnish et al., (2007) "A synthetic Farsenoid X Receptor (FXR) agonist protects against diet-induced dyslipidemia", 16th International Symposium on Drugs Affecting Lipid Metabolism (Abstract).
Harnish et al., (2007) "The Farsenoid X Receptor (FXR) Antagonizes Oxidized LDL Receptor, LOX-1, Activation", 80th Annual Scientific Sessions of the American Heart Association (AHA), (Abstract).
Harriman et al. ("Acetyl-CoA carboxylase inhibition by N D-630 reduces hepatic steatosis, improves insulin sensitivity, and modulates dyslipidemia in rats." Proc Natl Acad Sci US A .; Published online (Mar. 14, 2016); 113(13): E1796-E 1805) (Year: 2016).
Hartman et al., (2007) "Farsenoid X Receptor (FXR) Regulates RECK Expression", 58th Annual Meeting of the American Association for the Study of Liver Diseases (AASLD), (Abstract).
Hawksworth, (2010) "Hepatic transporters—Regulation, induction and potential for drug-drug interactions", 8th Southeast European Congress on Xenobiotic Metabolism and Toxicity (XEMET 2010), (Abstract).
He et al., "Downregulation of Endothelin-1 by Farsenoid X Receptor in Vascular Endothelial Cells", Circulation Research 98(2): 192-199,2006, plus online supplement, obtained from URL=http:--circres.ahaioumals.org, download date Jun. 11, 2012, 14pages.
Heery et al., "A signature motif in transcriptional co-activators mediates binding to nuclear receptors", Nature 387:733-736, Jun. 12, 1997.

(56) References Cited

OTHER PUBLICATIONS

Heinzel et al., "A complex containing N-COR, mSin3 and histone deacetylase mediates transcriptional repression", Nature, 387:43-48, May 1, 1997.
Henry et al., (2009) "Farsenoid X ReceptorAgonists: A New Therapeutic Class for Diabetes and Fatty Liver Disease? The First FXR Therapeutic Study in Diabetes", 69th Annual Meeting and Scientific Sessions of the American Diabetes Association (ADA), (Abstract).
Hirschfield et al., (2014) "Efficacy of Obeticholic Acid in Patients with Primary Biliary Cirrhosis and Inadequate Response to Ursodeoxycholic Acid", Gastroenterology 148: 751-761.
Hoegenauer et al., (2014) "G-Protein-coupled Bile Acid Receptor 1 (GPBAR1,TGR5) agonists reduce the production of proinflammatory cytokines and stabilize the 57alternative macrophage phenotype", Journal of Medicinal Chemistry 57: 10343-54.
Holt et al., "Definition of a novel growth factor-dependent signal cascade for the suppression of bile acid biosynthesis", Genes & Development 17:1581-1591, 2003.
Horth et al., (2009) "Influence of bile acids on stimulus-secretion coupling in pancreatic beta cells", Frühjahrstagung der Deutschen Gesellschaft für Experimentelle und Klinische Pharmakologie und Toxikologie—50th Spring Meeting of the German Society for Experimental and Clinical Pharmacology and Toxicology (Abstract).
Horth et al., (2010) "The function of murine pancreatic beta cells is affected by bile acids", Frühjahrstagung der Deutschen Gesellschaft für Experimentelle und Klinische Pharmakologie und Toxikologie—51st Spring Meeting of the German Society for Experimental and Clinical Pharmacology and Toxicology (Abstract).
Horth et al., (2011) "Bile acids affect the function of murine pancreatic beta cells", 47th Annual Meeting of the European Association for the Study of Diabetes (EASD), (Abstract).
Horth et al., (2011) "Link between the nuclear farnesoid receptor and KATP channel activity in beta-cells", 90th Annual Meeting of the German Physiological Society-Deutsche Physiologische Gesellschaft (DPG), (Abstract).
Houssin et al., (2010) "The FXR activators, chenodeoxycholic acid and GW4064 inhibit the proliferation of prostate cancer LNCaP and LAPC-4 cells", 2010 Nuclear Receptors: Signaling, Gene Regulation and Cancer (X7), (Abstract).
Howarth et al., (2007) "Is the Farsenoid X Receptor in Japanese medaka (*Oryzias latipes*) a target for exogenous compounds?", 46th Annual Meeting of the Society of Toxicology (Abstract).
Hsu et al., (2014) "Quantitative Profiling of Environmental Chemicals and Drugs for Farsenoid X Receptor Activity", 53rd Annual Meeting of the Society of Toxicology (SOT 2014), (Abstract).
Huang et al., "Farsenoid X Receptor Activates Transcription of the Phospholipid Pump MDR3", The Journal of Biological Chemistry 278(51): 51085-51090. Dec. 19, 2003.
Huang et al., (2014) "Recent Advances in Non-Steroidal FXR Antagonists Development for Therapeutic Applications", Current Topics in Medicinal Chemistry 14: 2175-2187.
Huang et al., "Nuclear Receptor-Dependent Bile Acid Signaling Is Required for Normal Liver Regeneration", Science 312:233-236, Apr. 14, 2006.
Hulzebos et al., (2005) "Pharmacological FXR Activation and the Enterohepatic Circulation of Bile Salts in Rats: Inhibition of Cholate Synthesis Rate and Reduced Cholate Pool Size", 115th Annual Meeting of the American Pediatric Society and 74th Annual Meeting of the Society for Pediatric Research together with the American Society of Pediatric Hematology-Oncology (ASPHO), the American Society of Pediatric Nephrology, the Lawson Wilkins Pediatric Endocrine Society and the Pediatric Infectious Disease Society (Abstract).
Hwang et al., (2004) "The Cellular Distribution of FXR and RXRa Expression in Developing Rat Ileal Mucosa", Digestive Disease Week 2004 (DDW): American Association for the Study of Liver Diseases, American Gastroenterological Association, American Society for Gastrointestinal Endoscopy, Society for Surgery of the Alimentary Tract (Abstract).

Idelman et al., (2012) "Activation of the farnesoid X-receptor (FXR) suppresses cyclin D1 expression and decreases proliferation of colon and breast cancer cells", 63rd Annual Meeting and Postgraduate Course of the American Association for the Study of Liver Diseases (AASLD), (Abstract).
Idelman et al., (2014) "Activation of the farnesoid X-receptor suppresses cyclin D1 expression and decreases proliferation", 2014 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), Chinese Pharmacological Society (CPS) and the American Society for Pharmacology and Experimental Therapeutics (ASPET), (Abstract).
Ikpa et al., (2014) "Impaired FXR Signaling in the CF Intestine", 28th Annual North American Cystic Fibrosis Conference (NACFC), (Abstract).
Inagaki et al., (2004) "Bile acid receptor, FXR, regulates host defense in intestine", 18th International Bile Acid Meeting: Bile Acid and Cholesterol Metabolism and its Therapeutic Implications (Abstract).
Inagaki et al., (2004) "Bile acid receptor, FXR, regulates host defense in intestine", Falk Symposium No. 141 Bile Acids and Cholesterol Metabolism and its Therapeutical Implications (Abstract).
Inagaki et al., (2006) "Regulation of Mucosal Defense in Intestine by the Nuclear Bile Acid Receptor", Nuclear Receptors: Orphan Brothers (X3), (Abstract).
Inagaki et al., "Fibroblast growth factor 15 functions as an enterohepatic signal to regulate bile acid homeostasis", Cell Metabolism, 2, 217-225, Oct. 2005.
Inagaki et al., "Regulation of antibacterial defense in the small intestine by the nuclear bile acid receptor", Proc. Natl. Acad. Sci USA, 103, 3920-3905, 2006, doi:10.1073-pnas.0509592103.
International Search Report and Written Opinion dated Jun. 19, 2018 for PCT/US2018/024345. 13 pages.
Ishii, (2010) "Bile acids and their pathophysiological role in metabolic disorders", 83rd Annual Meeting of the Japanese Society for Pharmacology (Abstract).
Jae et al., (2009) "Antidiabetic effects of novel ligands for the orphan nuclear receptor LRH-1", 2009 Type 2 Diabetes and Insulin Resistance (J3), (Abstract).
Jain et al., (2009) "Enteral bile acids improve TPN related cholestasis and gut mucosal atrophy: potential role of FXR and FGF19", 22nd Annual Meeting of the North American Society for Pediatric Gastroenterology, Hepatology and Nutrition (NASPGHAN), (Abstract).
Jiang et al., (2006) "Protective Role of FXR Activation in Diabetic Nephropathy", 39th Annual Meeting and Exposition of the American Society of Nephrology (ASN): Renal Week 2006 (Abstract).
Jiang et al., (2007) "FXR Modulates Renal Lipid Metabolism, Fibrosis, and Inflammation", 40th Annual Meeting and Exposition of the American Society of Nephrology (ASN): Renal Week 2007 (Abstract).
Jiang et al., (2009) "A Novel Bile Acid Receptor Agonist Prevents Diabetic Nephropathy", 42nd Annual Meeting and Exposition of the American Society of Nephrology (ASN): Renal Week 2009 (Abstract).
Jiang et al., (2014) "Intestinal Farsenoid X Receptor signaling promotes nonalcoholic fatty liver disease", The Journal of Clinical Investigation 125: 386-402.
Johansson, (2004) "Effects of the thyroid receptor-beta agonist, GC-1 , on bile acid in intact male mice", 18th International Bile Acid Meeting: Bile Acid and Cholesterol Metabolism and its Therapeutic Implications (Abstract).
John et al., (2004) "Mechanisms of Bile Acid Inhibition of Genes in Bile Acid Synthesis", 18th International Bile Acid Meeting: Bile Acid and Cholesterol Metabolism and its Therapeutic Implications (Abstract).
Johnson et al. (Relationships between drug activity and NCI preclinical in vitro and in vivo models and early clinical trials; British Journal of Cancer; (2001) 84 (10), 1424-1431) (Year: 2001).
Johnston et al., (2013) "A New Therapy for Chronic Diarrhea? a Proof of Concept Study of the FXR Agonist Obeticholic Acid in Patients With Primary Bile Acid Diarrhea", 54th Annual Meeting at Digestive Disease Week (DDW 2013 ): American Association for

(56) References Cited

OTHER PUBLICATIONS the Study of Liver Diseases (AASLD), American Gastroenterological Association (AGA), American Society for Gastrointestinal Endoscopy (ASGE), Society for Surgery of the Alimentary Tract (SSAT), (Abstract).

Journe et al., "Association between Farsenoid X Receptor expression and cell proliferation in estrogen receptor-positive luminal-like breast cancer from postmenopausal patients", Breast Cancer Res. Treat. 115(3): 523-534, 2009, doi: 10.1007-s10549-008-0094-2.

Journe et al., (2006) "Bone-Derived Lipid Stimulates MCF-7 Breast Cancer Cell Growth through Farsenoid X Receptor-Mediated Estrogen Receptor Activation", 28th Annual Meeting of the American Society for Bone and Mineral Research (ASBMR), (Abstract).

Journe et al., (2006) "Crosstalk between Farsenoid X Receptor and estrogen receptor might account for mitogenic effect of bone-derived lipids in bone metastasis from breast cancer", 6th International Meeting on Cancer Induced Bone Disease (CABS), (Abstract).

Journe et al., (2006) "Farsenoid X Receptor: a new marker of poor prognosis in luminal subtype of breast carcinomas?", 29th Annual San Antonio Breast Cancer Symposium (SABCS), (Abstract).

Journe et al., (2006) "Farnesol, an intermediate of the mevalonate pathway, stimulates MCF-7 breast cancer cell growth: evidence for a positive crosstalk between Farsenoid X Receptor and estrogen receptor", 29th Annual San Antonio Breast Cancer Symposium (SABCS), (Abstract).

Journe et al., (2007) "Activation of Farsenoid X Receptor in Breast Cancer Cell Lines by Bone-Derived Lipid", 29th Annual Meeting of the American Society for Bone and Mineral Research (ASBMR), (Abstract).

Journe et al., (2007) "Bone-derived lipids stimulate breast cancer cell growth through a crosstalk between Farsenoid X Receptor and estrogen receptor: in vitro and clinical data", 34th European Symposium on Calcified Tissues (ECTS), (Abstract).

Jung et al., (2004) "Reverse cholesterol transport in cholangiocytes is regulated by LXR", 55th Annual Meeting of the American Association for the Study of Liver Diseases (AASLD), (Abstract).

Jung et al., (2006) "PXR is a target of FXR", 16th International Symposium on Microsomes and Drug Oxidations (MDO), (Abstract).

Kainuma, M. et al., "Design, synthesis, and evaluation of non-steroidal Farsenoid X Receptor (FXR) antagonist", 2007, Bioorg. Med. Chem., 15, 2587-2600.

Kansy et al., "Physicochemical high throughput screening: parallel artificial membrane permeation assay in the description of passive absorption processes", J. Med. Chem. 41(7), 1007-1010, Mar. 26, 1998.

Kast et al., "Farnesoid X-Activated Receptor Induces Apolipoprotein C-II Transcription: a Molecular Mechanism Linking Plasma Triglyceride Levels to Bile Acids", Molecular Endocrinology, 5(10): 1720-1728, 2001.

Kast et al., "Regulation of Multidrug Resistance-associated Protein 2 (ABCC2) by the Nuclear Receptors Pregnane X Receptor, Farnesoid X-activated Receptor, and Constitutive Androstane Receptor", The Journal of Biological Chemistry, 277(4):2908-2915, 2002.

Katona et al., (2006) "Synthesis and Nuclear Receptor Agonistic-Antagonistic Profiles of Enantiomeric Bile Acids", 97th Annual Meeting and Expo of the American Oil Chemists Society Joint Symposium on Biosciences: A Global Business Forum on Fats, Oils, Surfactants, Lipids, and Related Materials (Abstract).

Kawamura et al., (2012) "Functional Analysis of the Farsenoid X Receptor in Colorectal Cancer Cells", 35th Annual Meeting of Molecular Biology Society of Japan (MBSJ), (Abstract).

Keating et al., (2009) "Farsenoid X Receptor Activation Downregulates Chloride Secretion in Colonic Epithelial Cells", Digestive Disease Week 2009 (DDW), (Abstract).

Keating et al., (2010) "Farnesoid X-receptor Agonists Inhibit Colonic Secretion In Vitro and In Vivo", Digestive Disease Week 2010 (DDW), (Abstract).

Keitel et al., (2014) "TGR5: Pathogenetic Role and-or Therapeutic Target in Fibrosing Cholangitis?", Clinic Rev Allerg Immunol 48: 218-25.

Kennie et al., (2013) "Relative Potencies of Bile Acids in Inducing Fibroblast Growth Factor 19 in the Human Ileum", 54th Annual Meeting at Digestive Disease Week (DDW 2013 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Kerr et al., (2012) "Cysteine Sulfinic Acid Decarboxylase Regulation by Bile Acids: A Role for FXR and SHP in Hepatic Taurine Metabolism", 53rd Annual Meeting at Digestive Disease Week (DDW 2012): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Kim et al., "Spontaneous hepatocarcinogenesis in Farsenoid X Receptor-null mice", Carcinogenesis 28(5): 940-946, 2007.

Kim et al., (2014) "Therapeutic Targets and Management of Non-Alcoholic Steatohepatitis", 20th Annual Meeting of the Korean Association for the Study of the Liver (KASL) and Postgraduate Course—Liver Week (Abstract).

Kir et al., (2011) "FGF19 as a Postprandial, Insulin-Independent Activator of Hepatic Protein and Glycogen Synthesis", Science 331: 1621-4.

Klaman et al., (2007) "A Potent FXR Agonist Decreases Triglyceride and Cholesterol Levels in Dyslipidemic Mice, but Does Not Lower Glycemia in Insulin Resistant Mouse Models", 67th Annual Meeting and Scientific Sessions of the American Diabetes Association (ADA), (Abstract).

Kliewer, (2006) "Coordinate Regulation of Bile Acid Homeostasis & Innate Immunity by the Nuclear Bile Acid Receptor", 88th Annual Meeting of the Endocrine Society (ENDO), (Abstract).

Komichi et al., (2004) "A Nuclear Receptor Ligand Down-Regulates Cytosolic Phospholipase A2 (cPLA2) Expression to Reduce bile Acid-Induced Cyclooxygenase 2 (COX-2) Activity in Cholangiocytes: Implication of Anti-Carcinogenic Action of Farsenoid X Receptor (FXR) Agonist", Digestive Disease Week 2004 (DDW): American Association for the Study of Liver Diseases, American Gastroenterological Association, American Society for Gastrointestinal Endoscopy, Society for Surgery of the Alimentary Tract (Abstract).

Kong et al., (2009) "Suppression of cyp7a1 gene transcription by FXR in mice is mediated through the intestineinitiated FGF15-FGFR4 pathway rather than the liver-initiated SHP-LRH1 pathway", 60th Annual Meeting of the American Association for the Study of Liver Diseases (AASLD), (Abstract).

Kong et al., (2011) "Differential Roles of Intestinal Fgf15 and Hepatic Shp in Feed-back Suppression of Cyp7a1 and Cyp8b1 Gene Transcription in Mice", 62nd Annual Meeting of the American Association for the Study of Liver Diseases (AASLD), (Abstract).

Kowdley et al., (2011) "An international study evaluating the Farsenoid X Receptor agonist obeticholic acid as monotherapy in PBC", 46th Annual Meeting of the European Association for the Study of the Liver (EASL), (Abstract).

Kowdley et al., (2014) "FXR Agonist Obeticholic Acid: Sustained Improvement in Markers of Cholestasis and Long-Term Safety in Patients with Primary Biliary Cirrhosis through 4 Years", 65th Annual Meeting and Postgraduate Course of the American Association for the Study of Liver Diseases (AASLD), (Abstract).

Kremoser et al., (2010) "FXR agonists as novel medication for metabolic syndrome and NASH", 16th World Congress of Basic and Clinical Pharmacology (WorldPharma 2010) of the International Union of Pharmacology (IUPHAR), (Abstract).

Kremoser et al., (2010) "Phenex Pharmaceuticals AG", Poster.

Kremoser et al., (2012) "FXR agonists prevent steatosis, hepatocyte death and progression of NASH towards hcc in a hypoinsulinaemic mouse model of progressive liver disease", 47th Annual Meeting of the European Association for the Study of the Liver (EASL), (Abstract).

Kremoser et al., (2012) "Synthetic FXR agonists improve liver histopathology and reduce liver tumor formation in mouse models of NASH and liver cancer", 22nd Conference of the Asian Pacific Association for the Study of the Liver (APASL), (Abstract).

(56) References Cited

OTHER PUBLICATIONS

Kumar et al., (2009) "Farsenoid X ReceptorAgonist (GW4064) Protects the Kidney from Ischemic Acute Kidney Injury", 42nd Annual Meeting and Exposition of the American Society of Nephrology (ASN): Renal Week 2009 (Abstract).
Kunne et al., (2011) "Hepatic steatosis in mice lacking hepatic cytochrome p450 activity is bile salt dependent", 62nd Annual Meeting of the American Association for the Study of Liver Diseases (AASLD), (Abstract).
Kurata et al., (2011) Pathophysiological Role of Chenodeoxycholic Acid on Hepatic Disposition of Metformin via Organic Cation Transporter 1 in Acute Cholestasis, 2011 Annual Meeting of the American Association of Pharmaceutical Scientists (AAPS), (Abstract).
Lambert et al., "The Farnesoid X-receptor is an Essential Regulator of Cholesterol Homeostasis", The Journal of Biological Chemistry, 278, 2563-2570, 2003.
Lamers et al., (2012) "Structure and Ligand-Based Identification of Novel Synthetic Ligands for Farsenoid X Receptor", 22nd Biennial International Symposium on Medicinal Chemistry (EFMC-ISMC 2012), (Abstract).
Lamers et al., (2014) "Medicinal Chemistry and Pharmacological Effects of Farsenoid X Receptor (FXR) Antagonists", Current Topics in Medicinal Chemistry 14: 2188-2205.
Lamers et al., (2014) "Pyridinol-Pyridinon Tautomerism Determining Activity at Farsenoid X Receptor (FXR): New Agonistic or Antagonistic Ligands of FXR", 23rd International Symposium on Medicinal Chemistry (ISMC) held Jointly with the European Federation for Medicinal Chemistry (EFMC), (Abstract).
Lamers et al., (2014) "Pyridinol-Pyridinon-tautomerism determining activity at Farsenoid X Receptor: new agonistic or antagonistic ligands of FXR", 2014 Annual Meeting on Trends and Perspectives in Pharmaceutical Sciences (DPhG) Annual Meeting of the German Pharmaceutical Society (DPhG), (Abstract).
Lavine et al., (2014) "Association of Hepatic Nuclear Hormone Receptor Expression Profiles with Features of Hepatic Histology in Children with Nonalcoholic Fatty Liver Disease", 65th Annual Meeting and Postgraduate Course of the American Association for the Study of Liver Diseases (AASLD), (Abstract).
Lawson, J. et al . . . "Diarylcyclobutane analogs of diethylstilbestrol", 1974, J. Med. Chem., 17, 383-386.
Leckie et al., (2009) "Modulation of the DDAH-ADMA pathway with the Farnesoid receptor (FXR) agonist INT-747 restores hepatic eNOS activity and lowers portal pressure in cirrhotic rats", 2009 Annual Meeting of the British Association for the Study of the Liver (BASL), (Abstract).
Leclercq, (2009) "Experimental therapies in NASH", 2009 European Association for the Study of Liver Special Conference: Non Alcoholic Fatty Liver Disease-Non Alcoholic Steato-Hepatitis (NAFLD-NASH) and Related Metabolic Disease (Abstract).
Lee et al., (2010) "FXR Positively Regulates Hepatic SIRT1 Levels Via MicroRNA-34a Inhibition", 92nd Annual Meeting of the Endocrine Society (ENDO), (Abstract).
Li et al., (2010) "Transgenic expression of CYP7A1 in mouse livers promotes biliary cholesterol secretion via FXRdependent induction of hepatic ABCG5 and ABCG8 expression", 61st Annual Meeting of the American Association for the Study of Liver Diseases (AASLD), (Abstract).
Li et al., (2015) "Bile acids as metabolic regulators", Curr Opin Gastroenterol 31: 000-000.
Lian et al., (2011) "Hepatoprotective effect of Farsenoid X Receptor on liver injury in systemic lupus erythematosus", 12th Annual European League Against Rheumatism (EULAR 2011), (Abstract).
Liebman et al., (2004) "PPAR-y Agonists Modulate Renal Lipid Metabolism and Prevent the Development of Glomerulosclerosis in Zucker Diabetic Fatty Rats", 37th Annual Meeting and Exposition of the American Society of Nephrology (ASN), (Abstract).
Lien et al., (2010) "Regulation of FXR transcriptional activity by AMPK", 2010 Nuclear Receptors: Signaling, Gene Regulation and Cancer (X7), (Abstract).
Lihong et al., (2006) "FXR Agonist, GW4064, Reverses Metabolic Defects in High-Fat Diet Fed Mice", 66th Annual Meeting and Scientific Sessions of the American Diabetes Association (ADA), (Abstract).
Lihong et al., American Diabetes Association (ADA) 66th annual scientific sessions, Jun. 2006, Abstract No. 856-P.
Lin, (2008) "Study of role of Farsenoid X Receptor in hepatocarcinoma cells", Biennial Shanghai—Hong Kong International Liver Congress 2008 (Abstract).
Liu et al., "Hepatoprotection by the Farsenoid X Receptor agonist GW4064 in rat models of intra- and extrahepatic cholestasis", The Journal of Clinical Investigation, 112, 1678-1687, 2003, doi: 10.1172-JCI200318945.
Liu et al., (2004) "Protection against cclinduced hepatic fibrosis by the Farsenoid X Receptor agonist GW4064 in rat", 55th Annual Meeting of the American Association for the Study of Liver Diseases (AASLD), (Abstract).
Loomba et al., (2015) "Polyunsaturated fatty acid metabolites as novel lipidomic biomarkers for noninvasive diagnosis of nonalcoholic steatohepatitis", Journal of Lipid Research 56: 2015.
Lu et al., "Molecular Basis for Feedback Regulation of Bile Acid Synthesis by Nuclear Receptors", Molecular Cell, 6, 507-515, 2000.
Luketic et al., (2014) "Efficacy of Obeticholic Acid In Primary Biliary Cirrhosis as Assessed by Response Criteria Associated With Clinical Outcome: A Poise Analysis", 65th Annual Meeting and Postgraduate Course of the American Association for the Study of Liver Diseases (AASLD), (Abstract).
Lundquist et al., (2010), "Improvement of Physiochemical Properties of the Tetrahydroazepinoindole Series of Farsenoid X Receptor (FXR) Agonists: Beneficial Modulation of Lipids in Primates", J. Med. Chem., 53:1774-1787.
Ma et al., "Farsenoid X Receptor is essential for normal glucose homeostasis", The Journal of Clinical Investigation, 116, 1102-1109, 2006, doi: 10.1172-JCI25604.
Ma et al., (2004) "The Role of Farsenoid X Receptor (FXR) in Glucose Metabolism", 86th Annual Meeting of the Endocrine Society (ENDO), (Abstract).
Makishima et al., "Identification of a Nuclear Receptor for Bile Acids", Science, 284,:1362-1365, 1999.
Maloney et al., "Identification of a Chemical Tool for the Orphan Nuclear Receptor FXR", Journal of Medicinal Chemistry, Supporting Info Page, 6 pages, 2000.
Maloney et al., "Identification of a Chemical Tool for the Orphan Nuclear Receptor FXR", Journal of Medicinal Chemistry, 43, 2971-2974, 2000.
Maneschi et al., (2013) "The FXR agonist obeticholic acid normalizes lipid droplet and triglyceride handling in visceral adipose tissue preadipocytes from a non-genomic rabbit model of metabolic syndrome", 16th European Congress of Endocrinology (ECE), (Abstract).
Mangelsdorf et al., "The Nuclear Receptor Superfamily: The Second Decade", Cell, 83, 835-839, 1995.
Mangelsdorf, (2005) "The Contrasting Roles of LXRs and FXR in Lipid Metabolism", Bioactive Lipids, Lipidomics and their Targets (Z1), (Abstract).
Mangelsdorf, (2006) "Nuclear receptors and transcriptional control of lipid metabolism", 197th Annual Meeting of the Society for Endocrinology (Abstract).
Maran et al., "FXR Deficiency in Mice Leads to Increased Intestinal Epithelial Cell Proliferation and Tumor Development", American Society for Pharmacology and Experimental Therapeutics, Published on Nov. 3, 2008 as DOI: 10.1124-jpet.108.145409, 35 pages.
Marinozzi et al., (2014) "Medicinal Chemistry of Farsenoid X Receptor (FXR) Modulators: The-State-of-the-Art" Current Topics in Medicinal Chemistry 14 (19): 2127-2128.
Martinez-Fernandez et al., (2008) "Specific down-regulation of the bile acid sensor FXR by silencing ATP8B1 in HepG2 cells. Effect of the FXR agonist GW4064", 3rd World Congress of Pediatric Gastroenterology, Hepatology and Nutrition (WCPGHAN) held jointly with the 41st Annual Meeting of the European Society for Paediatric Gastroenterology, Hepatology and Nutrition (ESPGHAN), (Abstract).

(56) References Cited

OTHER PUBLICATIONS

Maruyama et al., (2010) "Selective anti-androgens with a 3,3-diphenylpentane skeleton", 2010 International Chemical Congress of Pacific Basin Societies (PACIFICHEM 2010), (Abstract).

Marzolini et al., (2004) "Unexpected Complexity in Nuclear Receptor Activation by HIV Protease Inhibitors and Induction of CYP Enzymes and Transporters", 2004 Annual Meeting and Science Innovation Exposition of The American Association for the Advancement of Science (Abstract).

Mason et al., (2010) "Farnesoid-X Receptor Agonists: a New Class of Drugs for the Treatment of PBC? An International Study Evaluating the Addition of Obeticholic Acid (INT-747) to Ursodeoxycholic Acid", 61st Annual Meeting of the American Association for the Study of Liver Diseases (AASLD), (Abstract).

Matsumura et al., "Palladium-Catalyzed Asymmetric Arylation, Vinylation, and Allenylation of Tert-cyclobutanols via Enantioselective C—C Bond Cleavage", 2003, J. Am. Chem. Soc., 125, 8862-8869.

Matsuzaki et al., (2012) "FXR Activation Promotes CDX2 Degradation via the Ubiquitin-Proteosome System with Upregulation of microRNA-221-222 in Human Esophageal Cells", 5th Annual International Gastrointestinal Consensus Symposium (IGICS), (Abstract).

McMahan et al., (2009) "FXR and TGR5 activation improves nonalcoholic fatty liver disease (nafld) and increases intrahepatic myeloid suppressor cells", 60th Annual Meeting of the American Association for the Study of Liver Diseases (AASLD), (Abstract).

McMahan et al., (2011) "Bile-Acid Receptor Activation Shifts Hepatic Monocytes-Macrophages Towards an Anti-Inflammatory Phenotype and Improves Non-Alcoholic Fatty Liver Disease", 62nd Annual Meeting of the American Association for the Study of Liver Diseases (AASLD), (Abstract).

McMahan et al., (2014) "Downregulation of pro-fibrotic and pro-inflammatory genes in liver sinusoidal endothelial cells following activation of the bile acid receptors FXR and TGR5", 65th Annual Meeting and Postgraduate Course of the American Association for the Study of Liver Diseases (AASLD), (Abstract).

McMillin et al., (2014) "Central expression of the hypothalamic neuropeptide galanin is upregulated in rodent models of primary sclerosing cholangitis", 65th Annual Meeting and Postgraduate Course of the American Association for the Study of Liver Diseases (AASLD), (Abstract).

McNulty et al., (2007) "FXR Plays A Major Role In Cholic Acid Mediated Effects In High-fat Diet Fed Mice", 67th Annual Meeting and Scientific Sessions of the American Diabetes Association (ADA), (Abstract).

Meech et al., (2014) "UDP-glycosyltransferase 8 (UGT8) galactosidates bile acids and modulates FXR signalling", 2014 Joint Scientific Meeting of the Australasian Society of Clinical and Experimental Pharmacologists and Toxicologists (ASCEPT) and the Molecular Pharmacology of GPCRs (MPGPCR), (Abstract).

Mencarelli et al., (2009) "FXR Activation Corrects Immune-Dysfunction and Attenuates Inflammation in a Rodent Model of Hepatitis", Digestive Disease Week 2009 (DDW), (Abstract).

Menendez et al., (2014) "The effects of bile acids on intestinal antimicrobial peptides expression", 2014 Annual Meeting of the Canadian Association of Gastroenterology (CAG) held jointly with the Canadian Association for the Study of the Liver (CASL): Canadian Digestive Disease Week (CDDW), (Abstract).

Merk et al., (2014) "Development of partial Farsenoid X Receptor (FXR) agonists", 2014 Annual Meeting on Trends and Perspectives in Pharmaceutical Sciences (DPhG ) Annual Meeting of the German Pharmaceutical Society (DPhG), (Abstract).

Merk, et al., (2012) "Medicinal chemistry of Farsenoid X Receptor ligands: from agonists and antagonists to modulators", Future Med. Chem. 4(8), 1015-1036.

Merk et al., (2014) "Development of Partial Farsenoid X Receptor (FXR) Agonists", 23rd International Symposium on Medicinal Chemistry (ISMC) held Jointly with the European Federation for Medicinal Chemistry (EFMC), (Abstract).

Miyata et al., "Role of Farsenoid X Receptor in the Enhancement of Canalicular Bile Acid Output and Excretion of Unconjugated Bile Acids: A Mechanism for Protection against Cholic Acid-Induced Liver Toxicity", The Journal of Pharmacology andExperimental Therapeutics, 312,: 759-766, 2005.

Miyazaki et al., (2013) "Deoxycholic Acid Contributes to Chronic Kidney Disease-Dependent Vascular Calcification", 86th Annual Scientific Sessions of the American Heart Association (AHA 2013) and 2013 Resuscitation Science Symposium (RSS), (Abstract).

Modica et al., Nuclear Bile Acid Receptor FXR Protects against Intestinal Tumorigenesis, Cancer Res, 68, 9589-9594, Dec. 1, 2008.

Mohan et al., (2014) "Mechanism of FXR Mediated Apoptosis in Breast Cancer", 2014 Surrey Postgraduate Research Conference of the University of Surrey (Abstract).

Moloney et al., (2009) "The Effect of the Farsenoid X Receptor (FXR) and It'S Agonist—GSK488062B—On Experimental Models of Colitis and Cytokine Production from IBD Tissue", Digestive Disease Week 2009 (DDW), (Abstract).

Mookerjee et al., (2014) "Effects of the FXR agonist obeticholic acid on hepatic venous pressure gradient (HVPG) in alcoholic cirrhosis: a proof of concept phase 2a study", 2014 International Liver Congress (ILC) and 49th annual meeting of the European Association for the Study of the Liver (EASL), (Abstract).

Moraes et al., (2009) "The nuclear receptor FXR as a novel regulator of platelet function", 22nd Biennial Congress of the International Society on Thrombosis and Haemostasis (ISTH) held jointly with the 55th Scientific and Standardisation Committee (SSC), (Abstract).

Moschetta et al., "Prevention of cholesterol gallstone disease by FXR agonists in a mouse model", Nature Medicine, 10, 1352-1358, 2004.

Moschetta et al., (2005) "The Role of LXRs and FXR in Enterohepatic Lipid Metabolism", Tissue-Selective Nuclear Receptors (D4), (Abstract).

Moscovitz et al., (2014) "Activation of the Farsenoid X Receptor Restores Hepatic and Intestinal Bile Acid Synthetic Enzyme and Transporter Expression in Pregnant Mice", 53rd Annual Meeting of the Society of Toxicology (SOT 2014), (Abstract).

Moussa et al., (2014) "Activation of Bile Acid Receptor (FXR) Attenuates Osteoclast Differentiation, Survival and Function", 60th Annual Meeting of the Orthopaedic Research Society (ORS 2014), (Abstract).

Moya et al., (2009) "Role of nuclear receptor ligands in fatty acid-induced hepatic steatosis", 2009 Joint Meeting of the European Association for the Study of the Liver (EASL) and the American Association for the Study of Liver Diseases (AASLD) Monothematic Conference: Nuclear Receptors and Liver Disease (Abstract).

Mroz et al., (2011) "The nuclear bile acid receptor, Farsenoid X Receptor, inhibits CFTR expression and Clsecretion in colonic epithelial cells", 2011 Annual Conference of the Physiological Society (Abstract).

Mroz et al., (2013) "Activation of the nuclear bile acid receptor, Farsenoid X Receptor, acutely regulates cAMPstimulated Cl-secretion in colonic epithelial cells", 2013 Physiological Society Joint Themed Meeting on Epithelia and Smooth Muscle Interactions in Health and Disease (Abstract).

Mroz et al., (2014) "Agonists of the nuclear bile acid receptor, FXR, prevent secretory diarrhoea by a novel mechanism involving repression of CFTR promoter activity", 2014 Conference on Physiology—Physiological Society (Abstract).

Mudaliar et al., (2009) "Farnesoid-X receptor agonists—a new therapeutic class for diabetes and NAFLD—first clinical data", 45th Annual Meeting of the European Association for the Study of Diabetes (EASD), (Abstract).

Nejak-Bowen et al., (2013) "Novel therapeutic implications of modulating ß-Catenin during intrahepatic cholestasis", 64th Annual Meeting and Postgraduate Course of the American Association for the Study of Liver Diseases (AASLD), (Abstract).

Nettles et al., "Ligand Control of Coregulator Recruitment to Nuclear Receptors", Annu. Rev. Physiol. 67, 09-333, 2005.

Neuschwander Tetri, (2015) "Targeting the FXR Nuclear Receptor to Treat Liver Disease", Division of Gastroenterology and Hepatology.

(56) References Cited

OTHER PUBLICATIONS

Neuschwander-Tetri et al., (2014) "Farnesoid X nuclear receptor ligand obeticholic acid for non-cirrhotic, non-alcoholic steatohepatitis (FLINT): a multicentre, randomised, placebo-controlled trial", The Lancet 385 (9972): 956-965.

Neuschwander-Tetri et al., (2014) "Farnesoid-X nuclear receptor ligand obeticholic acid for non-cirrhotic, non-alcoholic steatohepatitis (FLINT): a multicentre, randomised, placebocontrolled trial", The Lancet.

Nevens et al., (2014) "An International Phase 3 Study of the FXR Agonist Obeticholic Acid in PBC Patients: Effects on Markers of Cholestasis Associated with Clinical Outcomes and Hepatocellular Damage", 65th Annual Meeting and Postgraduate Course of the American Association for the Study of Liver Diseases (AASLD), (Abstract).

Nevens et al., (2014) "The first primary biliary cirrhosis (PBC) phase 3 trial in two decades—an international study of the FXR agonist obeticholic acid in PBC patients", 2014 International Liver Congress (ILC) and 49th annual meeting of the European Association for the Study of the Liver (EASL), (Abstract).

Nijmeijer et al., (2009) "Genetic Variants of Farsenoid X Receptor (FXR) Predispose to Mortality and Infectious Complications in Acute Pancreatitis", Digestive Disease Week 2009 (DDW), (Abstract).

Nolan et al., (2012) "The induction of FGF19 in human ileum by bile acids reflects their relative potencies as FXR-binding ligands", 20th Annual Meeting of the United European Gastroenterology Week (UEGW), (Abstract).

Nolan et al., (2014) "The Effects of Obeticholic Acid, a Farsenoid X Receptor Agonist, in Patients With Chronic Diarrhea Secondary to Crohn's lleal Disease", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Patani et al. "Bioisosterism: A Rational Approach in Drug Design." Chemical Reviews. 1996, 96, 3147-3176.

Patman et al., (2014) "A variant of FGF19 protects the liver from cholestatic injury without inducing cancer", Nature Reviews Gastroenterology & Hepatology.

Payer et al., (2014) "The synthetic FXR agonist PX20606 attenuates bacterial translocation, intestinal inflammation, and reduces splanchnic blood flow in portal hypertensive mice", 47. Jahrestagung der Österreichischen Gesellschaft für Gastroenterologie und Hepatologie (ÖGGH) statt gemeinsam mit der 25. Lehrgang der Österreichischen Gesellschaft für Gastroenterologie und Hepatologie—47th Annual Meeting of the Austrian Society for Gastroenterology and Hepatology held jointly with the 25th training course of the Austrian Society of Gastroenterology and Hepatology (Abstract).

Parks et al., "Bile Acids: Natural Ligands for an Orphan Nuclear Receptor", Science, 284, 1365-1368, May 21, 1999.

Pedraz et al., (2012) "Transcription elongation factor TFIIS.1 gene is regulated by Farsenoid X Receptor", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SEBBM), (Abstract).

Pellicciari, (2008) "Novel targets for metabolic diseases", Metabolic Disorders: From Bench to Bedside (Abstract).

Pellicciari, (2009) "Genomic and nongenomic bile acid receptors as novel targets for the treatment of metabolic disorders", 6th Biennial Joint Meeting of the European Federation for Medicinal Chemistry (EFMC), (Abstract).

Pellicciari et al., "6a-Ethyl-Chenodeoxycholic Acid (6-ECDCA), a Potent and Selective FXR Agonist Endowed with Anticholestatic Activity", Journal of Medicinal Chemistry, 45. 3569-3572, Aug. 15, 2002.

Peng et al., (2012) "SRC-Mediated Cross-Talk Between Farnesoid X and Epidermal Growth Factor Receptors Inhibits Human Intestinal Cell Proliferation and Tumorigenesis", 53rd Annual Meeting at Digestive Disease Week (DDW 2012 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Penna et al., (2009) "Inhibition of experimental colitis by Farsenoid X Receptor agonists", 2009 European Congress of Immunology (ECI): 2nd Joint Meeting of European National Societies of Immunology under the Auspices of EFIS (Abstract).

Pertillä et al., (2010) "Adiponutrin, a lipid droplet surface enzyme—evidence for regulation by ChREBP, SREBP1c and FXR in human hepatocytes", 46th Annual Meeting of the European Association for the Study of Diabetes (EASD), (Abstract).

Plass et al., "Farsenoid X Receptor and Bile Salts are Involved in Transcriptional Regulation of the Gene Encoding the Human Bile Salt Export Pump", Hepatology, 35, 589-596, Mar. 2002.

Poupon, (2007) "Targeting cholestasis", European Association for the Study of the Liver Monothematic Conference: Primary Biliary Cirrhosis (PBC), (Abstract).

Prentiss et al., (2008) "Characterization of transporter expression in primary cultures of human hepatocytes", 10th European Meeting of the International Society for the Study of Xenobiotics (ISSX), (Abstract).

Prough et al., (2014) "PCB regulation of hepatic nuclear receptors: Implications for hepatic steatosis", 5th Asia Pacific Regional Meeting of the International Society for the Study of Xenobiotics (ISSX 2014), (Abstract).

Qin et al., (2006) "Bile acids induces hypercholesterolemia through a FXR-independent mechanism in LDLR Knockout mice", Nuclear Receptors: Orphan Brothers (X3), (Abstract).

Qin et al., (2006) "Bile acis induce hypercholesterolemia through a FXR-independent mechanism in Idlr knockout mice", 14th International Symposium on Atherosclerosis (ISA), (Abstract).

Quiroga et al., (2012) "Deficiency of Carboxylesterase 1-Esterase-x Results in Obesity, Hepatic Steatosis, and Hyperlipidemia", Hepatology, 56 (6): 2188-2198.

Radreau et al., (2014) "Bile acids receptor FXR agonists repress HBV replication in HepaRG cell", 65th Annual Meeting and Postgraduate Course of the American Association for the Study of Liver Diseases (AASLD), (Abstract).

Ratziu et al., (2014) "Starting the battle to control non-alcoholic steatohepatitis", Institute for Cardiometabolism and Nutrition, Universite Pierre et Marie Curie, Assistance Publique Hopitaux de Paris.

Renga et al., (2009) "A Dark Side of FXR Activation in Cholestasis. FXR Is a Negative Regulator of MRP4", Digestive Disease Week 2009 (DDW), (Abstract).

Renga et al., (2012) "A Farnesoid-X-receptor (FXR)-Glucocorticoid Receptor (GR) Cascade Regulates Intestinal Innate Immunity in Response to FXR Activation", 53rd Annual Meeting at Digestive Disease Week (DDW 2012 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Renga et al., (2012) "Theonellasterol: a highly selective FXR antagonist that protects against liver injury in cholestasis", 34th National Conference of the Division of Organic Chemistry—Italian Chemical Society—34 Convegno Nazionale della Divisione di Chimica Organica—Società Chimica Italiana (SCI), (Abstract).

Richter et al., (2011) "Discovery of novel and orally active FXR agonists for the potential treatment of dyslipidemia & diabetes", Bioorganic & Medicinal Chemistry Letters 21: 191-194.

Richter et al., (2011) "Optimization of a novel class of benzimidazole-based Farsenoid X Receptor (FXR) agonists to improve physicochemical and ADME properties", Bioorganic & Medicinal Chemistry Letters 21: 1134-1140.

Ricketts et al., (2006) "The coffee diterpene, cafestol requlates cholesterol homeostasis from the intestine via FXR and FGF15", Nuclear Receptors: Orphan Brothers (X3), (Abstract).

Rizzo et al., (2009) "INT-747: a Potent and Selective FXR Agonist Regulating Glucose Metabolism and Enhancing Insulin Secretion", 60th Annual Meeting of the American Association for the Study of Liver Diseases (AASLD), (Abstract).

(56) References Cited

OTHER PUBLICATIONS

Rizzo et al., (2009) "The Farsenoid X Receptor agonist int-747 enhances glucose-induced insulin secretion", 2009 Joint Meeting of the European Association for the Study of the Liver (EASL) and the American Association for the Study of Liver Diseases (AASLD) Monothematic Conference: Nuclear Receptors and Liver Disease (Abstract).
Rizzo et al., (2010) "Functional characterization of the semi-synthetic bile acid derivative INT-767, a dual FXR and TGR5 agonist", 16th World Congress of Basic and Clinical Pharmacology (WorldPharma 2010) of the International Union of Pharmacology (IUPHAR), (Abstract).
Rizzo et al., (2010) "Functional characterization of the semi-synthetic bile acid derivative INT-767, a dual FXR and TGR5 agonist", 45th Annual Meeting of the European Association for the Study of the Liver (EASL), (Abstract).
Rizzo et al., (2010) "Functional characterization of the semi-synthetic bile acid derivative INT-767, a dual FXR and TGR5 agonist", 61st Annual Meeting of the American Association for the Study of Liver Diseases (AASLD), (Abstract).
Rizzo et al., (2011) "Functional Characterization of the Semi-synthetic Bile Acid Derivative Int-767, a Dual FXR and TGR5 Agonist", 21st Conference of the Asian Pacific Association for the Study of the Liver (APASL), (Abstract).
Rizzo et al., "Role of FXR in Regulating Bile Acid Homeostasis and Relevance for Human Diseases", Current Drug Targets—Immune, Endocrine & Metabolic Disorders, 5, 289-303, 2005.
Robitaille et al., (2008) "Role of the Farsenoid X Receptor (FXR) in intestinal epithelial cell growth and differentiation", 2008 Annual Meeting of the Canadian Digestive Disease Week (CDDW), (Abstract).
Sanyal, (2011) "Emerging Treatments of NASH", 21st Conference of the Asian Pacific Association for the Study of the Liver (APASL), (Abstract).
Sanyal et al., (2009) "A New Therapy for Nonalcoholic Fatty Liver Disease and Diabetes? INT-747-the First FXR Hepatic Therapeutic Study", 60th Annual Meeting of the American Association for the Study of Liver Diseases (AASLD), (Abstract).
Sanyal et al., (2013). "Novel therapeutic targets for alcoholic hepatitis", 14th Biennial Congress of the European Society for Biomedical Research on Alcoholism (ESBRA), (Abstract).
Sanz Ortega et al., (2012) "Effect of treatment with glucocorticoids FXR-mediated signaling pathway and bile acid homeostasis", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SEBBM), (Abstract).
Savkur et al., (2005) "Regulation of Pyruvate Dehydrogenase Kinase Expression by the Farsenoid X Receptor", Bioactive Lipids, Lipidomics and their Targets (Z1), (Abstract).
Schaap et al., (2006) "Evidence for regulation of human FGF19 gene expression by ileal FXR", 57th Annual Meeting of the American Association for the Study of Liver Diseases (AASLD), (Abstract).
Schaap et al., (2009) "FGF19 represses CYP7A1 through an ERK1-2-dependent pathway", 2009 Joint Meeting of the European Association for the Study of the Liver (EASL) and the American Association for the Study of Liver Diseases (AASLD) Monothematic Conference: Nuclear Receptors and Liver Disease (Abstract).
Schaap et al., (2014) "Bile acid receptors as targets for drug development", Nat. Rev. Gastroenterol. Hepatol. 11, 55-67.
Schena et al., "Mammalian Glucocorticoid Receptor Derivatives Enhance Transcription in Yeast", Science 241, 965-967, Aug. 19, 1988.
Schittenhelm et al., (2013) "Bile acids affect beta-cell function and glucose homeostasis by interference with the Farsenoid X Receptor (FXR)", 92nd Annual Meeting of the German Physiological Society-Deutsche Physiologische Gesellschaft (DPG), (Abstract).
Schonewille et al., (2014) "Combination treatment of the novel pharmacological FXR-compound PX20606 and ezetimibe leads to massively increased neutral sterols excretion in mice", 82nd European Atherosclerosis Society Congress (EAS), (Abstract).
Schubert-Zsilavecz, (2014) "Medicinal chemistry of Farsenoid X Receptor ligands", 134th Annual Meeting of the Pharmaceutical Society of Japan (PSJ), (Abstract).
Schwabl et al., (2014) "The synthetic FXR agonist PX20606 attenuates bacterial translocation, intestinal inflammation, and reduces splanchnic blood flow in portal hypertensive mice", 2014 International Liver Congress (ILC) and 49th annual meeting of the European Association for the Study of the Liver (EASL), (Abstract).
Sepe et al., (2012) "Conicasterol E, a small heterodimer partner sparing farnesoid-X-receptor modulator endowed with a pregnane-X-receptor agonistic activity, from the marine sponge Theonella swinhoei", 34th National Conference of the Division of Organic Chemistry—Italian Chemical Society—34 Convegno Nazionale della Divisione di Chimica Organica—Società Chimica Italiana (SCI), (Abstract).
Shapiro et al., (2009) "First human experience with a synthetic Farsenoid X Receptor (FXR) agonist—INT-747 (6-ethylchenodeoxycholic acid)", 2009 Joint Meeting of the European Association for the Study of the Liver (EASL) and the American Association for the Study of Liver Diseases (AASLD) Monothematic Conference: Nuclear Receptors and Liver Disease (Abstract).
Shapiro et al., (2009) "First Human Experience With A Synthetic Farsenoid X Receptor (FXR) Agonist-INT-747 (6a-Ethylchenodeoxycholic Acid)", 60th Annual Meeting of the American Association for the Study of Liver Diseases (AASLD), (Abstract).
Sinal et al., "Targeted Disruption of the Nuclear Receptor FXR-BAR Impairs Bile Acid and Lipid Homeostasis", Cell 102:731-744, Sep. 15, 2000.
Smalley Jr. et al., (2015) "Novel heterocyclic scaffolds of GW4064 as Farsenoid X Receptor agonists", Bioorganic & Medicinal Chemistry Letters 25: 280-284.
Song et al., (2008) "Bile Acids Activate Farsenoid X Receptor and Fibroblast Growth Factor 19 Signaling To Inhibit Cholesterol 7a-Hydroxylase Gene Expression in Human Hepatocytes", 90th Annual Meeting of the Endocrine Society (ENDO), (Abstract).
Soo Shin et al., (2013) "Positive regulation of osteogenesis by bile acid through FXR", 40th Annual Congress of the European Calcified Tissue Society (ECTS 2013), (Abstract).
Staels, (2006) "Nuclear receptors as therapeutic targets to modulate the metabolic syndrome", 31st International Meeting of the Federation of the European Biochemical Societies (FEBS), (Abstract).
Staels, (2009) "Bile acids : from simple detergents to complex signalling molecules controlling lipid and glucose homeostasis", 6th Annual Congress on Metabolic Syndrome, Type II Diabetes and Atherosclerosis (Abstract).
Stayrook et al., Regulation of Carbohydrate Metabolism by the Farsenoid X Receptor, Endocrinology, 146, 984-991, 2005.
Stayrook et al., (2005) "Regulation of Carbohydrate Metabolism by the Farsenoid X Receptor", Bioactive Lipids, Lipidomics and their Targets (Z1), (Abstract).
Suzuki et al., (2008) "Mechanism of regulation of bile acid transport in the small intestine", Falk Symposium 165: 20th International Bile Acid Meeting (Abstract).
Swales et al., "The Farsenoid X Receptor is Expressed in Breast Cancer and Regulates Apoptosis and Aromatase Expression", Cancer Res., 66, 10120-10126, Oct. 15, 2006.
Takada et al., (2006) "Transcriptional regulation of mouse organic solute transporter alpha and beta by FXR and LXR alpha", Falk Symposium No. 155: XIX International Bile Acid Meeting—Bile Acids: Biological Actions and Clinical Relevance (Abstract).
Taiwanese Search Report for TW101123785, completed Jan. 16, 2013, 4 pages.
Tazuma, (2004) "A nuclear receptor ligand down-regulates cytosolic phosphollpaseA2(cPLA2)expression to reduce bile acid-Induced cyclooxygenase 2 (COX-2) activity in cholanglocytes: Implication of antlcarcinogenic action of farnesold X receptor (FXR) agonist", 18th International Bile Acid Meeting: Bile Acid and Cholesterol Metabolism and its Therapeutic Implications. (Abstract).
Tazuma et al., (2004) "A nuclear receptor ligand down-regulates cytosolic phospholipase AcPLA expression to reduce bile acid-

(56) References Cited

OTHER PUBLICATIONS induced cyclooxygenase 2 (COX-2) activity in cholangiocytes: Implication of anticarcinogenic action of Farsenoid X Receptor (FXR) agonist", Falk Symposium No. 141 Bile Acids and Cholesterol Metabolism and its Therapeutical Implications (Abstract).

Tomlinson et al., "Transgenic Mice Expressing Human Fibroblast Growth Factor-19 Display Increased Metabolic Rate and Decreased Adiposity", Endocrinology, 143, 1741-1747, May 2002.

Trauner (2010) "Nuclear hormone receptors-biliary diseases", 2010 European Association for the Study of the Liver (EASL) Monothematic Conference: Signaling in the Liver, (Abstract).

Trauner (2014) "Bile acids as regulators of hepatic transport and metabolism in cholestatic and metabolic liver diseases", 20th International Symposium on Microsomes and Drug Oxidations, (Abstract).

Trauner (2014) "FXR vs PPAR Agonists: Competitors or fellow-combatants", 2014 European Association for the Study of the Liver (EASL) Monothematic Conference: Primary Biliary Cirrhosis (PBC), (Abstract).

Unsworth et al., (2014) "Non-genomic effects of nuclear receptors: Different mechanisms of regulation of outside-in signalling in platelets", 2nd European Platelet Group Conference (EUPLAN), (Abstract).

Uriarte et al., (2014) "Ileal FGF15 contributes to fibrosis-associated hepatocellular carcinoma development", International Journal of Cancer.

Urizar et al., "The Farnesoid X-activated Receptor Mediates Bile Acid Activation of Phospholipid Transfer Protein Gene Expression", The Journal of Biological Chemistry, 275, 39313-39317, Dec. 15, 2000.

Urizar et al., "A Natural Product That Lowers Cholesterol as an Antagonist Ligand for FXR", Science, 296, 1703-1706, May 31, 2002.

Vairappan et al., (2009) "Modulation of the DDAH-ADMA pathway with the Farnesoid receptor (FXR) agonist INT-747 restores hepatic eNOS activity and lowers portal pressure in cirrhotic rats", 2009 Annual Meeting of the British Association for the Study of the Liver, (Abstract).

Vairappan et al., (2009) "Modulation of the DDAH-ADMA pathway with the Farnesoid X Receptor (FXR) agonist INT-747 restores hepatic eNOS activity and lowers portal pressure in cirrhotic rats", 60th Annual Meeting of the American Association for the Study of Liver Diseases, (Abstract).

Vaquero et al., (2012) "Role of BCRP in FXR-induced chemoresistance in liver and intestinal cancer cells", 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology, (Abstract).

Vassie et al., (2014) "Obeticholic Acid, a Farsenoid X Receptor Agonist, Reduces Bile Acid Synthesis in Patients With Primary Bile Acid Diarrhea", 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Verbeke et al., (2013) "Obeticholic acid, a farnesoid-X receptor agonist, improves portal hypertension by two distinct pathways in cirrhotic rats", 64th Annual Meeting and Postgraduate Course of the American Association for the Study of Liver Diseases, (Abstract).

Verbeke et al., (2014) "Obeticholic acid, a Farnesoid-X receptor agonist, improves portal hypertension in cirrhotic rats", 26th Belgian Week of Gastroenterology, (Abstract).

Verbeke et al., (2014) "Obeticholic acid, a Farnesoid-X receptor agonist, reduces bacterial translocation and restores intestinal permeability in a rat model of cholestatic liver disease", 2014 International Liver Congress (ILC) and 49th annual meeting of the European Association for the Study of the Liver, (Abstract).

Verbeke et al., (2014) "Obeticholic acid, an FXR agonist, reduces bacterial translocation in experimental cholestasis", 26th Belgian Week of Gastroenterology, (Abstract).

Visschers et al., (2011) "FXR stimulation with INT-747 in a rat biliary drainage model protects from hepatocellular injury after loss of enterohepatic circulation", 2011 Annual Meeting of the British Association for the Study of the Liver, (Abstract).

Visschers et al., (2012) "Cholangiopathy is the trigger for intestinal failure associated liver disease through failure of cyp7a1 inhibition resulting from lack of FXR stimulation after biliary drainage in rats", 34th Annual Congress of the European Society for Clinical Nutrition and Metabolism, (Abstract).

Visschers et al., (2012) "FXR stimulation with INT-747 in a rat biliary drainage model protects from hepatocellular injury after loss of enterohepatic circulation", 47th Annual Meeting of the European Association for the Study of the Liver, (Abstract).

Vlasuk et al., (2007) "Introduction to mechanistic approaches to increasing high density lipoprotein cholesterol", 233rd National Meeting of the American Chemical Society (Abstract).

Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003) (Year: 2003).

Wagner et al., (2007) "Absence of FXR Protects Mice from Bile-infarcts in Biliary Obstruction by Reduction of Bile Acid-Independent Bile Flow: Implications for Targeting FXR in Treatment of Cholestasis?", 42nd Annual Meeting of the European Association for the Study of the Liver, (Abstract).

Wagner et al., (2007) "Ursodeoxycholic acid (UDCA) stimulates intestinal fibroblast growth factor 15 (Fgf-15) expression independent of the Farsenoid X Receptor (FXR)", Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT), (Abstract).

Wang et al., "FXR: a metabolic regulator and cell protector", Cell Research 18(11): 1087-1095, 2008, doi: 10.1038-cr.2008.289.

Wang et al., (2007) "FXR Modulates Renal Lipid Metabolism and Fibrosis in Diabetic Nephropathy", 2007 Experimental Biology Annual Meeting (FASEB) held jointly with the 2007 Annual Meeting of the American Society for Investigative Pathology, (Abstract).

Wang et al., (2008) "FXR Agonist Modulates Renal Lipid Metabolism, Inflammation, Oxidative Stress and Fibrosis in Diet-induced Obesity and Renal Disease", 2008 Nuclear Receptors: Orphan Brothers, (Abstract).

Wang et al., (2009) "Farsenoid X Receptor Deficiency Accelerates Diabetic Nephropathy in Nephropathy-Resistant C57BL-6 Mice", 42nd Annual Meeting and Exposition of the American Society of Nephrology, (Abstract).

Wang et al., (2010) "Dual Bile Acid Receptors Agonist INT-767 Prevents Diabetic Nephropathy through Multiple Mechanisms", 43rd Annual Meeting and Exposition of the American Society of Nephrology, (Abstract).

Wang et al., (2014) "Treatment with the FXR-TGR5 dual agonist INT-767 decreases NAFLD-NASH in mice fed a Western diet", 65th Annual Meeting and Postgraduate Course of the American Association for the Study of Liver Diseases, (Abstract).

Watanabe et al., "Bile acids lower triglyceride levels via a pathway involving FXR, SHP, and SREBP-1c", The Journal of Clinical Investigation, 113, 1408-1418, May 2004.

Watanabe et al., (2006) "Bile acids induce energy expenditure by promoting intracellular thyroid hormone activation", Nature Publishing Group 439 (26): 484-489.

Watanabe et al., (2010) "Lowering bile acid pool size with an FXR agonist induces obesity and diabetes through the decrease of energy expenditure", 2010 Nuclear Receptors: Development, Physiology and Disease, (Abstract).

Watts, (2013) "Hepatic Steatosis, Dyslipoproteinaemia and Cardiometabolic Disease", 2013 Annual Scientific Meeting of the Australian Diabetes Educators Association (ADEA) and the Australian Diabetes Society (ADS), (Abstract).

Willson et al., "Chemical Genomics: Functional Analysis of Orphan Nuclear Receptors in the Regulation of Bile Acid Metabolism", Medicinal Research Reviews, 21, 513-522, 2001.

Winkler et al., (2012) "Transcriptional regulation of hepatic and extrahepatic glucuronidation in tgUGT1A WT mice in obstructive

(56) References Cited

OTHER PUBLICATIONS cholestasis (BDL) and by FXR agonist GW4064", 63rd Annual Meeting and Postgraduate Course of the American Association for the Study of Liver Diseases, (Abstract).
Wittenburg et al., "FXR and ABCG5-ABCG8 as Determinants of Cholesterol Gallstone Formation From Quantitative Trait Locus Mapping in Mice", Gastroenterology, 125, 868-881, Sep. 2003.
Xie et al., (2014) "Metabolites profiling identifies a key role of Farsenoid X Receptor for glucose metabolism in proliferating cells", 5th Asia Pacific Regional Meeting of the International Society for the Study of Xenobiotics (Abstract).
Xing et al., (2007) "Adrenal Expression of 3s-Hydroxysteroid Dehydrogenase Type II Is Regulated by the Farsenoid X Receptor (FXR, NR1H4)", 89th Annual Meeting of the Endocrine Society, (Abstract).
Xing et al., (2008) "FXR Induces Liver Hypertrophy Through the Homeobox Factor Hex", Digestive Disease Week 2008, (Abstract).
Xu et al., (2014) "The Role of Bile Acid Receptor FXR Activation on NHE8 Expression Regulation", 55th Annual Meeting at Digestive Disease Week, (Abstract).
Yamada et al., (2008) "Bile Acids Induce CDX2 Expression via Farsenoid X Receptor (FXR) in Barrett's Oesophagus", 16th Annual Meeting of the United European Gastroenterology Week, (Abstract).
Yang et al., "Spontaneous Development of Liver Tumors in the Absence of the Bile Acid Receptor Farsenoid X Receptor", Cancer Res, 67, 863-867, Feb. 1, 2007.
Jeong et al., (2005) "Expression of All 48 Nuclear Hormone Receptors in Lung Cancer", Molecular Pathogenesis of Lung Cancer: Opportunities for Translation to the Clinic, (Abstract).
Yingji et al., (2009) "Bile Acids Induce Expression of CDx2 and MUC2 in Normal Rat Gastric Epithelial Cells via Activation of Nuclear Receptor FXR—a Possible Mechanism of Intestinal Metaplasia in the Stomach", Digestive Disease Week 2009, (Abstract).
Yu et al., (2014) "A Novel Treatment for Liver Injury in Western Diet Mouse Models", 1st Annual In Silico Drug Discovery Conference, (Abstract).
Yu et al., (2014) "A novel treatment for liver injury in Western diet mouse models", 70th Annual Southwest Regional Meeting of the American Chemical Society, (Abstract).
Zhan et al., (2013) "Genome-wide binding and transcriptome analysis of human Farsenoid X Receptor in the liver", 2013 Experimental Biology Annual Meeting, (Abstract).
Zhan et al., (2014) "Genome-Wide Binding and Transcriptome Analysis of Human Farsenoid X Receptor in Primary Human Hepatocytes", PLOS One 9(9).
Zhang et al., "Activation of the nuclear receptor FXR improves hyperglycemia and hyperlipidemia in diabetic mice", PNAS 103(a): 1006-1011, Jan. 24, 2006.
Zhang et al., (2007) "FXR signaling in metabolic disease", FEBS Letters 582: 10-18.
Zhang et al., (2009) "Farsenoid X Receptor agonist WAY-362450 attenuatesliver inflammation and fibrosis in murine model of non-alcoholic steatohepatitis", Journal of Hepatology, 51: 380-388.
Zhang et al., (2010) "Identification of Novel Pathways That Control FXR-mediated Hypocholesterolemia", 2010 Nuclear Receptors: Development, Physiology and Disease (X8), (Abstract).
Zhang et al., (2010) "Identification of Novel Pathways that Control FXR-Regulated Cholesterol Homeostasis", 11th Annual Conference on Arteriosclerosis, Thrombosis and Vascular Biology, (Abstract).
Zhang et al., (2015) "GW4064, an agonist of Farsenoid X Receptor (FXR), represses CYP3A4 expression in human hepatocytes by inducing small heterodimer partner (SHP) expression", downloaded from dmd.aspetjournals.org at ASPET Journals on Mar. 10, 2015, 23 pages.
Zollner et al., "Role of Nuclear Receptors in the Adaptive Response to Bile Acids and Cholestasis: Pathogenetic and Therapeutic Considerations", Molecular Pharmaceutics 3(3): 231-251, 2006.
U.S. Appl. No. 16/597,056, filed Oct. 9, 2019, Kinzel et al.
U.S. Appl. No. 16/813,314, filed Mar. 9, 2020, Kirby et al.
U.S. Appl. No. 16/883,669, filed May 26, 2020, Kinzel et al.

Abe, et al., "Reactions of 2-Amino-,2-Alkylamino-, and 2-Piperidino-1-aza-azulenes with Aryl and Chlorosulfonyl Isocyanates", Journal of Heterocyclic Chemistry, 1996, 33(4), 1323-1331.
Alkhouri et al. Noninvasive Diagnosis of NASH and Liver Fibrosis Within the Spectrum of NAFLD. Gastroenterol Hepatol (N Y). Oct. 2012;8(10):661-8.
Bart, et al., (2004) "Perspective targets in the treatment of the metabolic syndrome" 13th European Congress on Obesity (European Association for the Study of Obesity (Abstract).
Bates et al., "A liver-targeted acetyl CoA carboxylase inhibitor reduces hepatic steatosis and liver injury in a murine model of NASH", Journal of Hepatology, vol. 66, No. 1, Apr. 1, 2017, XP085012355.
Bhattacharya, et al. in Brittain, ed. Polymorphism in Pharmaceutical Solids, 2009, p. 334.
Caira. Crystalline Polymorphism of Organic Compounds. Topics in Current Chemistry, (1998), 198:163-208.
Caplus record for US 2007/020840 A1 by Elzein et al. (retrieved Nov. 2013).
Carotti, et al., (2014) "Beyond Bile Acids: Targeting Farnesoid X Receptor (FXR) with Natural and Synthetic Ligands" Current Topics in Medicinal Chemistry 14: 2129-2142.
Carr et al., (2015) "FXR Agonists as Therapeutic Agents for Non-Alcoholic Fatty Liver Disease", Curr Atheroscler Rep, vol. 17, No. 4, pp. 1-14.
Cheung et al., Combined ursodeoxycholic acid (UDCA) and fenofibrate in primary biliary cholangitis patients with incomplete UDCA response may improve outcomes, Alimentary Pharmacology and Therapeutics 2016; 43, pp. 283-293.
Cho et al., "Thieno[2,3-d]pyrimidine-3-acetic acids. A new class of nonpeptide endothelin receptor antagonists," Chemical & Pharmaceutical Bulletin, vol. 46, No. Month Listed 1998 (pp. 1724-1737).
ClinicalTrials. Safety, Tolerability, and Efficacy of Cilofexor in Adults with Primary Sclerosing Cholangitis without Cirrhosis. Oct. 24, 2016. https://clinicaltrials.gov/ct2/show/NCT02943460.
Corbett, "Review of recent acetyl-CoA carboxylase inhibitor patents: mid-2007-2008," Expert Opinion on Therapeutic Patents, vol. 19, No. 7, No Month Listed 2009 (pp. 943-956).
Database CA [online] Chemical Abstracts Service, Columbus, Ohio, US; Quelet, Raymond et al: "Preparation of o-methoxystrene; transformation into o-methoxyphenylacetylene", XP002771178, Retrieved from STN database accession no. 1947:3573 Abstract, 2 pages.
Database Registry [online] RN 1089878-77-2, Dec. 25, 2008.
Database Registry [online] RN 1089896-86-5, Dec. 25, 2008.
Database Registry [online] RN 1089952-27-1, Dec. 25, 2008.
Database Registry [online] RN 1222836-90-9, May 13, 2010.
El-Barbary, et al. Synthesis of 5'-amino- and 5'-azido-2',5'-dideoxy nucleosides from thieno[2,3-d]pyrimidine-2,4(1H,3H)-dione. Monatshefte für Chemie. 1995; 126(5):593-600.
Eshraghian. Current and emerging pharmacological therapy for non-alcoholic fatty liver disease. World J Gastroenterol. Nov. 14, 2017;23(42):7495-7504.
Extended European Search Report and Opinion dated Aug. 3, 2020 for EP Application No. 20179813.9. 7 pages.
Extended European Search Report and Opinion dated Oct. 4, 2017 for EP Application No. 17000383.4. 8 pages.
Extended European Search Report dated Dec. 10, 2019 for EP Application No. 19190936.5. (7 pages).
Extended European Search Report dated Dec. 17, 2019 for EP Application No. 19176040.4. (7 pages).
Extended European Search Report dated Feb. 26, 2015 for EP Application No. 12848361.7. (3 pages).
Extended European Search Report dated Jun. 7, 2018 for EP Application No. 16735485.1. (7 pages).
Extended European Search Report dated Mar. 20, 2018 for EP Application No. 17209455.9. (7 pages).
Extended European Search Report for EP17175336.1 dated Jul. 19, 2017, 8 pages.
Extended European Search Report for EP19188723.1 dated Oct. 24, 2019, 8 pages.
Fenofibrate Prescribing Information. Shionogi Inc. Reference ID: 3245094. Revised Jan. 2013. 15 pages.

(56) References Cited

OTHER PUBLICATIONS

Fernandez et al., "Bayesian-regularized Genetic Neural Networks Applied to the Modeling on Non-Peptide Antagonists for the Human Luteinizing Hormone-releasing Hormone Receptor", Journal of Molecular Graphics and Modelling, 2006, 25(4), 410-422.
Gilead Press Release, "Gilead Announces Phase 2 Results for GS-0976 in Nonalcoholic Steatohepatitis (NASH)", Oct. 24, 2017, retrieved Nov. 6, 2019, 4 pages.
Goedeke et al., "Acetyl-CoA carboxylase inhibition reverses NAFLD and hepatic insulin resistance but promotes hyptertriglyceridemia in rodents", Hepatology, 2018, Hepatology, vol. 68, No. 6, pp. 2197-2211.
Goedeke et al., "Mechanism for hypertriglyceridemia and effect of fibrate coadministration during acetyl-CoA carboxylase inhibitor treatment", EASL The International Liver Congress, Apr. 11-15, 2018, Paris, Abstract, 1 page.
Goedeke et al., "Mechanism for hypertriglyceridemia and effect of fibrate coadministration during acetyl-CoA carboxylase inhibitor treatment", EASL The International Liver Congress, Apr. 11-15, 2018, Paris, Poster, 2018, 1 page.
Hagström et al., Fibrosis stage but not NASH predicts mortality and time to development of severe liver disease in biopsy-proven NAFLD, Journal of Hepatology 2017, vol. 67, pp. 1265-1273.
Healy, et al. Pharmaceutical solvates, hydrates and amorphous forms: A special emphasis on cocrystals. Advanced Drug Delivery Reviews. vol. 117, Aug. 1, 2017, pp. 25-46.
Huang et al., "Design, Synthesis, and Biological Evaluation of Novel Nonsteriodal Farnesoid X Receptor (FXR) Antagonists: Molecular Basis of FXR Antagonism", Chem Med Chem, 2015, vol. 10, pp. 1184-1199.
International Preliminary Report on Patentability for International Application No. PCT/US2018/054738 dated Apr. 8, 2020. 9 pages.
International Search Report and Written Opinion dated Feb. 4, 2013 for PCT/US2012/064528. (14 pages).
International Search Report and Written Opinion dated Jun. 30, 2017 for PCT/US2017/020271. (17 pages).
International Search Report and Written Opinion dated Mar. 30, 2016 for PCT/US2016/012673. (8 pages).
International Search Report and Written Opinion for International Application No. PCT/US2017/036743 dated Jul. 25, 2017. (10 pages).
International Search Report and Written Opinion for International Application No. PCT/EP2012/002941 dated Aug. 7, 2012. (9 pages).
International Search Report and Written Opinion for PCT/US2017/036727 dated Sep. 12, 2017, 15 pages.
International Search Report and Written Opinion for PCT/US2018/054738 dated Jan. 1, 2019, 12 pages.
International Search Report and Written Opinion for PCT/US2020/018403 dated Jun. 18, 2020, 20 pages.
International Search Report and Written Opinion for PCT/US2020/021722 dated Jun. 19, 2020, 11 pages.
Jourdan, et al. Synthesis of Cyclic and Acyclic Nucleoside Analogues Having a Thiophene or Dihydrothiophene Ring Fused to the d Side of an Uracyl, J. Heterocyclic Chem, 1995, 32, p. 953-957.
Kim et al., "Acetyl COA carboxylase inhibition reduces hepatic steatosis but elevates plasma triglycerides in mice and humans: A bedside to bench investigation", Cell Metabolism, 2017, vol. 26, pp. 394-406, doi: 10.1016/j.cmet.2017.07.009.
Kostapanos et al. Current role of fenofibrate in the prevention and management of non-alcoholic fatty liver disease. World J Hepatol. Sep. 27, 2013;5(9):470-8.
Lawitz et al., "Acetyl-CoA carboxylase (ACC) inhibitor GS-0976 leads to suppression of hepatic de novo lipogenesis and significant improvements in MRI-PDFF, MRE, and markers of fibrosis after 12 weeks of therapy in patients with NASH", Journal of Hepatology, 2017, vol. 66, Issue 1, Supplement, page S34, doi: https://doi.org/10.1016/S0168-8278(17)30328-8.
Lawitz, et al. Fenofibrate Mitigates Increases in Serum Triglycerides Due to the ACC Inhibitor Firsocostat in Patients With Advanced Fibrosis Due to NASH. Presented at AASLD: The Liver Meeting® 2019, Nov. 8-12, 2019, Boston, MA.
Levy et al., Pilot study: fenofibrate for patients with primary biliary cirrhosis and an incomplete response to ursodeoxycholic acid, Alimentary Pharmacology and Therapeutics 2011; 33, pp. 235-242.
Loomba et al., "GS-0976 reduces hepatic steatosis and fibrosis markers in patients with nonalcoholic fatty liver disease", Gastroenterology, Nov. 2018, vol. 155, No. 5, pp. 1463-1473, e6, doi: 10.1053/j.gastro.2018.07.027.
Malamas et al., "Quinazolineacetic Acids and Related Analogues as Aldose Reductase Inhibitors", Journal of Medicinal Chemistry, 1991, 34(4), 1492-1503.
Quelet, et al. Preparation of o-methoxystyrene; transformation into o-methoxyphenylacetylene. Compt. Rend. 1946; 223:159-160.
Rana, et al: "Catalytic electrophilic halogenationsand haloalkoxylations by non-heme iron halides", Advanced Synthesis & Catalysis, vol. 256, No. 11-12, pp. 2453-2458, 2014.
Registry (STN) [online], May 8, 2009, retrieval date Apr. 22, 2016, CAS registration Nos. 1144464-32-3, 1089988-38-4, 1089987-08-5, 1089986-32-2, 1089984-45-1, 1089983-19-6, 1089981-89-4, 1089978-89-1, 1089978-06-2, 1089978-06-2, 1089978-05-1, 1089977-32-1 and the like.
Renault, et al. Synthesis and Antiviral Evaluation of Furopyramidine Diones: Cyclic and Acyclic Nucleoside Analogues, Heterocycles, 1995, 41(5), abstract.
Saal, et al. Pharmaceutical salts: A summary on doses of salt formers from the Orange Book. European Journal of Pharmaceutical Sciences. vol. 49, Issue 4, Jul. 16, 2013, pp. 614-623.
Sasaki et al., "Discovery of a Thieno[2,3-d] pyrimidine-2,4-dione Bearing a p-Methoxyureidophenyl Moiety at the 6-Position: A Highly Potent and Orally Bioavailable Non-Peptide Antagonist for the Human Luteinizing Hormone-Releasing Hormone Receptor", Journal of Medicinal Chemistry, 2003, 46(1), 113-124.
Stiede et al., "Acetyl-coenzyme A carboxylase inhibition reduces de novo lipogenesis in overweight male subjects: A randomized, double-blind, crossover study", Hepatology, 2017, vol. 66, No. 2, pp. 324-334.
Sunkara, et al. A Carbocyclic 7-Deazapurine-pyramidine hybrid nucleoside, Collect. Czech. Chem. Commune, 2006, vol. 71, No. 8, p. 1161-1168.
Talal, et al. Simtuzumab, an antifibrotic monoclonal antibody against lysyl oxidase-like 2 (LOXL2) enzyme, appears safe and well tolerated in patients with liver disease of diverse etiology. J of Hepatology. Apr. 2013; vol. 58, S1-632, poster #1319.
Trauner, et al. The Nonsteroidal Farnesoid X Receptor Agonist Cilofexor (GS-9674) Improves Markers of Cholestasis and Liver Injury in Patients With Primary Sclerosing Cholangitis. Hepatology, 2019; 70(3):788-801.
Vlasov et al., "The Synthesis of Novel 3-Substituted 1-Alkyl-5-Methyl-6-(3-Aryl-1,2,4-Oxadiazole-5-Yl)Thieno[2,3-D]Pyrimidine-2,4(1H3H)-Diones and Their Antimicrobial Activity", Journal of Organic and Pharmaceutical Chemistry, 2011, 9(3):51-55, with English translation, 6 pages.
You et al., "Section II Lead Optimization", Medicinal Chemistry, 2nd version, Chemical Industry Press, pp. 25-29, 2008.
Amiri-Kordestani et al., Why Do Phase III Clinical Trials in Oncology Fail so Often?, Advance Access 2012, vol. 104, Issue 8, pp. 568-569, DOI: 10.1093/jnci/djs180.
Balbach S et al., Pharmaceutical evaluation of early development candidates "the 100 mg approach", International Journal of Pharmaceutics, 2004, vol. 275, pp. 1-12.
CAS Registry No. 1089778-56-2; STN Entry Date Dec. 25, 2008; Thieno[2,3-d]pyrimidine-6-carboxylic acid, 3-[2-(diethylamino)-2-oxoethyl]-1,2,3,4-tetrahydro-5-methyl-2,4-dioxo-1-(2-phenylethyl)-, ethyl ester, printed Oct. 9, 2020. 2 pages.
CAS Registry No. 1089786-92-4; STN Entry Date Dec. 25, 2008; Thieno[2,3-d]pyrimidine-3(2H)-acetamide, 6-acetyl-1,4-dihydro-5-methyl-N-(2-methylphenyl)-2,4-dioxo-1-(2-phenylethyl)-, printed Oct. 9, 2020. 3 pages.
CAS Registry No. 1089787-86-9; STN Entry Date Dec. 25, 2008; Thieno[2,3-d]pyrimidine-3(2H)-acetamide, 6-acetyl-1,4-dihydro-N-(2-methoxyphenyl)-5-methyl-2,4-dioxo-1-(2-phenylethyl)-, printed Oct. 9, 2020. 3 pages.

(56) References Cited

OTHER PUBLICATIONS

CAS Registry No. 1089789-10-5; STN Entry Date Dec. 25, 2008; Thieno[2,3-d]pyrimidine-3(2H)-acetamide, 6-acetyl-1,4-dihydro-N-(4-methoxyphenyl)-5-methyl-2,4-dioxo-1-(2-phenylethyl)-, printed Oct. 9, 2020. 3 pages.
CAS Registry No. 1089797-59-0; STN Entry Date Dec. 25, 2008; Thieno[2,3-d]pyrimidine-3(2H)-acetamide, 6-acetyl-1,4-dihydro-5-methyl-2,4-dioxo-1-(2-phenylethyl)-, printed Oct. 9, 2020. 3 pages.
CAS Registry No. 1089798-87-7; STN Entry Date Dec. 25, 2008; Thieno[2,3-d]pyrimidine-3(2H)-acetamide, 6-acetyl-1,4-dihydro-N,N,5-trimethyl-2,4-dioxo-1-(2-phenylethyl)-, printed Oct. 9, 2020. 3 pages.
CAS Registry No. 1089800-09-8; STN Entry Date Dec. 25, 2008; Thieno[2,3-d]pyrimidine-3(2H)-acetamide, 6-acetyl-N,N-diethyl-1,4-dihydro-5-methyl-2,4-dioxo-1-(2-phenylethyl)-, printed Oct. 9, 2020. 3 pages.
CAS Registry No. 1089806-06-3; STN Entry Date Dec. 25, 2008; Thieno[2,3-d]pyrimidine-6-carboxylic acid, 1,2,3,4-tetrahydro-5-methyl-2,4-dioxo-3-[2-oxo-2-[(phenylmethyl)amino]ethyl]-1-(2-phenylethyl)-, ethyl ester, printed Oct. 9, 2020. 3 pages.
CAS Registry No. 1089806-14-3; STN Entry Date Dec. 25, 2008; Thieno[2,3-d]pyrimidine-6-carboxylic acid, 1,2,3,4-tetrahydro-5-methyl-2,4-dioxo-3-[2-oxo-2-(phenylamino)ethyl]-1-(2-phenylethyl)-, ethyl ester, printed Oct. 9, 2020. 3 pages.
CAS Registry No. 1089806-45-0; STN Entry Date Dec. 25, 2008; Thieno[2,3-d]pyrimidine-6-carboxylic acid, 1,2,3,4-tetrahydro-3-[2-[(2-methoxyphenyl)amino]-2-oxoethyl]-5-methyl-2,4-dioxo-1-(2-phenylethyl)-, ethyl ester, printed Oct. 9, 2020. 3 pages.
CAS Registry No. 1089806-99-4; STN Entry Date Dec. 25, 2008; Thieno[2,3-d]pyrimidine-6-carboxylic acid, 1,2,3,4-tetrahydro-5-methyl-3-[2-(1-naphthalenylamino)-2-oxoethyl]-2,4-dioxo-1-(2-phenylethyl)-, ethyl ester, printed Oct. 9, 2020. 3 pages.
CAS Registry No. 1089807-07-7; STN Entry Date Dec. 25, 2008; Thieno[2,3-d]pyrimidine-3(2H)-acetamide, 6-acetyl-1,4-dihydro-5-methyl-2,4-dioxo-1-(2-phenylethyl)-N-(phenylmethyl)-, printed Oct. 9, 2020. 3 pages.
CAS Registry No. 1089808-09-2; STN Entry Date Dec. 25, 2008; Thieno[2,3-d]pyrimidine-3(2H)-acetamide, 6-acetyl-1,4-dihydro-5-methyl-2,4-dioxo-N-phenyl-1-(2-phenylethyl)-, printed Oct. 9, 2020. 3 pages.
CAS Registry No. 1089809-28-8; STN Entry Date Dec. 25, 2008; Thieno[2,3-d]pyrimidine-3(2H)-acetamide, 6-acetyl-1,4-dihydro-5-methyl-N-(4-methylphenyl)-2,4-dioxo-1-(2-phenylethyl)-, printed Oct. 9, 2020. 3 pages.
CAS Registry No. 1089823-87-9; STN Entry Date Dec. 25, 2008; Thieno[2,3-d]pyrimidine-6-carboxylic acid, 1,2,3,4-tetrahydro-5-methyl-3-[2-[(4-methylphenyl)amino]-2-oxoethyl]-2,4-dioxo-1-(2-phenylethyl)-, ethyl ester, printed Oct. 9, 2020. 3 pages.
CAS Registry No. 1089878-58-9; STN Entry Date Dec. 25, 2008; Thieno[2,3-d]pyrimidine-6-carboxylic acid, 3-[2-(dimethylamino)-2-oxoethyl]-1,2,3,4-tetrahydro-5-methyl-2,4-dioxo-1-(2-phenylethyl)-, ethyl ester, printed Oct. 9, 2020. 2 pages.
CAS Registry No. 1089894-24-5; STN Entry Date Dec. 25, 2008; Thieno[2,3-d]pyrimidine-6-carboxylic acid, 1,2,3,4-tetrahydro-5-methyl-3-[2-[(2-methylphenyl)amino]-2-oxoethyl]-2,4-dioxo-1-(2-phenylethyl)-, ethyl ester, printed Oct. 9, 2020. 3 pages.
CAS Registry No. 1089894-94-9; STN Entry Date Dec. 25, 2008; Thieno[2,3-d]pyrimidine-6-carboxylic acid, 1,2,3,4-tetrahydro-3-[2-[(4-methoxyphenyl)amino]-2-oxoethyl]-5-methyl-2,4-dioxo-1-(2-phenylethyl)-, ethyl ester, printed Oct. 9, 2020. 3 pages.
CAS Registry No. 1089895-94-2; STN Entry Date Dec. 25, 2008; Thieno[2,3-d]pyrimidine-6-carboxylic acid, 3-[2-(cyclohexylamino)-2-oxoethyl]-1,2,3,4-tetrahydro-5-methyl-2,4-dioxo-1-(2-phenylethyl)-, ethyl ester, printed Oct. 9, 2020. 2 pages.
CAS Registry No. 1089938-46-4; STN Entry Date Dec. 25, 2008; Thieno[2,3-d]pyrimidine-6-carboxylic acid, 3-[2-[(4-bromophenyl)amino]-2-oxoethyl]-1,2,3,4-tetrahydro-5-methyl-2,4-dioxo-1-(2-phenylethyl)-, ethyl ester, printed Oct. 9, 2020. 3 pages.
CAS Registry No. 1089955-77-0; STN Entry Date Dec. 25, 2008; Thieno[2,3-d]pyrimidine-3(2H)-acetamide, 6-acetyl-N-(4-bromophenyl)-1,4-dihydro-5-methyl-2,4-dioxo-1-(2-phenylethyl)-, printed Oct. 9, 2020. 3 pages.
CAS Registry No. 1089956-79-5; STN Entry Date Dec. 25, 2008; Thieno[2,3-d]pyrimidine-3(2H)-acetamide, 6-acetyl-1,4-dihydro-5-methyl-N-1-naphthalenyl-2,4-dioxo-1-(2-phenylethyl)-, printed Oct. 9, 2020. 3 pages.
CAS Registry No. 1089957-54-9; STN Entry Date Dec. 25, 2008; Thieno[2,3-d]pyrimidine-3(2H)-acetamide, 6-acetyl-N-cyclohexyl-1,4-dihydro-5-methyl-2,4-dioxo-1-(2-phenylethyl)-, printed Oct. 9, 2020. 3 pages.
CAS Registry No. 1089966-20-0; STN Entry Date Dec. 25, 2008; Thieno[2,3-d]pyrimidine-6-carboxylic acid, 3-(2-amino-2-oxoethyl)-1,2,3,4-tetrahydro-5-methyl-2,4-dioxo-1-(2-phenylethyl)-, printed Oct. 9, 2020. 3 pages.
CAS Registry No. 1089970-09-1; STN Entry Date Dec. 25, 2008; Thieno[2,3-d]pyrimidine-6-carboxylic acid, 1,2,3,4-tetrahydro-3-[2-[(2-methoxyphenyl)amino]-2-oxoethyl]-5-methyl-2,4-dioxo-1-(2-phenylethyl)-, printed Oct. 9, 2020. 3 pages.
CAS Registry No. 1089971-35-6; STN Entry Date Dec. 25, 2008; Thieno[2,3-d]pyrimidine-6-carboxylic acid, 1,2,3,4-tetrahydro-3-[2-[(4-methoxyphenyl)amino]-2-oxoethyl]-5-methyl-2,4-dioxo-1-(2-phenylethyl)-, printed Oct. 9, 2020. 3 pages.
CAS Registry No. 1089971-50-5; STN Entry Date Dec. 25, 2008; Thieno[2,3-d]pyrimidine-6-carboxylic acid, 1,2,3,4-tetrahydro-5-methyl-2,4-dioxo-3-[2-oxo-2-[(phenylmethyl)amino]ethyl]-1-(2-phenylethyl)-, printed Oct. 9, 2020. 3 pages.
CAS Registry No. 1089972-49-5; STN Entry Date Dec. 25, 2008; Thieno[2,3-d]pyrimidine-6-carboxylic acid, 3-[2-[(4-bromophenyl)amino]-2-oxoethyl]-1,2,3,4-tetrahydro-5-methyl-2,4-dioxo-1-(2-phenylethyl)-, printed Oct. 9, 2020. 3 pages.
CAS Registry No. 1089977-31-0; STN Entry Date Dec. 25, 2008; Thieno[2,3-d]pyrimidine-6-carboxylic acid, 1,2,3,4-tetrahydro-5-methyl-3-[2-(1-naphthalenylamino)-2-oxoethyl]-2,4-dioxo-1-(2-phenylethyl)-, printed Oct. 9, 2020. 3 pages.
Chozaigaku-Kiso to Oyo—[Pharmaceutics—Fundamentals to Practical Application], Nanzando Co., Ltd., Sep. 20, 1977, pp. 142-145.
ClinicalTrials.gov; NCT02781584 (Year: 2016). 7 pages.
ClinicalTrials.gov; NCT02854605 (Year: 2016). 5 pages.
Communication pursuant to Rule 114(2) EPC regarding an Anonymous Third Party Observation for European Patent Application No. 20708721.4 dated Sep. 20, 2021. 8 pages.
Crawley, M.L., Farnesoid X receptor modulators: a patent review, Expert Opin. Ther. Patents (2010) 20(8):1047-1057, doi: 10.1517/13543776.2010.496777, XP055401832.
Gokhale et al., Chapter 4 API Solid-Form Screening and Selection, Developing Solid Oral Dosage Forms, 2017 Elsevier Inc . . . 28 pages.
Gordon et al., Health Care Use and Costs Among Patients With Nonalcoholic Steatohepatitis With Advanced Fibrosis Using the Fibrosis-4 Score, Hepatology Communications 2020, vol. 4, No. 7, pp. 998-1011.
Hikime, Seiichiro. Experimental chemistry course (sequel) 2, Isolation and purification. Maruzen Co., Ltd., Jan. 25, 1967, p. 159-178, 186-187. (In Japanese with Partial English Translation).
Hiroshi Oshima, Crystallization of Polymorphs and Pseudopolymorphs and Its Control, Pharm Stage, Jan. 15, 2007, vol. 6, No. 10, pp. 48-53. (In Japanese with Partial English Translation).
History of Changes for Study: NCT02943460, ClinicalTrials.gov archive [online], Feb. 21, 2019, [Retrieved on Aug. 19, 2022], Internet clinicaltrials.gov/ct2/history/NCT02943460. 13 pages.
Jikken Kagaku Koza (Zoku) 2 Bunri to Seisei [Experimental chemistry course (sequel) 2, Isolation and purification], Maruzen Co., Ltd., Jan. 25, 1967, pp. 159-178, 186-187.
Kawasaki et al., Journal of Okayama Medical Association, 2010, vol. 122, No. 1, pp. 73-76.
Kazuhide Ashizawa, et al., Iyakuhin no Tasho Gensho to Shoseki no Kagaku [Science of crystallization and polymorphic phenomenon of pharmaceutical product], Japan, Maruzen Planet Co., Ltd., Sep. 20, 2002, pp. 3-16,273-278.
Kazunari Kondo, et al., Fenofibrate, a peroxisome proliferator-activated receptor a agonist, improves hepatic microcirculatory

(56) References Cited

OTHER PUBLICATIONS patency and oxygen availability in a high-fat-diet-inducted fatty liver in mice, Advances in Experimental Medicine and Biology 2009, 662, pp. 77-82.

Li et al., Bile Acids and Farnesoid X Receptor: Novel Target for the Treatment of Diabetic Cardiomyopathy, Current Protein Peptide Science 2019, 20(10):976-983.

Li et al., Farnesoid X Receptor Agonists as Therapeutic Target for Cardiometabolic Diseases. Frontiers in Pharmacology 2020, vol. 11, article 1247, pp. 1-15.

Mitsuhisa Yamano, Approach to Crystal Polymorph in Process Research of New Drug, Journal of Synthetic Organic Chemistry, Japan, Sep. 1, 2007, vol. 65, No. 9, pp. 907(69)-913(75).

Montagner et al., Liver PPARa is crucial for whole-body fatty acid homeostasis and is protective against NAFLD, Gut 2016, vol. 65, pp. 1202-1214.

Nakai, et al. New drug formulation science. Nanzando Co., Ltd., Apr. 25, 1984, p. 102-103, 232-233. (In Japanese with Partial English Translation).

NCT02781584: Safety, Tolerability, and Efficacy of Selonsertib, GS-0976, and GS-9674 in Adults With Nonalcoholic Steatohepatitis (NASH), ClinicalTrials.gov, 2017. 7 pages.

Ning et al., Nuclear Receptors in the Pathogenesis and Management of Inflammatory Bowel Disease, Hindawi, Mediators of Inflammation 2019, vol. 2019, Article ID 2624941. 15 pages.

Nishigaki, Sadao. Pharmaceutics—Fundamentals to Practical Application. Nanzando Co., Ltd., Sep. 20, 1977, p. 142-145. (In Japanese with Partial English Translation).

Noriyuki Takata, API form screening and selection in drug discovery stage, Pharm Stage, Jan. 15, 2007, vol. 6, No. 10, pp. 20-25.

Okano, Teisuke. New general theory of pharmaceutical science. (Revised third edition), Apr. 10, 1987, Nankodo Co., Ltd., p. 111. (In Japanese with Partial English Translation).

Opposition filed by Laboratorios Legrand S.A. for Colombian Patent Application No. NC2021/0009240 dated Nov. 19, 2021. 29 pages.

Patel et al., Cilofexor, a Nonsteroidal FXR Agonist, in Non-Cirrhotic Patients with Nonalcoholic Steatohepatitis: A Phase 2 Randomized Controlled Trial, first published Mar. 2020, doi: 10.1002/hep.31205. 31 pages.

Porez et al., Bile acid receptors as targets for the treatment of dyslipidemia and cardiovascular disease, Journal of Lipid Research 2012, vol. 53, pp. 1723-1737.

PubChem CID 132234195, retrieved from internet on Feb. 19, 2021. 8 pages.

PubChem CID 140823897, retrieved from internet on Feb. 19, 2021. 8 pages.

Quyen ,et al. Pharmaceutical Technology Report, "Utility of Polyplasdone™ Crospovidone as a Solubilizer", Ashland Epecialty ingredients, 2014. 5 pages.

Reeder et al., An Improved Method for the Palladium Cross-Coupling Reaction of oxazol-2-ylzinc Derivatives with Aryl Bromides, Organic Process Research & Development 2003, vol. 7, No. 5, pp. 696-699.

RN: 1778957-82-6, Database Registry [Online] Retrieved from STN, Jun. 12, 2015, Date of retrieval: Nov. 26, 2020.

Shah et al., Emerging drugs for the treatment of non-alcoholic steatohepatitis: a focused review of farnesoid X receptor agonists, Expert Opinion on Emerging Drugs 2020, vol. 25, No. 3, pp. 251-260.

Shin Seizaigaku [New drug formulation science], Nanzando Co., Ltd., Apr. 25, 1984, p. 102-103, 232-233.

Shin Yakuzaigaku Soron [New general theory of pharmaceutical science] (Revised third edition), Apr. 10, 1987, Nankodo Co., Ltd., p. 111.

Singhal, D. et al., Drug polymorphism and dosage form design: a practical perspective, Advanced Drug Delivery Reviews, 2004, vol. 56, pp. 335-347.

Stojancevic et al., The impact of farnesoid X receptor activation on intestinal permeability in inflammatory bowel disease, Can J Gastroenterol 2012, vol. 26 No. 9, pp. 631-637.

Tanaka, A., Emerging novel treatments for autoimmune liver diseases, Hepatology Research 2019, 49, pp. 489-499.

The Japanese Pharmacopoeia, Sixteenth Edition, 2011, pp. 64-68, 2070.

Vilar-Gomez et al., Fibrosis Severity as a Determinant of Cause-Specific Mortality in Patients With Advanced Nonalcoholic Fatty Liver Disease: A Multi-National Cohort Study, Gastroenterology 2018; vol. 155, No. 2, pp. 443-457.

Wang et al., Separation of citalopram intermediate from its acetate by solvent extraction, Separation and Purification Technology 2009, vol. 68, pp. 65-69.

Yan et al., The pathophysiological function of non-gastrointestinal farnesoid X receptor, Pharmacology & Therapeutics 2021, vol. 226, 107867, pp. 1-16.

Yu; Advanced Drug Delivery Reviews, 2001, 48, pp. 27-42. doi: 10.1016/S0169-409X(01)00098-9 (Year: 2001).

Zhou et al., PPARa-UGT axis activation represses intestinal FXR-FGF15 feedback signalling and exacerbates experimental colitis, Nature Communications 2014, 5:4573. 15 pages.

Boyd et al. (Tetrahedron: Asymmetry (1993), 4(6), 1307-24).

Bucar, D et al., Disappearing Polymorphs Revisited, Angewandte Chemie International Edition, 2015, vol. 54, No. 24, pp. 6972-6993.

Crouch, R.D et al., Removal of Acyl Protecting Groups Using Solid NaOH and a Phase Transfer Catalyst, Letter 2003, pp. 991-992.

Extended European Search Report for European Application No. 22180249.9 dated Dec. 23, 2022. 8 pages.

Guillory, J.K., Ed-Brittain, H.G.: "Generation of Polymorphs, Hydrates, Solvates, And Amorphous Solids", Polymorphism In Pharmaceutical Solids, 1999 (Jan. 1, 1999), pp. 183-226.

Karlsen et al., Review article: controversies in the management of primary biliary cirrhosis and primary sclerosing cholangitis, Alimentary Pharmacology & Therapeutics 2014; 39, pp. 282-301, XP071543290.

Lugemwa, et al., Facile and Efficient Acetylation of Primary Alcohols and Phenols with Acetic Anhydride Catalyzed by Dried Sodium Bicarbonate, Catalysts 2013, pp. 954-965.

RN: 2253764-93-9, STN on the Web REGISTRY database, Chemical Abstract RN, RN: 2253764-93-9, Dec. 9, 2018. 2 pages.

Yuki Kagobutsu Kessho Sakusei Handobukku-Genri to Nouhau— [Handbook for preparing crystals of organic compounds—Principle and know-how], Jul. 25, 2008, pp. 57-79.

SEQUENCE LISTING

```
<160> NUMBER OF SEQ ID NOS: 8

<210> SEQ ID NO 1
<211> LENGTH: 100
<212> TYPE: DNA
<213> ORGANISM: Artificial Sequence
<220> FEATURE:
<223> OTHER INFORMATION: Synthetic

<400> SEQUENCE: 1
aagcctctgt ggatatgccc acaagtccca gaaccgcagt gaagagtttc tcatcacggg      60
ccgcctaagg aacggaaatt tgcacatcag tgcctgcagc                            100

<210> SEQ ID NO 2
<211> LENGTH: 100
<212> TYPE: DNA
<213> ORGANISM: Artificial Sequence
<220> FEATURE:
<223> OTHER INFORMATION: Synthetic

<400> SEQUENCE: 2
caatggtgag acgtggaaac ccgaggtatg cttgatctgt atctgccaca atggcacggc      60
tgtgtgcgat gacgtgcaat gcaatgaaga actggactgt                            100

<210> SEQ ID NO 3
<211> LENGTH: 100
<212> TYPE: DNA
<213> ORGANISM: Artificial Sequence
<220> FEATURE:
<223> OTHER INFORMATION: Synthetic

<400> SEQUENCE: 3
catacgcctg cagagttaag catgccagta tggccgagcc caagaccgtc tactgggatc      60
gagacatgtg atcaagcatc atgatgctct gaagattcat                            100

<210> SEQ ID NO 4
<211> LENGTH: 100
<212> TYPE: DNA
<213> ORGANISM: Artificial Sequence
<220> FEATURE:
<223> OTHER INFORMATION: Synthetic
```

```
<400> SEQUENCE: 4
tgctgaggcg gcgagggaga gcgttgggct tacctcactg ctttccggag cggtagcacc      60
tcctccgccg gcttcctcct cagaccgctt tttgccgcga                            100

<210> SEQ ID NO 5
<211> LENGTH: 100
<212> TYPE: DNA
<213> ORGANISM: Artificial Sequence
<220> FEATURE:
<223> OTHER INFORMATION: Synthetic

<400> SEQUENCE: 5
ccggcattct gcacgcttca aaagcgcacg tctgccgcgc tgttctcctc ttcctcatct      60
ccgggccttt cgacctcacg gtgttgccaa aatgtcgctt                            100

<210> SEQ ID NO 6
<211> LENGTH: 100
<212> TYPE: DNA
<213> ORGANISM: Artificial Sequence
<220> FEATURE:
<223> OTHER INFORMATION: Synthetic

<400> SEQUENCE: 6
atgggatccc tccaccctat gacaagaaaa agcggatggt ggtccctgct gctctcaagg      60
ttgttcggct gaagcctacc agaaagtttg cttacctggg                            100

<210> SEQ ID NO 7
<211> LENGTH: 100
<212> TYPE: DNA
<213> ORGANISM: Artificial Sequence
<220> FEATURE:
<223> OTHER INFORMATION: Synthetic

<400> SEQUENCE: 7
ggcagcctga cagtgggatc tcctccattc gttcttttaa gaccatcctt cctgctgccg      60
cccaggatgt ctattaccgg gatgagattg gtaatgtttc                            100

<210> SEQ ID NO 8
<211> LENGTH: 101
<212> TYPE: DNA
<213> ORGANISM: Artificial Sequence
<220> FEATURE:
<223> OTHER INFORMATION: Synthetic

<400> SEQUENCE: 8
gatgctcaca agggacgcaa aaacgaagga gtgattgaat tgtgtcttta ctctgatatg      60
aaaagagctt tggaaaagct ggacggaact gaagtcaacg g                          101
```

METHODS OF TREATING LIVER DISEASE

CROSS-REFERENCE TO RELATED APPLICATIONS

This application is a continuation of U.S. application Ser. No. 15/935,759, filed Mar. 26, 2018, now abandoned, which application claims the benefit of: U.S. Provisional Application Ser. No. 62/477,697, filed Mar. 28, 2017; U.S. Provisional Application Ser. No. 62/482,105, filed Apr. 5, 2017; and, U.S. Provisional Application Ser. No. 62/586,354, filed Nov. 15, 2017. The entireties of these applications are incorporated herein by reference.

SEQUENCE LISTING

The Sequence Listing associated with this application is provided in text format in lieu of a paper copy, and is hereby incorporated by reference into the specification. The name of the text file containing the Sequence Listing is 1212P3C_2018-03-26_Seq_Listing_ST25.txt. The text file created on Mar. 26, 2018, is 2.32 KB in size and submitted electronically via EFS-Web.

FIELD

The present disclosure relates to methods of preventing and/or treating liver diseases.

BACKGROUND

Liver disease is generally classified as acute or chronic based upon the duration of the disease. Liver disease may be caused by infection, injury, exposure to drugs or toxic compounds, alcohol, impurities in foods, and the abnormal build-up of normal substances in the blood, an autoimmune process, a genetic defect (such as haemochromatosis), or unknown cause(s).

Liver disease is a leading cause of death world wide. In particular, it has been seen that a diet high in fat damages the liver in ways that are surprisingly similar to hepatitis. The American Liver Foundation estimates that more than 20 percent of the population has non-alcoholic fatty liver disease (NAFLD). It is suggested that obesity, unhealthy diets, and sedentary lifestyles may contribute to the high prevalence of NAFLD. When left untreated, NAFLD can progress to non-alcoholic steatohepatitis (NASH) causing serious adverse effects. Once NASH develops, it causes the liver to swell and scar (i.e. cirrhosis) over time.

Although preliminary reports suggest positive lifestyle changes could prevent or reverse liver damage, there are no effective medical treatments for NAFLD or NASH. Accordingly, there remains a need to provide new effective pharmaceutical agents to treat liver diseases.

SUMMARY

Disclosed herein are methods of treating and/or preventing liver disease in a patient in need thereof, comprising administering to the patient a therapeutically effective amount of an acetyl-CoA carboxylase (ACC) inhibitor in combination with a therapeutically effective amount of farnesoid X receptor (FXR) agonist. The liver disease can be any liver disease, including, but not limited to, chronic and/or metabolic liver diseases, nonalcoholic fatty liver disease (NAFLD), and nonalcoholic steatohepatitis (NASH).

In certain embodiments, provided herein is a method of treating and/or preventing nonalcoholic steatohepatitis (NASH) in a patient in need thereof, comprising administering to the patient a therapeutically effective amount of an ACC inhibitor in combination with a therapeutically effective amount of a FXR agonist.

In the methods provided herein, the ACC inhibitor and the FXR agonist can be coadministered. In such embodiments, the ACC inhibitor and the FXR agonist can be administered together as a single pharmaceutical composition, or separately in more than one pharmaceutical composition. Accordingly, also provided herein is a pharmaceutical composition comprising a therapeutically effective amount of an ACC inhibitor and a therapeutically effective amount of a FXR agonist.

DETAILED DESCRIPTION

Definitions and General Parameters

Figure 1:
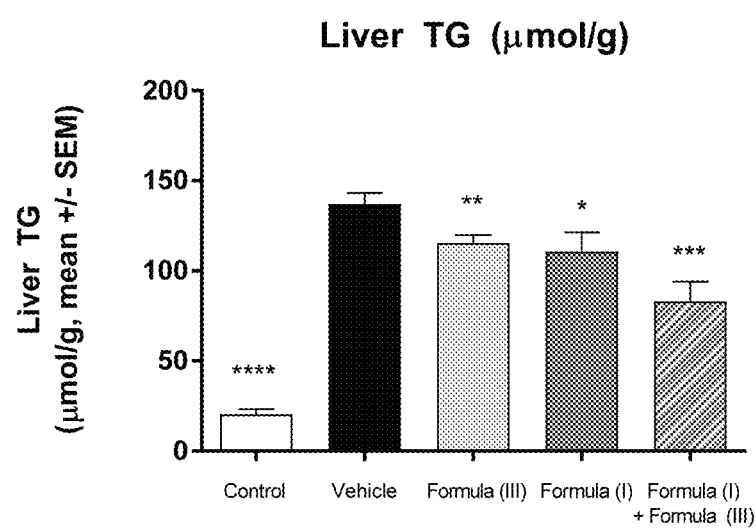
FIG. 1. Liver triglycerides in umol/g in the murine FFD model. (*$p<0.05$; $p<0.01$; *$p<0.001$;****$p<0.0001$ significantly different from vehicle by ANOVA). Graph shows mean±SEM.

As used in the present specification, the following terms and phrases are generally intended to have the meanings as set forth below, except to the extent that the context in which they are used indicates otherwise.

As used herein, the term "about" used in the context of quantitative measurements means the indicated amount ±10%, or alternatively the indicated amount ±5% or ±1%.

The term "pharmaceutically acceptable salt" refers to a salt of a compound disclosed herein that retains the biological effectiveness and properties of the underlying compound, and which is not biologically or otherwise undesirable. There are acid addition salts and base addition salts. Pharmaceutically acceptable acid addition salts may be prepared from inorganic and organic acids.

Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. *Journal of Pharmaceutical Science*, January 1977 vol. 66, No. 1, and other sources.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., *Remington's Pharmaceutical Sciences*, Mace Publishing Co., Philadelphia, PA 17th Ed. (1985); and *Modern Pharmaceutics*, Marcel Dekker, Inc. 3rd Ed. (G. S. Banker & C. T. Rhodes, Eds.).

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound or pharmaceutically acceptable salt thereof for the purpose of: (i) delaying the onset of a disease, that is, causing the clinical symptoms of the disease not to develop or delaying the development thereof; (ii) inhibiting the disease, that is, arresting the development of clinical symptoms; and/or (iii)

relieving the disease, that is, causing the regression of clinical symptoms or the severity thereof.

Liver Diseases

Liver diseases are acute or chronic damages to the liver based on the duration of the disease. The liver damage may be caused by infection, injury, exposure to drugs or toxic compounds such as alcohol or impurities in foods, an abnormal build-up of normal substances in the blood, an autoimmune process, a genetic defect (such as haemochromatosis), or other unknown causes. Exemplary liver diseases include, but are not limited to, cirrhosis, liver fibrosis, non-alcoholic fatty liver disease (NAFLD), non-alcoholic steatohepatitis (NASH), alcoholic steatohepatitis (ASH), hepatic ischemia reperfusion injury, primary biliary cirrhosis (PBC), primary sclerosing cholangitis (PSC), and hepatitis, including both viral and alcoholic hepatitis.

Non-alcoholic fatty liver disease (NAFLD) is the build up of extra fat in liver cells that is not caused by alcohol. NAFLD may cause the liver to swell (i.e. steatohepatitis), which in turn may cause scarring (i.e. cirrhosis) over time and may lead to liver cancer or liver failure. NAFLD is characterized by the accumulation of fat in hepatocyes and is often associated with some aspects of metabolic syndrome (e.g. type 2 diabetes mellitus, insulin resistance, hyperlipidemia, hypertension). The frequency of this disease has become increasingly common due to consumption of carbohydrate-rich and high fat diets. A subset (~20%) of NAFLD patients develop nonalcoholic steatohepatitis (NASH).

NASH, a subtype of fatty liver disease, is the more severe form of NAFLD. It is characterized by macrovesicular steatosis, balloon degeneration of hepatocytes, and/or inflammation ultimately leading to hepatic scarring (i.e. fibrosis). Patients diagnosed with NASH progress to advanced stage liver fibrosis and eventually cirrhosis. The current treatment for cirrhotic NASH patients with end-stage disease is liver transplant.

Another common liver disease is primary sclerosing cholangitis (PSC). It is a chronic or long-term liver disease that slowly damages the bile ducts inside and outside the liver. In patients with PSC, bile accumulates in the liver due to blocked bile ducts, where it gradually damages liver cells and causes cirrhosis, or scarring of the liver. Currently, there is no effective treatment to cure PSC. Many patients having PSC ultimately need a liver transplant due to liver failure, typically about 10 years after being diagnosed with the disease. PSC may also lead to bile duct cancer.

Liver fibrosis is the excessive accumulation of extracellular matrix proteins, including collagen, that occurs in most types of chronic liver diseases. Advanced liver fibrosis results in cirrhosis, liver failure, and portal hypertension and often requires liver transplantation.

Methods

Disclosed herein is a method of treating and/or preventing liver disease in a patient in need thereof, comprising administering to the patient a therapeutically effective amount of an ACC inhibitor in combination with a therapeutically effective amount of a FXR agonist. The presence of active liver disease can be detected by the existence of elevated enzyme levels in the blood. Specifically, blood levels of alanine aminotransferase (ALT) and aspartate aminotransferase (AST) above clinically accepted normal ranges are known to be indicative of on-going liver damage. Routine monitoring of liver disease patients for blood levels of ALT and AST is used clinically to measure progress of the liver disease while on medical treatment. Reduction of elevated ALT and AST to within the accepted normal range is taken as clinical evidence reflecting a reduction in the severity of the patient's on-going liver damage.

In certain embodiments, the liver disease is a chronic liver disease. Chronic liver diseases involve the progressive destruction and regeneration of the liver parenchyma, leading to fibrosis and cirrhosis. In general, chronic liver diseases can be caused by viruses (such as hepatitis B, hepatitis C, cytomegalovirus (CMV), or Epstein Barr Virus (EBV)), toxic agents or drugs (such as alcohol, methotrexate, or nitrofurantoin), a metabolic disease (such as non-alcoholic fatty liver disease (NAFLD), non-alcoholic steatohepatitis (NASH), haemochromatosis, or Wilson's Disease), an autoimmune disease (such as Autoimmune Chronic Hepatitis, Primary Biliary Cholangitis (formerly known as Primary Biliary Cirrhosis), or Primary Sclerosing Cholangitis, or other causes (such as right heart failure).

In one embodiment, provided herein is a method for reducing the level of cirrhosis. In one embodiment, cirrhosis is characterized pathologically by loss of the normal microscopic lobular architecture, with fibrosis and nodular regeneration. Methods for measuring the extent of cirrhosis are well known in the art. In one embodiment, the level of cirrhosis is reduced by about 5% to about 100%. In one embodiment, the level of cirrhosis is reduced by at least about 5%, at least about 10%, at least about 15%, at least about 20%, at least about 25%, at least about 30%, at least about 35%, at least about 40%, at least about 45%, at least 50%, at least about 55%, at least about 60%, at least about 65%, at least about 70%, at least about 75%, at least about 80%, at least about 85%, at least about 90%, or at least about 95% in the subject.

In certain embodiments, the liver disease is a metabolic liver disease. In one embodiment, the liver disease is non-alcoholic fatty liver disease (NAFLD). NAFLD is associated with insulin resistance and metabolic syndrome (obesity, combined hyperlipidemia, diabetes mellitus (type II) and high blood pressure). NAFLD is considered to cover a spectrum of disease activity, and begins as fatty accumulation in the liver (hepatic steatosis).

It has been shown that both obesity and insulin resistance probably play a strong role in the disease process of NAFLD. In addition to a poor diet, NAFLD has several other known causes. For example, NAFLD can be caused by certain medications, such as amiodarone, antiviral drugs (e.g., nucleoside analogues), aspirin (rarely as part of Reye's syndrome in children), corticosteroids, methotrexate, tamoxifen, or tetracycline. NAFLD has also been linked to the consumption of soft drinks through the presence of high fructose corn syrup which may cause increased deposition of fat in the abdomen, although the consumption of sucrose shows a similar effect (likely due to its breakdown into fructose). Genetics has also been known to play a role, as two genetic mutations for this susceptibility have been identified.

If left untreated, NAFLD can develop into non-alcoholic steatohepatitis (NASH), which is the most extreme form of NAFLD, a state in which steatosis is combined with inflammation and fibrosis. NASH is regarded as a major cause of cirrhosis of the liver. Accordingly, provided herein is a method of treating and/or preventing nonalcoholic steatohepatitis (NASH) in a patient in need thereof, comprising administering to the patient a therapeutically effective amount of an ACC inhibitor in combination with a therapeutically effective amount of a FXR agonist.

Also provided herein is a method of treating and/or preventing liver fibrosis in a patient in need thereof, comprising administering to the patient a therapeutically effective amount of an ACC inhibitor in combination with a therapeutically effective amount of a FXR agonist. Liver fibrosis is the excessive accumulation of extracellular matrix proteins including collagen that occurs in most types of chronic liver diseases. In certain embodiments, advanced liver fibrosis results in cirrhosis and liver failure. Methods for measuring liver histologies, such as changes in the extent of fibrosis, lobular hepatitis, and periportal bridging necrosis, are well known in the art.

In one embodiment, the level of liver fibrosis, which is the formation of fibrous tissue, fibroid or fibrous degeneration, is reduced by more that about 90%. In one embodiment, the level of fibrosis, which is the formation of fibrous tissue, fibroid or fibrous degeneration, is reduced by at least about 90%, at least about 80%, at least about 70%, at least about 60%, at least about 50%, at least about 40%, at least about 30%, at least about 20%, at least about 10%, at least about 5% or at least about 2%.

In one embodiment, the compounds provided herein reduce the level of fibrogenesis in the liver. Liver fibrogenesis is the process leading to the deposition of an excess of extracellular matrix components in the liver known as fibrosis. It is observed in a number of conditions such as chronic viral hepatitis B and C, alcoholic liver disease, drug-induced liver disease, hemochromatosis, auto-immune hepatitis, Wilson disease, Primary Biliary Cholangitis (formerly known as Primary Biliary Cirrhosis), sclerosing cholangitis, liver schistosomiasis and others. In one embodiment, the level of fibrogenesis is reduced by more that about 90%. In one embodiment, the level of fibrogenesis is reduced by at least about 90%, at least about 80%, at least about 70%, at least about 60%, at least about 50%, at least about 40%, at least about 30%, at least about 20%, at least about 10%, at least about 5% or at least 2%.

In still other embodiments, provided herein is a method of treating and/or preventing primary sclerosing cholangitis (PSC) in a patient in need thereof, comprising administering to the patient a therapeutically effective amount of an ACC inhibitor in combination with a therapeutically effective amount of a FXR agonist.

It has been observed that patients having NASH are on average about 2.8 years older than healthy patients in epigenetic testing. Thus, in one embodiment, compounds useful for the treatment of NASH would be useful for slowing, improving or reversing epigenetic age or effects of aging due to NASH. In another embodiment, combination therapies for the treatment of NASH such as, for example, the combination of an ACC inhibitor with an FXR agonist as disclosed herein may be useful for improvement or reversal of aging effects due to NASH.

In one embodiment, the ACC inhibitor and the FXR agonist may be administered together in a combination formulation or in separate pharmaceutical compositions, where each inhibitor may be formulated in any suitable dosage form. In certain embodiments, the methods provided herein comprise administering separately a pharmaceutical composition comprising an ACC inhibitor and a pharmaceutically acceptable carrier or excipient and a pharmaceutical composition comprising a FXR agonist and a pharmaceutically acceptable carrier or excipient. Combination formulations according to the present disclosure comprise an ACC inhibitor and a FXR agonist together with one or more pharmaceutically acceptable carriers or excipients and optionally other therapeutic agents. Combination formulations containing the active ingredient may be in any form suitable for the intended method of administration.

ACC Inhibitors

In certain embodiments of the methods and pharmaceutical compositions disclosed herein, the ACC inhibitor is a compound having the structure of Formula (I):

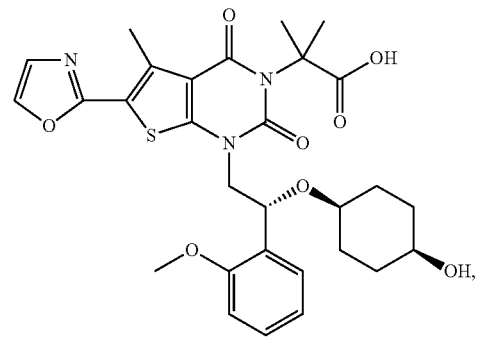 [SMILES: COc1ccccc1[C@H](Cn1c(=O)n(C(C)(C)C(=O)O)c(=O)c2c(C)c(-c3ncco3)sc21)O[C@H]1CC[C@@H](O)CC1]

or a pharmaceutically acceptable salt thereof.

In certain embodiments of the methods and pharmaceutical compositions disclosed herein, the ACC inhibitor is a compound having the structure of Formula (II):

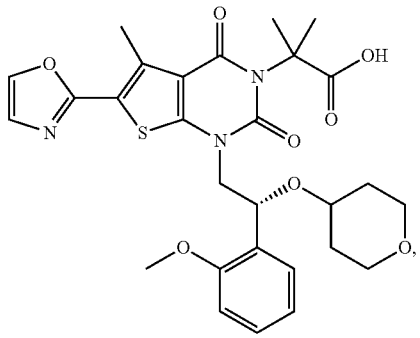 [SMILES: COc1ccccc1[C@H](Cn1c(=O)n(C(C)(C)C(=O)O)c(=O)c2c(C)c(-c3ncco3)sc21)OC1CCOCC1]

or a pharmaceutically acceptable salt thereof.

The compounds of Formula (I) and Formula (II) may be synthesized and characterized using methods known to those of skill in the art, such as those described in PCT International Application Publication No. WO 2013/071169. In one embodiment, the ACC inhibitor is the compound of Formula (I) or a pharmaceutically acceptable salt thereof. In one embodiment, the ACC inhibitor is the compound of Formula (II) or a pharmaceutically acceptable salt thereof.

FXR Agonist

In certain embodiments of the methods and pharmaceutical compositions disclosed herein, the FXR agonist is a compound having the structure of Formula (III):

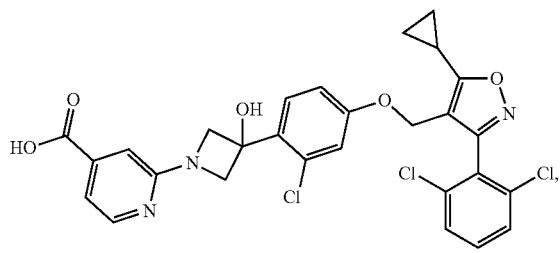 [SMILES: O=C(O)c1ccnc(N2CC(O)(c3ccc(OCc4c(-c5c(Cl)cccc5Cl)noc4C4CC4)cc3Cl)C2)c1]

or a pharmaceutically acceptable salt thereof.

In certain embodiments of the methods and pharmaceutical compositions disclosed herein, the FXR agonist is a compound having the structure of Formula (IV):

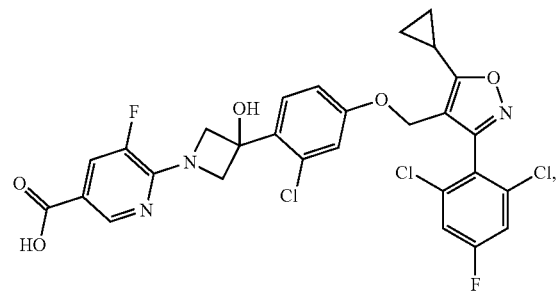 [SMILES: O=C(O)c1cnc(N2CC(O)(c3ccc(OCc4c(-c5c(Cl)cc(F)cc5Cl)noc4C4CC4)cc3Cl)C2)c(F)c1]

or a pharmaceutically acceptable salt thereof.

The compounds of Formula (III) and Formula (IV) may be synthesized and characterized using methods known to those of skill in the art, such as those described in U.S. Publication No. 2014/0221659.

Dosing and Administration

While it is possible for an active ingredient to be administered alone, it may be preferable to present them as pharmaceutical formulations or pharmaceutical compositions as described below. The formulations, both for veterinary and for human use, of the disclosure comprise at least one of the active ingredients, together with one or more acceptable carriers therefor and optionally other therapeutic ingredients. The carrier(s) must be "acceptable" in the sense of being compatible with the other ingredients of the formulation and physiologically innocuous to the recipient thereof.

Each of the active ingredients can be formulated with conventional carriers and excipients, which will be selected in accord with ordinary practice. Tablets can contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

The therapeutically effective amount of active ingredient can be readily determined by a skilled clinician using conventional dose escalation studies. Typically, each active ingredient will be administered in a dose from 0.01 milligrams to 1 gram. In one embodiment, the dosage will be from about 10 milligrams to 450 milligrams. In another embodiment, the dosage will be from about 25 to about 250 milligrams. In another embodiment, the dosage will be about 50 or 100 milligrams. In one embodiment, the dosage will be about 100 milligrams. In one embodiment, 20 mg of an ACC inhibitor is administered. In a specific embodiment, 20 mg of a compound of Formula (II) is administered. In one embodiment, 30 mg of an FXR agonist is administered. In a specific embodiment, 30 mg of a compound of Formula (III) is administered. It is contemplated that the active ingredients may be administered once, twice or three times a day. Also, the active ingredients may be administered once or twice a week, once every two weeks, once every three weeks, once every four weeks, once every five weeks, or once every six weeks.

The pharmaceutical composition for the active ingredient can include those suitable for the foregoing administration routes. The formulations can conveniently be presented in unit dosage form and may be prepared by any of the methods well known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration can be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste. In certain embodiments, the active ingredient may be administered as a subcutaneous injection.

A tablet can be made by compression or molding, optionally with one or more accessory ingredients. Compressed tablets can be prepared by compressing in a suitable machine the active ingredient in a free-flowing form such as a powder or granules, optionally mixed with a binder, lubricant, inert diluent, preservative, or surface active agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

The active ingredient can be administered by any route appropriate to the condition. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. In certain embodiments, the active ingredients are orally bioavailable and can therefore be dosed orally. In one embodiment, the patient is human.

When used in combination in the methods disclosed herein, the ACC inhibitor and the FXR agonist can be administered together in a single pharmaceutical composition, e.g. a fixed dose combination, or separately (either concurrently or sequentially) in more than one pharmaceutical composition. In certain embodiments, the ACC inhibitor and the FXR agonist are administered together. In other embodiments, the ACC inhibitor and the FXR agonist are administered separately. In some aspects, the ACC inhibitor is administered prior to the FXR agonist. In some aspects, the FXR agonist is administered prior to the ACC inhibitor. When administered separately, the ACC inhibitor and the FXR agonist can be administered to the patient by the same or different routes of delivery.

Pharmaceutical Compositions

The pharmaceutical compositions of the disclosure comprise an effective amount of an ACC inhibitor selected from the group consisting of a compound of Formula (I) and a compound of Formula (II), or a pharmaceutically acceptable salt thereof, and an effective amount of a FXR agonist selected from the group consisting of a compound of Formula (III) and a compound of Formula (IV), or a pharmaceutically acceptable salt thereof.

When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcelluose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose.

Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration, such as oral administration or subcutaneous injection. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. When formulated for subcutaneous administration, the formulation is typically administered about twice a month over a period of from about two to about four months.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations can be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

EXAMPLES

Example 1. Efficacy in a Mouse Model of NASH

The following study was conducted to evaluate the efficacy of the combination of an ACC inhibitor and an FXR agonist in a mouse model of non-alcoholic steatohepatitis (NASH), relative to the efficacy of the individual agents alone in the model. NASH was induced in male C57BL/6 mice by chronic administration of a "fast food" diet (FFD) high in saturated fats, cholesterol and sugars for a total of 6 months, whereas lean control animals were maintained on a normal chow diet. A NASH phenotype was established in FFD mice compared to control mice after 6 months, and was characterized by macrovesicular steatosis, elevated ALT and AST, and increased levels of transcripts associated with hepatic stellate cell activation. See Charlton M, et al. Fast food diet mouse: novel small animal model of NASH with ballooning, progressive fibrosis, and high physiological fidelity to the human condition. American Journal of Physiology. Gastrointestinal and Liver Physiology 2011; 301 (5):G825-34.

After 5 months, FFD mice were subsequently treated with placebo (vehicle), an ACC inhibitor (Formula (I)), an FXR agonist (Formula (III)), or with the combination of Formula (I) and Formula (III) for 1 month. Control mice remained on a normal chow diet for the entire 6 month study period. Endpoint analyses included biochemical quantification of liver triglycerides, plasma ALT, and measurement of the pro-fibrotic transcripts Timp1 and Col1A1 in liver.

Methods

Animals

Male C57CL/6 mice (aged 12 weeks at study inception) were used in this study. All procedures used to study the animals were in the compliance with the U.S. Department of Agriculture's Animal Welfare Act (9 CFR Parts 1, 2, and 3); the Guide for the Care and Use of Laboratory Animals (Institute for Laboratory Animal Research, The National Academies Press, Washington, D.C.); and the National Institutes of Health, Office of Laboratory Animal Welfare.

In-Life Experimental Protocol for the FFD Mouse Model

The experimental design is shown in Table 1. Study animals were administered either a standard chow diet (Harlan Teklad Global Diets 2014, TD2014) or a commercially available high fat, high cholesterol diet (Research Diets Inc, DB12079B) (the FFD). Animals receiving the FFD were administered fructose/glucose in drinking water formulated as follows: 23.1 g 5 fructose (Sigma, F2543) and 17.2 g of glucose (Sigma, 49158) was mixed into 1000 mL of drinking water.

The compound of Formula (I) or the compound of Formula (III) alone, or the combination of the compounds of Formula (I) and Formula (II), were administered for the final month of the study (month 5-month 6). The compound of Formula (I) and the compound of Formula (III) were formulated in 0.5% sodium carboxymethylcellulose (medium viscosity), 1% w/w ethanol, 98.5% w/w 50 mM Tris Buffer, pH 8 in reverse osmosis water. The compound of Formula (I) was formulated at either 0.1 or 0.2 mg/mL and given in the dose provided in Table 1, and the compound of Formula (III) was formulated at 2 mg/mL and given in the dose provided in Table 1.

Starting seven days before PO dosing, animals in groups 1-6 were sham dosed with vehicle BID. The sham dosing was designed to acclimate animals to oral gavage dose administration. Starting at Day 1 of the study, animals in all dose groups were dosed three times daily; twice sequentially in the AM (7:00+/−1 hour), and once in the evening (19:00+/−1 hr), with the same volume of formulation containing no compound (group 1, vehicle) or the appropriate compounds as outlined below (Table 1) for 28 days (until dosing Day 29). Each group was split into two and half were sacrificed 2 hours post dose, and half were sacrificed 8 hours post dose on Day 29.

TABLE 1

Experimental Design and Dose Groups

| Group | Test Article | Dose (mg/kg) | Dose Vol (mL/kg) | Concentration (mg/mL) | Number of Animals | Dosing Frequency (x/day) | Dosing Duration (days) | Route |
|---|---|---|---|---|---|---|---|---|
| 1 | Vehicle | 0 | 5 | 0 | 15 | TID | 29 | PO |
| 2 | Vehicle | 0 | 5 | 0 | 15 | QD | 29 | PO |
|   | Formula (I) | .5 | 5 | 0.1 |   | BID | 29 | PO |
| 3 | Vehicle | 0 | 5 | 0 | 15 | BID | 29 | PO |
|   | Formula (III) | 10 | 5 | 2 |   | QD |   |   |
| 4 | Formula (I) | 0.5 | 5 | 0.1 | 16 | BID | 29 | PO |
|   | Formula (III) | 10 | 5 | 2 |   | QD |   |   |
| 5 | Vehicle (age-matched lean) | 0 | 5 | 0 | 10 | TID | 29 | PO |

Quantification of Triglycerides from Murine Liver

Tissue Extraction: Mouse liver tissue samples (25±10 mg, accurately weighed in frozen state) were homogenized and extracted with a water immiscible organic solvent mixture that extracts the triacylglyceride fraction as well as the free and esterified cholesterol fractions into the organic phase. After centrifugation, an aliquot of the organic upper layer, containing the triacylglycerides, cholesterol and cholesterol esters was diluted either 10-fold or 25-fold with ethanol. Two separate aliquots of this dilution were taken. One aliquot was analyzed for triacylglycerides, the second aliquot was used for the total cholesterol determination.

Triacylglyceride Determination: For the triacylglyceride determination, one aliquot of the 25-fold dilution (or no dilution in the case of samples which have low triacylglyceride content) was evaporated under a stream of nitrogen. The dried extract was reconstituted stepwise with a 0.1% sodium dodecyl sulfate in PBS solution under ultrasonication followed by mixing with the Triacylglyceride Determination Reagent (Infinity™ Triglycerides Liquid Stable Reagent, Thermo Scientific, Product Data Sheet, Infinity™, Triglycerides Liquid Stable Reagent).

This reagent solution contained several enzymes, cofactors and the chromogenic reagent 4-aminoantipyrine. The determination of triacylglycerides (TAG) with this reagent was based on the method of Wako, Product Data Sheet, Triacylglyceride-G Code No. 997-69801, Wako Pure Chemical Industries Ltd., Dallas, TX, and the modifications by McGowan et al, (McGowan, M W, et al., Clin. Chem 1983:29:538) and Fossati et al (Fosseti, P. Prenciple L. Clin Chem. 1892:28:2077-80) as follows:

1. Triglycerides are enzymatically hydrolyzed by lipase to free fatty acids and glycerol.
2. The glycerol is phosphorylated by adenosine triphosphate (ATP) with glycerol kinase (GK) to produce glycerol-3-phosphate and adenosine diphosphate.
3. Glycerol-3-phosphate is oxidized by dihydroxyacetone phosphate (DAP) by glycerol phosphate oxidase producing hydrogen peroxide ($H_2O_2$).
4. In a Trinder[5]-type colour reaction catalyzed by peroxidase, the $H_2O_2$ reacts with 4-aminoantipyrine (4-AAP) and 3,5-dichloro-2-hydroxybenzene sulfonate (DHBS) to produce a red colored dye. The absorbance of this dye is proportional to the concentration of triglycerides present in the sample.

After incubation with the Triacylglyceride Determination Reagent for 30 min at 37° C., samples were transferred into a microtiter plate, and the absorbance is measured at 540 nm in a microplate reader (SpectraMax M2, Molecular Devices). Quantitation was performed using a linear least squares regression analysis generated from fortified calibration standards using glyceryl trioleate (triolein) as triacylglyceride reference standard. Calibration standard samples were taken through the same extraction and incubation steps as the tissue samples. Weight 5 corrections and concentration calculations were performed using Microsoft Excel 2013. Final tissue contents were given in μmol Triacylglyceride (TAG)/g Liver Tissue.

ALT

Serum was collected from all mice at terminal necroscopy. Serum ALT was measured by Pyruvate with pyridoxal-5'-phosphate and analyzed on the Cobas Hitachi 6000 Chemistry System, Roche Diagnostics.

Gene Expression

An approximately 100 mg chunk of frozen left lateral lobe was sent to DC3 Therapeutics, LLC for lysing and RNA extraction. NanoString assays were carried out with all reagents and consumables contained in an nCounter master kit (NanoString) according to manufacturer instructions to measure RNA transcripts. Briefly, the color coded reporter probe targeting 110 liver fibrosis related genes and 6 control housekeeping genes (Table 2) were hybridized overnight in a pre-heated 65° C. thermocycler for 16 to 22 hours with 100 ng RNA samples in a reaction that includes a hybridization buffer and a capture probe. Following incubation, samples were placed on a prep station where excess probes were removed and the probe-transcript complexes were immobilized on a streptavidin coated cartridge. Finally, the cartridges were imaged in the nCounter Digital Analyzer (NanoString Technologies, Seattle, WA). All transcripts were normalized to the geometric mean of 6 housekeeping genes (B2m, Hprt, Pgk1, Rp113a, Rpn1, and Sfrs4) with nSover 3.0 software.

TABLE 2

Nanostring Probes

| Gene Symbol | Accession Number | Target Sequence |
|---|---|---|
| TIMP1 | NM_011593.2 | AAGCCTCTGTGGATATGCCCACAAGTCCCAGAACCGCAGTGAAGAGTTTCTCATC ACGGGCCGCCTAAGGAACGGAAATTTGCACATCAGTGCCTGCAGC |

TABLE 2-continued

Nanostring Probes

| Gene Symbol | Accession Number | Target Sequence |
|---|---|---|
| COL1A1 | NM_007742.3 | CAATGGTGAGACGTGGAAACCCGAGGTATGCTTGATCTGTATCTGCCACAATG GCACGGCTGTGTGCGATGACGTGCAATGCAATGAAGAACTGGACTGT |
| B2M | NM_009735.3 | CATACGCCTGCAGAGTTAAGCATGCCAGTATGGCCGAGCCCAAGACCGTCTAC TGGGATCGAGACATGTGATCAAGCATCATGATGCTCTGAAGATTCAT |
| HPRT | NM_013556.2 | TGCTGAGGCGGCGAGGGAGAGCGTTGGGCTTACCTCACTGCTTTCCGGAGCG GTAGCACCTCCTCCGCCGGCTTCCTCCTCAGACCGCTTTTTGCCGCGA |
| PGK1 | NM_008828.2 | CCGGCATTCTGCACGCTTCAAAAGCGCACGTCTGCCGCGCTGTTCTCCTCTTCCTC ATCTCCGGGCCTTTCGACCTCACGGTGTTGCCAAAATGTCGCTT |
| RPL13a | NM_009438.5 | ATGGGATCCCTCCACCCTATGACAAGAAAAAGCGGATGGTGGTCCCTGCTGCT CTCAAGGTTGTTCGGCTGAAGCCTACCAGAAAGTTTGCTTACCTGGG |
| RPN1 | NM_133933.3 | GGCAGCCTGACAGTGGGATCTCCTCCATTCGTTCTTTTAAGACCATCCTTCCTG CTGCCGCCCAGGATGTCTATTACCGGGATGAGATTGGTAATGTTTC |
| SFRS4 | NM_020587.2 | GATGCTCACAAGGGACGCAAAAACGAAGGAGTGATTGAATTTGTGTCTTACTCT GATATGAAAAGAGCTTTGGAAAAGCTGGACGGAACTGAAGTCAACG |

Results

Figure 2:
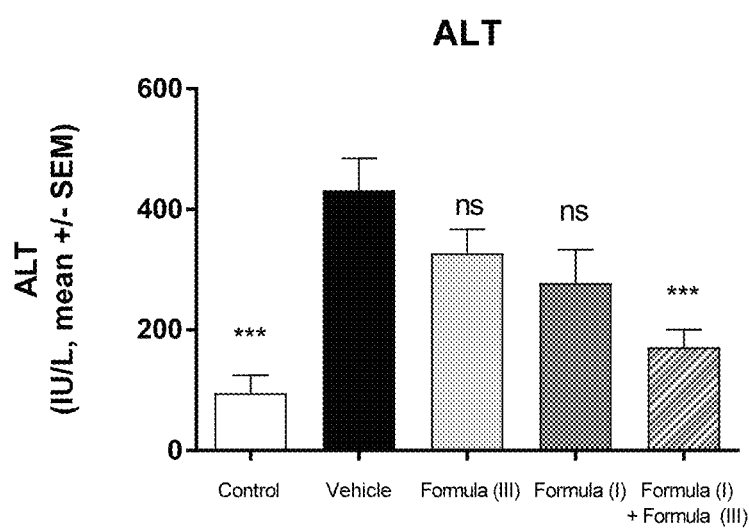
FIG. 2. ALT IU/L in the murine FFD model. (***$p<0.001$; significantly different from vehicle by ANOVA). Graph shows mean±SEM.
Figure 3:
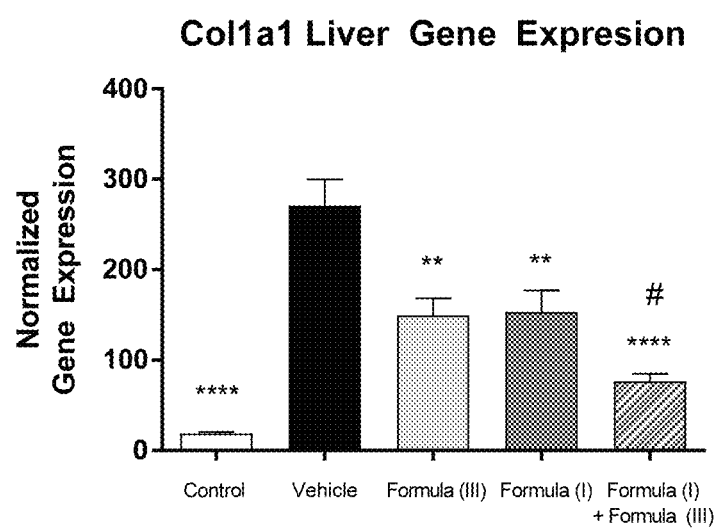
FIG. 3. Hepatic expression of liver fibrosis gene Col1a1 measured by quantitative RT-PCR in the murine FFD model. ($p<0.01$; **$p<0.0001$ significantly different from vehicle by ANOVA; # significantly different from either single agent by t-test). Graph shows mean±SEM.
Figure 4:
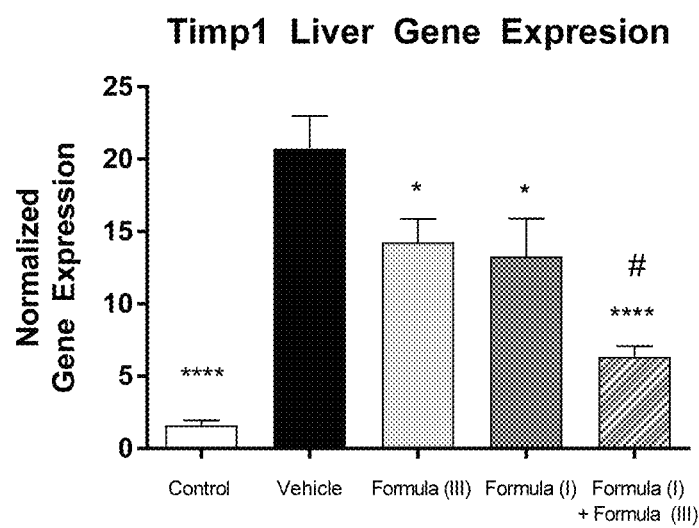
FIG. 4. Hepatic expression of liver fibrosis gene Timp1 measured by quantitative RT-PCR in the murine FFD model. (*$p<0.05$; ****$p<0.0001$ significantly different from vehicle by ANOVA; # significantly different from either single agent by t-test). Graph shows mean±SEM.
Figure 5:
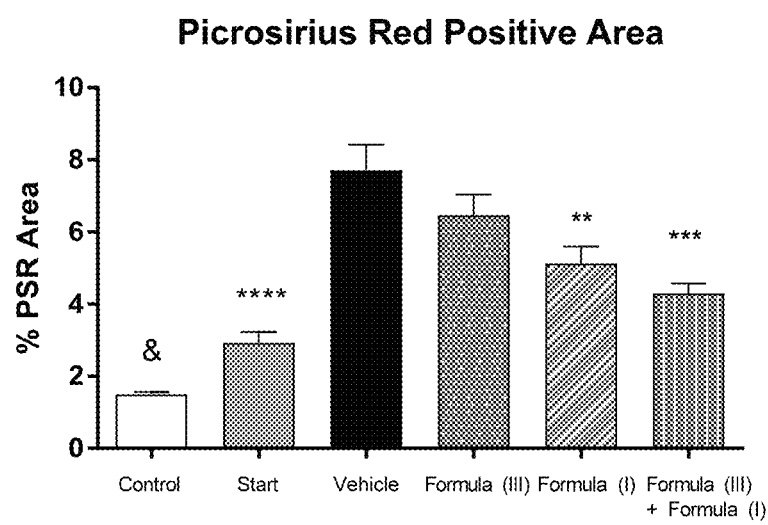
FIG. 5. Percent PSR positive area by quantitative image analysis in the rat CDHFD model. ($p<0.01$, *$p<0.001$, ****$p<0.0001$ significantly different from vehicle by t-test; & $p<0.001$ significantly different from start of treatment by t-test). Graph shows mean±SEM.

Example 1 demonstrates that a combined treatment with an ACC inhibitor and an FXR agonist results in greater efficacy than either agent administered alone in the mouse model of NASH. In particular, FIG. 1 shows a significant reduction in liver triglycerides with the combination of the compound of Formula (I) and the compound of Formula (III) relative to the individual agents, FIG. 2 shows a significant reduction in serum ALT with the combination of the compound of Formula (I) and the compound of Formula (III) relative to the individual agents, and FIG. 3 and FIG. 4 show a significant reduction in liver expression of Col1a1 and Timp1 with the combination of the compound of Formula (I) and the compound of Formula (III) relative to the individual agents, respectively.

Example 2. Efficacy in a Rat Model of NASH

The following study was conducted to evaluate the efficacy of the combination of an ACC inhibitor and an FXR agonist in a rodent model of non-alcoholic steatohepatitis (NASH) with fibrosis relative to the efficacy of the individual agents alone in the model. In this model, NASH with fibrosis was induced in male Wistar rats by administration of a choline-deficient high fat diet (CDHFD).

Animals

Male Wistar (Crl:Wi(Han)) rats (aged 8-9 weeks at arrival) were acquired from Charles River, Raleigh, NC, and used in the current studies. This study complied with all applicable sections of the Final Rules of the Animal Welfare Act regulations (Code of Federal Regulations, Title 9), the Public Health Service Policy on Humane Care and Use of Laboratory Animals from the Office of Laboratory Animal Welfare, and the Guide for the Care and Use of Laboratory Animals from the National Research Council.

Vehicle Preparation

The vehicle, w/v 50 mM tris buffer, pH 8 in deionized water, was prepared prior to use and stored in a refrigerator set to maintain 2-8° C. To prepare 1 L, 800 mL of hot water (~80° C.) was added to an appropriate container and stirred vigorously until a steep vortex formed. 5.0 grams of sodium methylcellulose was slowly added to the sodium carboxymethylcellulose to the vortex. Stirring was continued until all carboxymethylcellulose was dissolved and the solution cooled down to ambient temperature. 5.12 g of Tris HCl was added to the container. 2.12 g of Tris base was added to the container. 10 g of ethanol was added to the container. The components were stirred for approximately 15 minutes, ensuring all solids have dissolved. QS water was added to 1 L with gentle mixing.

Study Design

Food was pro libitum and all animals on study were given a choline-deficient, high fat, high cholesterol diet (CDHFD; Research Diets, A16092003) on Day 1 of study except for group 1, the control chow group, which received standard diet (5CR4), as outlined in Table 3. On the day of sacrifice, liver was harvested and paraffin embedded, and plasma was collected and frozen. Animals were not dosed the day of sacrifice.

TABLE 3

Experimental Design and Dose Groups

| Group | Group name | n | Diet (weeks) | Treatment (PO) |
|---|---|---|---|---|
| 1 | Control | 10 | Standard Diet (0-12) | N/A |
| 2 | Start of Treatment | 10 | CDHFD (0-6) | N/A |
| 3 | Vehicle | 15 | CDHFD (1-12) | N/A |
| 4 | Compound of Formula (I) | 15 | CDHFD (1-12) | 10 mg/kg QD |
| 5 | Compound of Formula (III) | 15 | CDHFD (1-12) | 30 mg/kg QD |
| 6 | Compound of Formula (I) + Compound of Formula (III) | 15 | CDHFD (1-12) | 10 mg/kg QD + 30 mg/kg QD |

Tissues were collected by Charles River in Reno, Nevada, processed and embedded in paraffin at Histo-tec in Hayward, CA and then shipped to Gilead Sciences in Foster City. Samples were sectioned at 5 μm and sections were mounted on glass slides for subsequent staining.

Picrosirius red staining: Sections were pretreated in 0.2% Phosphomolybdic Acid (EMS, Cat #26357-01) and then subsequently incubated in 0.1% (W/V) Sirius Red 88-89-1 in saturated Picric acid solution (EMS, Cat #26357-02) for 1 hour at room temperature. This was followed by differentiation in 0.01N HCl (EMS, Cat #26357) and dehydration in graded alcohols.

Figure 7:
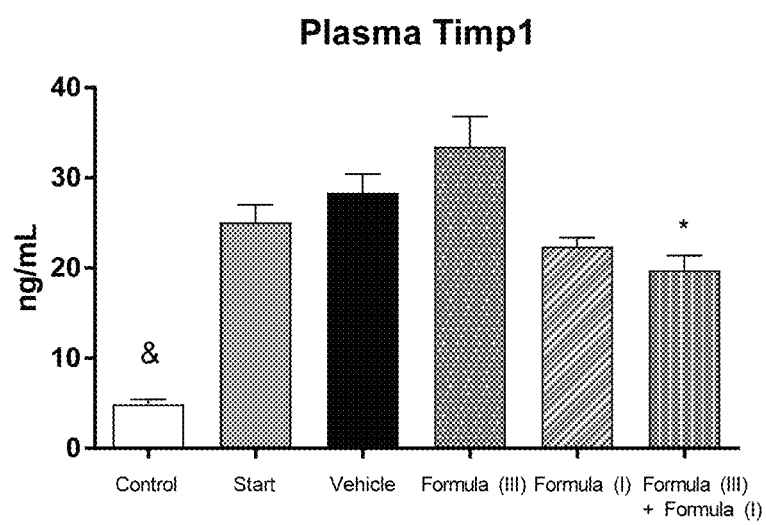
FIG. 7. Timp1 protein measured in plasma by ELISA in the rat CDHFD model. (*$p<0.05$ significantly different from vehicle by t-test; & $p<0.001$ significantly different from start of treatment by t-test). Graph shows mean±SEM.

Whole slide images of Picrosirius Red (PSR) stained slides were captured using a Leica AT2 scanner at 40× magnification. Digital slide images were checked for scanning quality, annotated and exported to appropriate network folders within Leica Digital Image Hub archive. Quantitative image analysis was performed on the whole slide images using Visiopharm image analysis software (Visiopharm, Hoersholm, Denmark) to determine the extent and intensity of PSR. The total PSR-stained area was measured and expressed as a percentage of total liver area stained. Results are shown in FIG. 7.

α-SMA: Sections were deparaffinized in 3 changes of xylene for 5 minutes each, and subsequently rehydrated in 3 changes of 100% EtOH, 1 change of 95% EtOH, 1 change of 80% EtOH for 3 minutes each; followed by 2 successive rinses in distilled water. The sections were then incubated in Peroxidazed 1 (Biocare Medical, Cat #PX968) endogenous peroxidase blocker for 5 minutes and rinsed in distilled water. Heat induced epitope retrieval was then performed using Reveal Decloaker (Biocare Medical, Cat #RV1000M) at 95° C. for 40 minutes with a Decloaking Chamber NxGen (Biocare Medical, Cat #DC2012), followed by gradual cooling with replacement of retrieval buffer with distilled water and placed in tris buffered saline (TBS). Immunohistochemistry was performed on prepared slides using an Intellipath autostainer (Biocare Medical, Cat #IPS0001) using the following steps:

1. Apply 300 uL of Background Punisher (Biocare Medical, Cat #IP974G20) to slides and incubate for 10 minutes; followed by TBS wash.
2. Apply 300 uL primary antibody of mouse monoclonal SMA, clone 1A4, (Biocare Medical, Cat #CM001) diluted 1:50 in Da Vinci Green diluent (Biocare Medical, Cat #PD900L). Incubate for 30 Minutes at room temperature; followed by TBS wash.
3. Apply 300 uL of Mouse on Rat HRP Polymer (Biocare Medical, Cat #MRT621H) and incubate for 30 minutes; followed by TBS wash.
4. Prepare DSB: 1 drop of DSB Chromogen/1 ml Substrate Buffer (Biocare Medical, Cat #BRI 4014C/BRI 4013 respectfully). Apply 300 uL Deep Space Black (DSB) Chromogen for 5 minutes; followed by distilled water wash.
5. Counterstain with Nuclear Fast Red (Biocare Medical, Cat #STNFRLT) for 1 minute; followed by distilled water wash.

Slides were removed from the instrument and dehydrated through a series of graded histological grade alcohols to xylene and coverslipped.

Whole slide images of α-SMA stained slides were captured using a Leica AT2 scanner at 40× magnification. Digital slide images were checked for scanning quality, annotated and exported to appropriate network folders within Leica Digital Image Hub archive. Quantitative image analysis was performed on the whole slide images using Visiopharm image analysis software (Visiopharm, Hoersholm, Denmark) to determine the extent and intensity of α-SMA. The total α-SMA-stained area was measured and expressed as a percentage of total liver area stained.

Plasma TIMP-1 ELISA: Plasma TIMP-1 concentrations were determined in duplicate using a commercially available rat TIMP-1 specific ELISA kit (R&D Systems, Minneapolis, MN, Cat #RTM100). TIMP-1 was assayed in plasma according to the manufacturer's specifications with minor modifications. Buffer RD1-21 (50 µl) was added to ELISA plate wells pre-coated with mouse anti-TIMP-1. Prior to ELISA, a seven point standard curve of rat TIMP-1 (NS0-expressed recombinant TIMP-1: 2400-37.5 pg/mL) was generated and plasma samples were diluted 1:20 in buffer RD5-17. Samples and standards (50 µl each) were added in duplicate to wells containing RD1-21 and incubated (room temperature) for 2 hours on an orbital plate shaker (300 rpm). Following antigen capture, plates were washed 5 times (350 µL/well/wash) with Wash Buffer using an automated plate washer. Following washing, rat TIMP-1 conjugate (100 µl) was added to each well and plates were incubated (room temperature) for 2 hours on an orbital plate shaker (300 rpm). Plates were then washed 5 times and Substrate Solution (100 µl) was added to each well. Plates were incubated at room temperature for 30 minutes protected from light. Finally, Stop Solution (100 µl) was added to each well. Optical Density (O.D.) absorbance was immediately determined at 450 nm on a SpectraMax 190 microplate reader (Molecular Devices, Sunnyvale CA). Relative O.D.s for each standard and sample were background corrected against blank samples, and standard curves for conversion of O.D.s to TIMP-1 concentration were generated using a 4 Parameter curve fit method. Unknown sample TIMP-1 concentrations were determined using SoftMax Pro5 software using a dilution factor of 20. Results are shown in FIG. 7.

Figure 9:
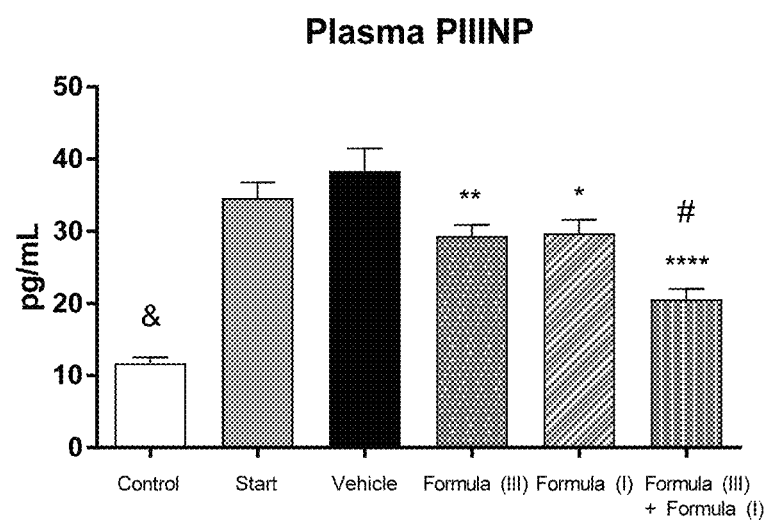
FIG. 9. N-terminal propeptide of Type III Collagen (PIINP) measured in plasma by ELISA in the rat CDHFD model. (*$p<0.05$,$p<0.01$, **$p<0.0001$ significantly different from vehicle by t-test; & $p<0.001$ significantly different from start of treatment by t-test; #$p<0.05$ significantly different from either single agent by t-test). Graph shows mean±SEM.

Plasma PIIINP: Plasma PIIINP concentrations were determined in duplicate using a commercially available rat Procollagen III N-Terminal Propeptide (PIIINP) ELISA Kit (Biomatik, Wilmington, DE, Cat #EKU06788). PIIINP was assayed in plasma diluted 50 fold in PBS according to the manufacturer's specifications with minor modifications. 7 standards (2,000 pg/mL, 1,000 pg/mL, 500 pg/mL, 250 pg/mL, 125 pg/mL, 62.5 pg/mL, 31.2 pg/mL) were prepared from standard stock which was reconstituted in Standard Diluent. 100 µL each of 5 standards, blank and samples were added into the appropriate wells. The plate was covered with the plate sealer and incubated for 1 hour at 37° C. After removing liquid from each well, 100 µL of Detection Reagent A working solution was added to each well and covered with the plate sealer then incubated for 1 hour at 37° C. The wells were washed with 350 µL of 1×Wash and sit for 1~2 minutes for 3 times. After the last wash, any remaining wash buffer was removed by decanting and blotting against absorbent paper. Then 100 µL of Detection Reagent B working solution was added to each well, plate was covered with the plate sealer and incubated for 30 minutes at 37° C. The aspiration/wash process was repeated for total 5 times. 90 µL of Substrate Solution was added to each well, plate was covered with a new plate sealer and incubated for 10-20 minutes at 37° C. protecting from light. The liquid turned blue by the addition of Substrate Solution. Finally 50 µL of Stop Solution was added to each well. The liquid then turned yellow. Mix the liquid by gently tapping the side of the plate. Optical Density (O.D.) absorbance was immediately determined at 450 nm on a SpectraMax 190 microplate reader (Molecular Devices, Sunnyvale CA). Relative O.D.s for each standard and sample were background corrected against blank samples, and standard curves for conversion of O.D.s to PIIINP concentration were generated using a 4 Parameter curve fit method. Unknown sample PIIINP concentrations were determined using SoftMax Pro5 software using a dilution factor of 50. Results are shown in FIG. 9.

Figure 8:
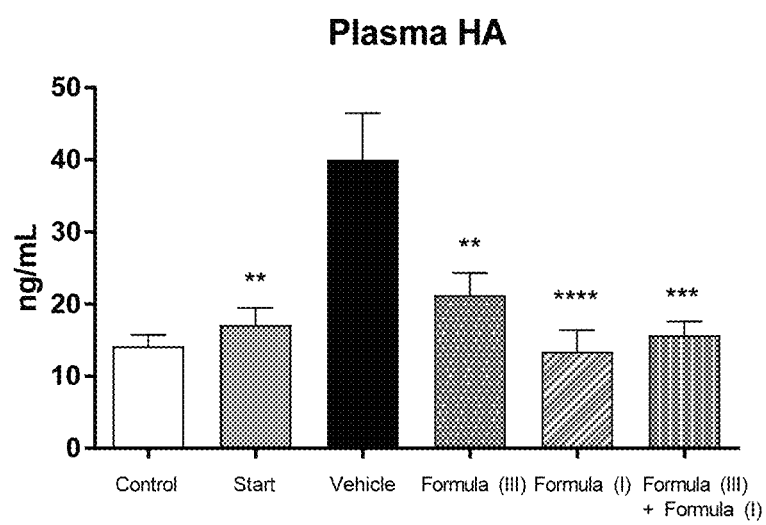
FIG. 8. Hyaluronic acid (HA) measured in plasma by ELISA in the rat CDHFD model. $p<0.01$, *$p<0.001$, ****$p<0.0001$ significantly different from vehicle by t-test). Graph shows mean±SEM.

Plasma Hyaluronic Acid (HA) Assay: Plasma HA concentrations were determined in duplicate using a commercially available HA Test Kit (Corgenix, Inc., Broomfield, CO, Cat #029-001). HA was assayed in plasma according to the manufacturer's specifications with minor modifications. Prior to assay, a seven point standard curve of HA reference solution (800-12.5 ng/mL) was generated and each reference sample and plasma sample was diluted 1 part to 10 parts Reaction Buffer (30 μl reference/sample to 300 μl Reaction Buffer). Samples and standards (100 μl) were added in duplicate to microplate wells pre-coated with HA binding protein (HABP) and incubated (room temperature) for 60 minutes on an orbital plate shaker (300 rpm). Following antigen capture, plates were washed 4 times (350 L/well/wash) with PBS using an automated plate washer. Following washing, HRP-conjugated HABP (100 μl) was added to each well and plates were incubated (room temperature) for 30 minutes on an orbital plate shaker (300 rpm). Plates were then washed 4 times and the one-component Substrate Solution (100 μl) was added to each well. Plates were incubated at room temperature for 30 minutes protected from light. Finally, Stop Solution (100 μl) was added to each well. Optical Density (O.D.) absorbance was immediately determined at 450 nm on a SpectraMax 190 microplate reader (Molecular Devices, Sunnyvale CA). Relative O.D.s for each standard and sample was background corrected against blank samples, and standard curves for conversion of O.D.s to HA concentration was generated using a 4 Parameter curve fit method. Undiluted unknown sample HA concentrations were determined using SoftMax Pro5 software. Results are shown in FIG. 8.

Results

Figure 6:
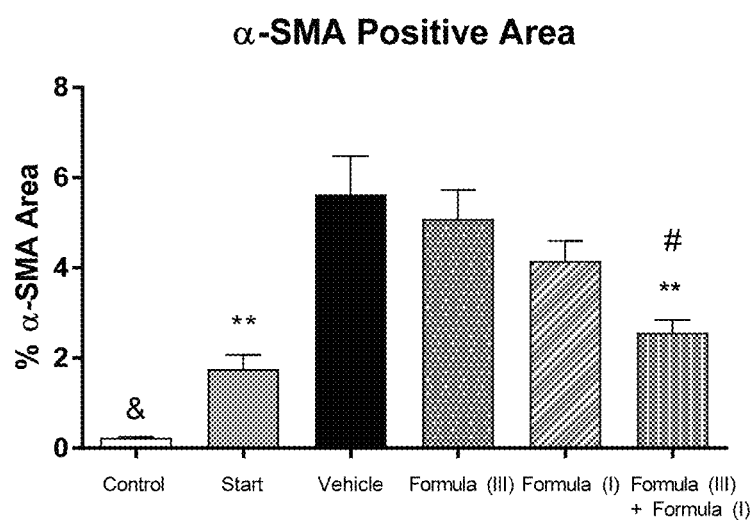
FIG. 6. Percent α-SMA positive area by quantitative image analysis in the rat CDHFD model. (**$p<0.01$ significantly different from vehicle by t-test; & $p<0.001$ significantly different from start of treatment by t-test; #$p<0.05$ significantly different from either single agent by t-test). Graph shows mean±SEM.

Example 2 demonstrates that a combined treatment with an ACC inhibitor and an FXR agonist results in greater efficacy than either agent administered alone in the rat model of NASH. In particular, FIG. 5-9 shows a significant reduction markers of fibrosis including percent picrosirius positive area, percent α-SMA positive area, and three plasma markers associated with fibrosis, TIMP1, HA, and PIIINP with the combination of the compound of Formula (I) and the compound of Formula (III) relative to the vehicle. FIG. 6 and FIG. 9 show a significant reduction α-SMA and PIIINP with the combination of the compound of Formula (I) and the compound of Formula (III) relative to the individual agents, respectively.

What is claimed is:

1. A method of treating non-alcoholic steatohepatitis (NASH) in a patient in need thereof, wherein the patient has advanced liver fibrosis and cirrhosis, comprising administering to the patient a therapeutically effective amount of a compound of Formula (II):

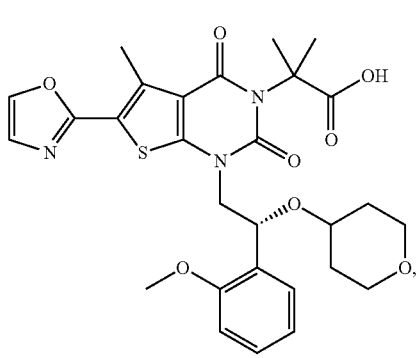
(II)

or a pharmaceutically acceptable salt thereof;
and a therapeutically effective amount of a compound of Formula (III):

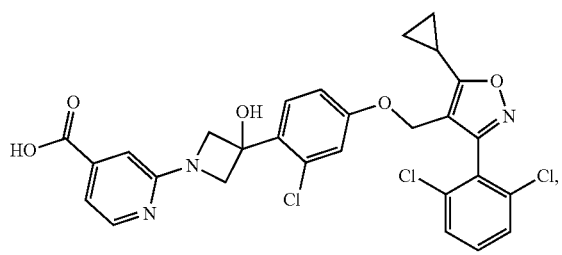
(III)

or a pharmaceutically acceptable salt thereof.

2. The method of claim 1, wherein the compound of Formula (II) and the compound of Formula (III) are administered together.

3. The method of claim 1, wherein the compound of Formula (II) and the compound of Formula (III) are administered separately.

4. A pharmaceutical composition for treating non-alcoholic steatohepatitis (NASH) in a patient having advanced liver fibrosis and cirrhosis, wherein the composition comprises a therapeutically, effective amount of a compound of Formula (II):

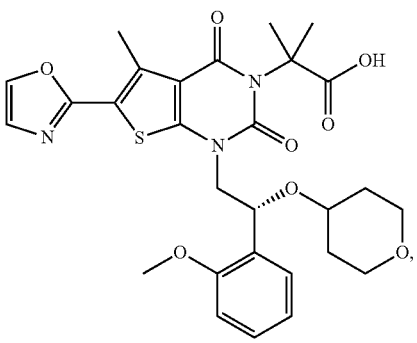
(II)

or a pharmaceutically acceptable salt thereof;
a therapeutically effective amount of a compound of Formula (III):

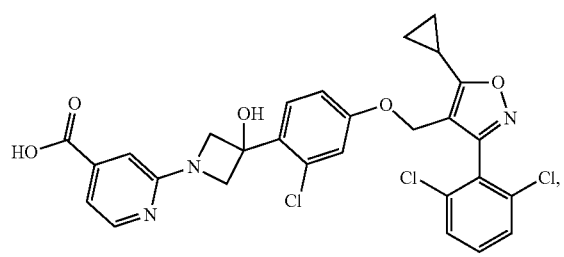
(III)

or a pharmaceutically acceptable salt thereof;
and a pharmaceutically acceptable carrier.

* * * * *